United States Patent [19]
Sakae et al.

[11] Patent Number: 6,136,823
[45] Date of Patent: Oct. 24, 2000

[54] PYRIDONECARBOXYLIC ACID DERIVATIVES OR SALTS THEREOF AND DRUGS CONTAINING THE SAME AS THE ACTIVE INGREDIENT

[75] Inventors: Nobuya Sakae; Akira Yazaki; Yasuhiro Kuramoto; Jiro Yoshida; Yoshiko Niino; Yoshihiro Ohshita; Yuzo Hirao; Norihiro Hayashi; Hirotaka Amano, all of Hiroshima, Japan

[73] Assignee: Wakunaga Pharmaceutical Co., Ltd., Osaka, Japan

[21] Appl. No.: 09/308,641

[22] PCT Filed: Nov. 27, 1997

[86] PCT No.: PCT/JP97/04326

§ 371 Date: May 28, 1999

§ 102(e) Date: May 28, 1999

[87] PCT Pub. No.: WO98/23592

PCT Pub. Date: Jun. 4, 1998

[30]     Foreign Application Priority Data

Nov. 28, 1996  [JP]  Japan ..................................... 8-317693
Jun. 24, 1997  [JP]  Japan ..................................... 9-167245

[51] Int. Cl.$^7$ .......................... C07D 215/16; A61K 31/47
[52] U.S. Cl. ............................. 514/312; 546/156
[58] Field of Search .............................. 546/156; 514/312

[56]                  References Cited

FOREIGN PATENT DOCUMENTS

| | | |
|---|---|---|
| 9 897 919 | 2/1999 | European Pat. Off. . |
| 0 911 336 | 4/1999 | European Pat. Off. . |

OTHER PUBLICATIONS

USPatFull abstract 1999:65254, abstract of US Patent #5,910,498, 1999.
Marpat abstract #126:47239, abstract of Matsumoto, 1996.
Marpat abstract #126:47238, abstract of Matsumoto, 1996.
Marpat abstract #115:74146, abstract of Arnold, 1991.
Marpat abstract #114:247159, abstract of Bitha, 1991.

*Primary Examiner*—D. Margaret Seaman
*Attorney, Agent, or Firm*—Oblon, Spivak, McClelland, Maier & Neustadt, P.C.

[57]                  ABSTRACT

The invention relates to pyridonecarboxylic acid derivatives represented by the general formula (1):

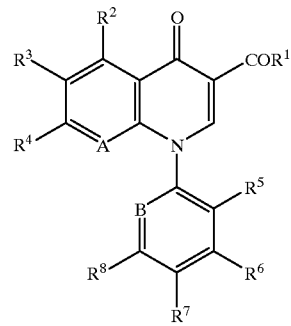

(1)

wherein $R^1$ is —OH, a carboxy-protecting group or (alkyl) amino group, $R^2$ is H, or —NO$_2$, (protected) amino, (protected) hydroxyl, lower alkyl or lower alkoxyl group, $R^3$ is a halogen atom, H, or —NO$_2$, lower alkyl, lower alkoxyl or amino group, $R^4$ is an azido, (substituted) hydrazino, (substituted) amino, lower alkoxyl or hydroxyl group, $R^5$, $R^6$ and $R^7$ are independently H, —NO$_2$, halogen atom or lower alkyl group, $R^8$ is a —NO$_2$, (substituted) amino, —OH or lower alkoxyl group, A is N or C—$R^{12}$, in which $R^{12}$ is H, halogen atom, or (substituted) lower alkyl, lower alkenyl, lower alkynyl, lower alkoxyl, lower alkylthio or nitro group, and B is N or C—$R^{13}$, in which $R^{13}$ is H or halogen atom, or salts thereof, and medicine comprising such a compound as an active ingredient. The derivatives or the salts thereof exhibit excellent antibacterial action and peroral absorbability, scarcely cause side effects, and are easy of synthesis.

3 Claims, No Drawings

PYRIDONECARBOXYLIC ACID DERIVATIVES OR SALTS THEREOF AND DRUGS CONTAINING THE SAME AS THE ACTIVE INGREDIENT

This application is a 371 of PCT/JP 97/04326, filed Nov. 27, 1997.

TECHNICAL FIELD

The present invention relates to novel pyridonecarboxylic acid derivatives or salts thereof which exhibit excellent antibacterial activities and peroral absorbability, and medicines comprising such a compound as an active ingredient.

BACKGROUND ART

Many compounds having a pyridonecarboxylic acid as a basic skeleton are known to be useful as synthetic antibacterial agents because they have excellent antibacterial activities and wide antibacterial spectra. Of these, norfloxacin (Japanese Patent Application Laid-Open No. 141286/1978), enoxacin (Japanese Patent Application Laid-Open No. 31042/1980), ofloxacin (Japanese Patent Application Laid-Open No. 46986/1982), ciprofloxacin (Japanese Patent Application Laid-Open No. 74667/1983), tosufloxacin (Japanese Patent Application Laid-Open No. 228479/1985) and the like are in wide clinical use as agents for treating infectious diseases.

However, these compounds have been not yet sufficient in antibacterial activity, intestinal absorbability, metabolic stability and side effects, particularly, phototoxicity, cytotoxicity, etc. Pyridone-carboxylic acid derivatives carrying cyclic amino group at the 7-position of the naphthyridine skeleton or quinoline skeleton have also been known (WO96/12704). However, It is still desired to develop compounds far excellent in absorbability and easy-to-synthesize.

It is therefore an object of the present invention to provide novel compounds satisfying all respects of antibacterial activity, oral absorbability, metabolic stability and side effects, particularly, phototoxicity, cytotoxicity, etc., and medicines containing such a compound.

DISCLOSURE OF THE INVENTION

In view of the foregoing circumstances, the present inventors have carried out intensive research, synthesized various kinds of compounds and investigated their antibacterial activities, absorbabilities, side effects and the like. As a result, it has been found that specific pyridonecarboxylic acid derivatives satisfy the above-described requirements, thus leading to completion of the present invention.

According to the present invention, there is thus provided a pyridonecarboxylic acid derivative represented by the general formula (1):

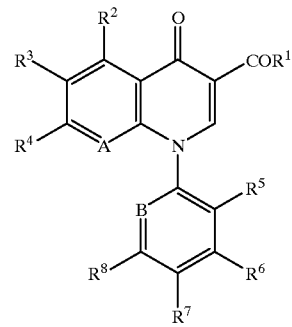

wherein $R_1$ is a group $—OR^9$ (wherein $R^9$ is a hydrogen atom or carboxy-protecting group), amino group or lower alkylamino group, $R^2$ is a hydrogen atom, nitro group, amino or hydroxyl group which may be protected, lower alkyl group, or lower alkoxyl group, $R^3$ is a halogen atom, hydrogen atom, nitro group, lower alkyl group, lower alkoxyl group or amino group, $R^4$ is a nitro group, azido group, hydrazino group which may be substituted, group $—NR^{10}R^{11}$ (wherein $R^{10}$ and $R^{11}$ may be the same or different from each other and are independently a hydrogen atom, lower alkyl group which may be substituted, lower alkenyl group, lower cycloalkyl group, saturated heterocyclic group or amino-protecting group), lower alkoxyl group or hydroxyl group, $R^5$, $R^6$ and R7 may be the same or different from one another and are independently a hydrogen atom, nitro group, halogen atom or lower alkyl group, $R^8$ is a nitro group, amino group which may be substituted, hydroxyl group or lower alkoxyl group, A is a nitrogen atom or group $C—R^{12}$ (wherein $R^{12}$ is a hydrogen atom, halogen atom, lower alkyl group which may be substituted, lower alkenyl group, lower alkynyl group, lower alkoxyl group, lower alkylthio group or nitro group), and B is a nitrogen atom or group $C—R^{13}$ (wherein $R^{13}$ is a hydrogen atom or halogen atom), or a salt thereof.

According to the present invention, there is also provided a medicine comprising the pyridonecarboxylic acid derivative or the salt thereof as an active ingredient.

According to the present invention, there is further provided a medicinal composition comprising the pyridonecarboxylic acid derivative or the salt thereof and a pharmaceutically acceptable carrier.

According to the present invention, there is still further provided use of the pyridonecarloxylic acid derivative or the salt thereof for a medicine.

According to the present invention, there is yet still further provided a method of treating an infectious disease, which comprises administering an effective amount of the pyridonecarboxylic acid derivative or the salt thereof to mammal including the human, Wish or shellfish, or bird.

BEST MODE FOR CARRYING OUT THE INVENTION

The present invention will hereinafter be described in detail. Incidentally, the term "lower" in the substituent groups of the pyridonecarboxylic acid derivatives represented by the general formula (1) means that such a substituent group has 1 to 7 carbon atoms, particularly preferably 1 to 5 carbon atoms in the case where the substituent group is linear. When the substituent group is cyclic on the other hand, it means a substituent group having 3 to 7 carbon atoms.

The carboxy-protecting group represented by $R^9$ in the general formula (1) means an ester residue of a carboxylic ester, and examples thereof include any groups which may be cleaved with comparative ease to produce a free carboxyl group. Specific examples thereof include groups cleaved by a treatment under mild conditions, such as hydrolysis or catalytic reduction, for example, lower alkyl groups such as methyl, ethyl, n-propyl, isopropyl, n-butyl, isobutyl, t-butyl, pentyl, hexyl and heptyl groups; lower alkenyl groups such as vinyl, allyl, 1-propenyl, butenyl, pentenyl, hexenyl and heptenyl groups; aralkyl groups having 7 to 11 carbon atoms, such as a benzyl group; and aryl groups having 7 to 11 carbon atoms, such as phenyl and naphthyl groups; and groups cleaved easily in vivo, for example, lower alkanoyloxy-lower alkyl groups such as acetoxymethyl and pivaloyloxymethyl groups; lower alkoxycarbonyloxy-lower alkyl groups such as methoxycarbonyloxymethyl and 1-ethoxycarbonyloxyethyl groups; lower alkoxy-lower alkyl groups such as a methoxymethyl group; lactonyl groups such as a phthalidyl group; di-lower-alkylamino-lower alkyl groups such as a 2-dimethylaminoethyl group; and a (5-methyl-2-oxo-1,3-dioxol-4-yl)methyl group.

As $R^9$, a hydrogen atom is particularly preferred. The lower alkylamino group represented by $R^1$ means an amino group substituted by one or two of lower alkyl groups having 1 to 7 carbon atoms, such as methyl and ethyl groups, and examples thereof include methylamino, ethylamino, dimethylamino and methylethylamino groups.

A protecting group in the amino or hydroxyl group, which is represented by $R^2$ and may be protected, may be any group so far as it can protect the amino or hydroxyl group from chemical reactions and be cleaved with ease after completion of the desired reaction. Examples thereof include lower alkanoyl groups such as formyl, acetyl, propionyl, pivaloyl and hexanoyl groups; lower alkoxycarbonyl groups such as methoxycarbonyl, ethoxycarbonyl, propoxycarbonyl and t-butoxycarbonyl groups; aroyl groups such as benzoyl, toluoyl and naphthoyl groups; aralkyloxycarbonyl groups such as benzyloxycarbonyl and phenethyloxycarbonyl groups; and aralkyl groups such as benzyl, phenethyl, benzhydryl and trityl groups.

Examples of the lower alkyl group represented by $R^2$ include linear or branched alkyl groups having 1 to 7 carbon atoms, such as methyl, ethyl, n-propyl, isopropyl, n-butyl, isobutyl, t-butyl, pentyl, hexyl, heptyl, 1-ethylpropyl, 1,1-dimethylbutyl, 2,2-dimethylbutyl, 3,3-dimethylbutyl and 2-ethylbutyl groups. Of these, the methyl group is preferred.

Examples of the lower alkoxyl group represented by $R^2$ include linear or branched alkoxyl groups having 1 to 7 carbon atoms, such as methoxy, ethoxy, propoxy, isopropoxy, butoxy and t-butoxy groups. Of these, the methoxy group is preferred.

Examples of the halogen atom represented by $R^3$ include fluorine, chlorine, bromine and iodine atoms. Of these, the fluorine atom is particularly preferred.

Examples of the lower alkyl group represented by $R^3$ include the same groups as those mentioned in $R^2$. Of these, the methyl group is preferred.

Examples of the lower alkoxyl group represented by $R^3$ include the same groups as those mentioned in $R^2$. Of these, those having 1 to 7 carbon atoms, such as methoxy, ethoxy and propoxy groups are preferred, with the methoxy group being particularly preferred.

Examples of the substituent group in the hydrazino group, which is represented by $R^4$ and may be substituted, include lower alkyl groups such as methyl, ethyl, n-propyl, isopropyl, n-butyl, isobutyl, t-butyl, pentyl, hexyl and heptyl groups. A 1-methylhydrazino group is particularly preferred as the hydrazino group which may be substituted.

Examples of the lower alkyl groups which are represented by $R^{10}$ and $R^{11}$ in the group $-NR^{10}R^{11}$ represented by $R^4$ and may be substituted include the same lower alkyl groups as those represented by $R^2$, and lower alkyl groups substituted by one or more of halogen atoms, hydroxyl groups, lower alkoxyl groups and amino groups. The halogen atoms and lower alkoxyl groups referred to here include the same atoms and groups as those respectively mentioned in $R^3$. Preferable examples of the lower alkyl groups which may be substituted include methyl, ethyl, t-butyl, 2-hydroxyethyl, 2-hydroxy-1-methylethyl, 2-hydroxy-n-propyl, 3-hydroxy-n-propyl, 2,3-dihydroxy-n-propyl, 2,2,2-trifluoroethyl, 3,3,3-trifluoro-2-hydroxypropyl, 2-hydroxy-3-methoxypropyl, 3-fluoro-2-hydroxypropyl, methoxyethyl, aminomethyl, aminoethyl, aminopropyl and 2-amino-1-methoxyethyl groups.

Examples of the lower alkenyl groups represented by $R^{10}$ and $R^{11}$ in the group $-NR^{10}R^{11}$ represented by $R^4$ include vinyl, allyl and 1-propenyl groups. Of these, the allyl group is preferred.

Examples of the lower cycloalkyl groups represented by $R^{10}$ and $R^{11}$ in the group $-NR^{10}R^{11}$ represented by $R^4$ include cycloalkyl groups having 3 to 7 carbon atoms, such as cyclopropyl, cyclobutyl, cyclopentyl cyclohexyl and cycloheptyl. Of these, the cyclopropyl group is preferred.

The saturated heterocyclic groups represented by $R^{10}$ and $R^{11}$ in the group $-NR^{10}R^{11}$ represented by $R^4$ mean saturated heterocyclic groups containing at least one nitrogen, oxygen or sulfur atom in their rings and having 2 to 8 carbon atoms. Examples thereof include aziridinyl, azetidinyl, pyrrolidinyl, piperidinyl, piperazinyl, oxetanyl, morpholino, thiomorpholino and oxazolidinyl groups, with the pyrrolidinyl and oxetanyl groups being preferred.

The amino-protecting groups represented by $R^{10}$ and $R^{11}$ in the group $-NR^{10}R^{11}$ represented by $R^4$ may be any groups so far as they can protect the amino group from chemical reactions and be cleaved with ease after completion of the desired reaction. Examples thereof include the same groups as those mentioned in $R^2$.

Examples of the lower alkoxyl group represented by $R^4$ include the same groups as those mentioned in $R^2$, with the methoxy group being preferred.

Preferable examples of the group $-NR^{10}R^{11}$ include amino, methylamino, ethylamino, allylamino, 3-hydroxy-n-propylamino, 2-hydroxyethylamino, 2-hydroxy-n-propylamino and 2-hydroxy-1-methylethylamino groups. Of these, the amino and methylamino groups are particularly preferred.

Examples of the halogen atoms represented by $R^5$, $R^6$ and $R^7$ include the same halogen atoms as those mentioned in $R^3$. Of these, the fluorine and chlorine atoms are preferred, with the fluorine atom being particularly preferred.

Examples of the lower alkyl groups represented by $R^5$, $R^6$ and $R^7$ include the same alkyl groups as those mentioned in $R^2$. Of these, the methyl group is preferred.

The combination of $R^5$, $R^6$ and $R^7$ is preferably a combination that $R^5$ is a hydrogen atom, halogen atom or lower alkyl group, $R^6$ is a hydrogen atom, and $R^7$ is a halogen atom. Of these, a combination that $R^5$ is a hydrogen atom, fluorine atom, chlorine atom or methyl group, $R^6$ is a hydrogen atom, and $R^7$ is a fluorine atom is particularly preferred.

Examples of the substituent group in the amino group, which is represented by $R^6$ and may be substituted, include lower alkyl groups such as methyl, ethyl, n-propyl, isopropyl, n-butyl, isobutyl, t-butyl, pentyl, hexyl and heptyl groups; lower alkenyl groups such as vinyl, allyl, 1-propenyl, butenyl, pentenyl, hexenyl and heptenyl groups; aralkyl groups such as benzyl and 1-phenylethyl groups; aryl groups such as phenyl and naphthyl groups; lower alkanoyl groups such as formyl, acetyl, propionyl, butyryl and isobutyryl groups; lower alkoxycarbonyl groups such as methoxycarbonyl, ethoxycarbonyl and t-butoxy-carbonyl groups; aroyl groups such as benzoyl and naphthoyl groups; and amino acid residues or oligopeptide residues such as glycyl, leucyl, valyl, alanyl, phenylalanyl, alanyl-alanyl, glycyl-valyl and glycyl-glycyl-valyl, and amino acid residues or oligopeptide residues carrying the functional groups which have been protected by a protecting group commonly used in peptide chemistry, such as an acyl or lower aralkyl group. One substituent, or two substituents which may be the same or different from each other may be optionally selected from among these substituent groups. A compound protected by such an amino residue or peptide residue is expected to improve solubility in water.

Preferable examples of the amino group which may be substituted include an amino, lower alkyl amino, di-lower-alkylamino, lower alkanoylamino, amino acid-substituted amino and oligopeptide-substituted amino groups. Preferable examples of $R^8$ include amino, methylamino, ethylamino and dimethylamino groups. Of these, the amino group is particularly preferred.

Examples of the lower alkoxyl group represented by $R^8$ include the same groups as those mentioned in $R^3$. Of these, the methoxy group is preferred.

Examples of the halogen atom or lower alkoxy group represented by $R^{12}$ in the case where A is the group $C-R^{12}$ include the same halogen atoms or alkoxy groups as those mentioned in $R^3$. A chlorine or bromine atom is particularly preferred as the halogen atom, while a methoxy group is particularly preferred as the lower alkoxyl group. Examples of the lower alkyl group which may be substituted, or lower alkenyl group represented by $R^{12}$ include the same lower alkyl or alkenyl groups as those represented by $R^{10}$ and $R^{11}$ in the group $-NR^{10}R^{11}$ represented by $R^4$. Preferable examples of the lower alkyl group which may be substituted include lower alkyl groups substituted by one or more halogen atoms, such as a trifluoromethyl groups, and lower alkyl groups substituted by one or more hydroxyl groups, such as a hydroxymethyl group. Preferable examples of the lower alkenyl group include vinyl and 1-propenyl groups.

Examples of the lower alkynyl group represented by $R^{12}$ include ethynyl, 1-propynyl and 2-propynyl groups. Of these, the ethynyl group is preferred. Examples of the lower alkylthio group include methylthio and ethylthio groups. Of these, the methylthio group is preferred.

Examples of the halogen atom represented by $R^{13}$ in the case where B is the group $C-R^{13}$ include the same halogen atoms as those mentioned in $R^3$.

The compounds represented by the formula (1) have a naphthyridine skeleton in the case where A is a nitrogen atom, or a quinoline skeleton in the case where A is the group $C-R^{12}$. Compounds in which A is C—Cl, C—Br or $C-CH_3$ are particularly preferred.

Preferable combinations of $R^1$, $R^2$, $R^3$, $R^4$, $R^5$, $R^6$, $R^7$, $R^8$, A and B in the general formula (1) are cases where $R^1$ is a hydroxyl group ($R^9$=H); $R^2$ is a hydrogen atom; $R^3$ is a halogen atom; $R^4$ is an amino, lower alkylamino, di-lower-alkylamino or lower alkanoylamino group); $R^5$ and $R^7$ are halogen atoms; $R^6$ is a hydrogen atom; $R^8$ is an amino, lower alkylamino, di-lower-alkylamino or lower alkanoylamino group; A is C—Cl, C—Br or $C-CH_3$; and B is a nitrogen atom or C—H. More preferable combinations are cases where $R^1$ is a hydroxyl group ($R^9$=H); $R^2$ is a hydrogen atom; $R^3$ is a fluorine atom; $R^4$ is an amino or methylamino group; $R^5$ and $R^7$ are fluorine atoms; $R^6$ is a hydrogen atom; $R^8$ is an amino or methylamino group; A is C—Cl, C—Br or $C-CH_3$; and B is a nitrogen atom or C—H.

Salts of the pyridonecarboxylic acid derivatives (1) according to the present invention include both acid-addition salts and base-addition salts, and also chelate salts formed with a boron compound. Examples of the acid-addition salts include (A-1) salts with a mineral acid such as hydrochloric acid or sulfuric acid, (A-2) salts with an organic carboxylic acid such as formic acid, citric acid, trichloroacetic acid, trifluoroacetic acid, fumaric acid or maleic acid, and (A-3) salts with a sulfonic acid such as methanesulfonic acid, benzenesulfonic acid, p-toluenesulfonic acid or naphthalenesulfonic acid. Examples of the base-addition salts include (B-1) salts with an alkali metal such as sodium or potassium, (B-2) salts with an alkaline earth metal such as calcium or magnesium, (B-3) ammonium salts, and (B-4) salts with a nitrogen-containing organic base such as methylamine, trimethylamine, tri-ethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine or N,N'-dibenzylethylenediamine. Examples of the boron compound include boron halides such as boron fluoride, and lower acyloxyborons such as acetoxyboron.

The pyridonecarboxylic acid derivatives (1) or the salts thereof may be present not only in an unsolvated form, but also in the hydrated form or solvated form. However, the compounds according to the present invention include all the compounds of the crystal, hydrate and solvate forms.

The pyridonecarboxylic acid derivatives (1) or the salts thereof may also be present in the form of optically active substances. These optically active substances, racemates and other optical isomer mixtures are also included in the compounds according to the present invention. Further, the compounds (1) may be present in the form of different stereoisomers (cis-form and trans-form), and these stereoisomers are also included in the compounds according to the present invention.

The pyridonecarboxylic acid derivatives (1) or the salts thereof can be prepared in accordance with a process suitably selected from optional processes according to the kinds of the substituents, and the like. An example thereof is as follows:

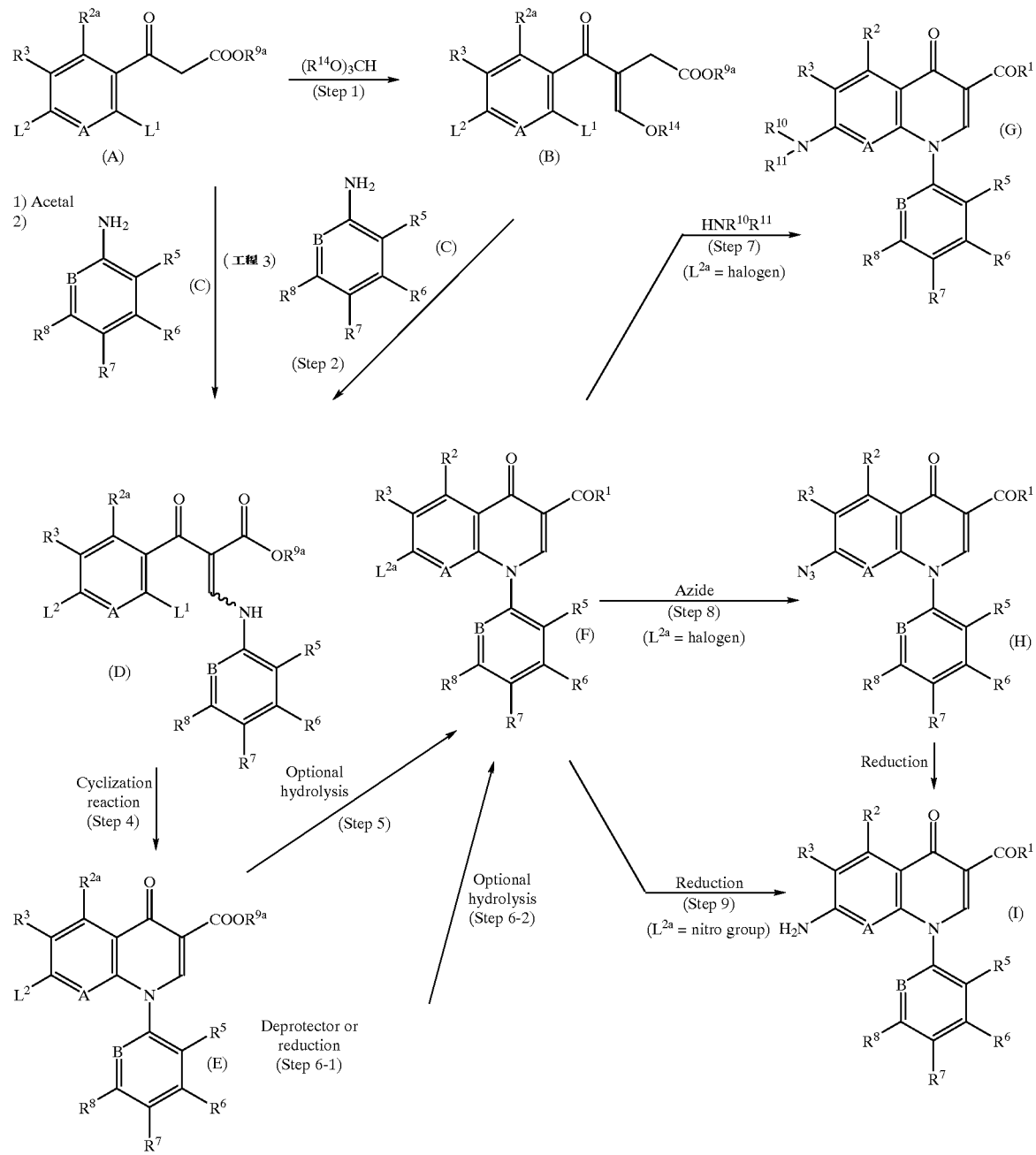

wherein $R^{9a}$ is a carboxy-protecting group, $R^{14}$ is a lower alkyl group, $L^1$ is a halogen atom, $L^2$ is a halogen atom or nitro group, $L^{2a}$ is a halogen atom, nitro group or amino group, $R^{2a}$ is a hydrogen atom, nitro group, protected amino group, protected hydroxyl group or lower alkyl group, and $R^1$, $R^2$, $R^3$, $R^5$, $R^6$, $R^7$, $R^8$, $R^{10}$, $R^{11}$, A and B have the same meanings as defined above.

More specifically, a compound (A) is reacted with an orthoformic ester $[(R^{14}O)_3CH]$ to form an acrylic ester derivative (B) (Step 1). This ester derivative (B) is then reacted with an amino compound (C) to form a compound (D) (Step 2). Alternatively, the compound (A) is reacted with an acetal and then with the amino compound (C) to form the compound (D) (Step 3). The compound (D) is then subjected to a cyclization reaction to form a naphthyridine ring or quinoline ring, thereby obtaining a compound (E) (Step 4). This compound (E) is then optionally hydrolyzed (Step 5), or the protecting group of the protected hydroxyl group or amino group in $R^{2a}$ is deprotected, or the nitro group is reduced (Step 6-1), and the thus-obtained compound is then optionally hydrolyzed (Step 6-2), thereby obtaining a compound (F). A compound in which $L^2$ in the compound (E) is a nitro group, and a compound in which $L^{2a}$ in the compound (F) is a nitro or amino group are included in the compounds according to the present invention. A compound in which $L^{2a}$ in the compound (F) is a halogen atom is then reacted with $HNR^{10}R^{11}$, thereby obtaining a compound (G) according to the present invention, in which $R^4$ in the general formula (1) is a group $—NR^{10}R^{11}$ (Step 7). The same compound is reacted with an azide, thereby obtaining a compound (H) according to the present invention, in which $R^4$ in the general formula (1) is an azido group (Step 8). A compound in which $L^{2a}$ in the compound (F) is a nitro group is reduced (Step 9), or the compound (H) is reduced, thereby obtaining a compound (I) according to the present invention, in which $R^4$ in the general formula (1) is an amino group.
(Step 1)

This step is a step of reacting the compound (A) with the orthoformic ester $[R^{14}O]_3CH$ without using any solvent or in a proper solvent to form the acrylic ester derivative (B).

The orthoformic ester used in this reaction is preferably an ester in which $R^{14}$ is a methyl or ethyl group. The amount of the ester used is preferably at least equimolar to the compound (A), particularly 1 to 10 times by mole as much as the compound (A). It is also preferred that a carboxylic acid anhydride such as acetic anhydride is added as a reaction aid, since a yield is enhanced. The amount of such a reaction aid is preferably at least equimolar to the compound (A), particularly about 1 to 10 times by mole as much as the compound (A). Examples of the solvent used in this reaction include aromatic hydrocarbons such as benzene and toluene. This reaction is generally conducted at 0 to 160° C., preferably 50 to 150° C. for a period of time of generally from 10 minutes to 48 hours, preferably from 1 to 10 hours.
(Step 2)

This step relates to a reaction in which the acrylic ester derivative (B) is reacted with the amino compound (C) without using any solvent or in a proper solvent to form the compound (D).

The amount of the amino compound used is preferably at least equimolar to the acrylic ester derivative (B), particularly 1 to 2 times by mole as much as the derivative (B). Any solvent may be used as the solvent used in this reaction so far as it does not affect the reaction. Examples thereof include aromatic hydrocarbons such as benzene, toluene and xylene; ethers such as diethyl ether, tetrahydrofuran, 1,4-dioxane, monoglyme and diglyme; aliphatic hydrocarbons such as pentane, hexane, heptane and ligroin; halogenated hydrocarbons such as methylene chloride, chloroform and carbon tetrachloride; aprotic polar solvents such as N,N-dimethylformamide and dimethyl sulfoxide; and alcohols such as methanol, ethanol and propanol. This reaction is generally conducted at 0 to 150° C., preferably 0 to 100° C. for a period of time of generally from 10 minutes to 48 hours.
(Step 3)

In this preparation process, a step (Step 3) of reacting the compound (A) with an acetal such as N,N-dimethylformamide dimethyl acetal or N,N-dimethylformamide diethyl acetal and then reacting the reaction product with the amino compound (C) to derive the compound (D) may also be used in place of the above-described Step 1 and Step 2. Any solvent may be used as the solvent used for the reaction with the acetal in this reaction so far as it does not affect the reaction. Specifically, the same solvent as that used in Step 2 may be used. This reaction is generally conducted at 0 to 150° C., preferably room temperature to 100° C. for a period of time of generally from 10 minutes to 48 hours, preferably from 1 to 10 hours.
(Step 4)

This step related to a reaction in which the compound (D) is subjected to a cyclization reaction to form a naphthyridine ring or quinoline ring, thereby obtaining the compound (E).

This reaction is conducted in the presence or absence of a basic compound in a proper solvent. Examples of such a basic compound include alkali metals such as metallic sodium and metallic potassium; metal hydrides such as sodium hydride and calcium hydride; inorganic salts such as sodium hydroxide, potassium hydroxide, sodium carbonate and potassium carbonate; alkoxides such as sodium methoxide, sodium ethoxide and potassium t-butoxide; metal fluorides such as sodium fluoride and potassium fluoride; and organic salts such as triethylamine and 1,8-diazabicyclo[5.4.0]undecene (DBU). The amount used is preferably at least equimolar to the compound (D), particularly about 1 to 2 times by mole as much as the compound (D). Any solvent may be used as the solvent used in this reaction so far as it does not affect the reaction. Examples thereof include aromatic hydrocarbons such as benzene, toluene and xylene; ethers such as diethyl ether, tetrahydrofuran, 1,4-dioxane and monoglyme; halogenated hydrocarbons such as methylene chloride, chloroform and carbon tetrachloride; alcohols such as methanol, ethanol, propanol and butanol; and aprotic polar solvents such as N,N-dimethylformamide and dimethyl sulfoxide. This reaction is generally conducted at 0 to 200° C., preferably room temperature to 180° C. for a period of time of generally from 5 minutes to 24 hours.
(Step 5)

This step is a step of optionally hydrolyzing the compound (E) to separate the carboxy-protecting group represented by $R^{9a}$, thereby obtaining a compound in which $R^2$ in the compound (F) is a hydrogen atom, nitro group, protected amino group or protected hydroxyl group.

To this step, may be applied any reaction conditions used in ordinary hydrolysis reaction. For example, this reaction is conducted in the presence of a basic compound such as sodium hydroxide, potassium hydroxide, sodium carbonate or potassium carbonate; a mineral acid such as hydrochloric acid, sulfuric acid or hydrobromic acid; or an organic acid such as p-toluenesulfonic acid or acetic acid, in a solvent such as water; an alcohol such as methanol, ethanol or propanol; an ether such as tetrahydrofuran or 1,4-dioxane; a ketone such as acetone or methyl ethyl ketone; or acetic acid, or a mixed solvent thereof. This reaction is generally conducted at room temperature to 180° C., preferably room temperature to 140° C. for a period of time of generally from 1 to 24 hours. When $R^8$ in the compound (E) is a protected amino group such as an aralkylamino group or acylamino group, such a protecting group may be separated at the same time in this step.
(Step 6-1) and (Step 6-2)

A compound in which $R^2$ in the compound (F) is an amino group or hydroxyl group can be prepared by (Step 6-1) and (Step 6-2), which will be described in detail subsequently, in place of the above described (Step 5). More specifically, such a compound can be prepared by separating a protecting group from a compound in which $R^{2a}$ in the compound (E) is a protected hydroxyl group or protected amino group, or reducing a nitro group of a compound in which $R^{2a}$ is the nitro group, thereby forming a hydroxyl group or amino group (Step 6-1), and optionally separating the carboxy-protecting group represented by $R^{9a}$ into a hydrogen atom (Step 6-2).
(Step 6-1)

This step is a cleaving step of the hydroxyl-protecting group or amino-protecting group of $R^{2a}$ in the compound (E) or a reducing step of the nitro group represented by $R^{2a}$ into an amino group. Incidentally, when $L^2$ in the compound (E) is a nitro group, this group is also reduced into an amino group in this step.

To this reaction, may be applied any reduction reaction generally used. More specifically, examples of the reduction process include reduction by metal such as zinc, iron, tin, tin (II) chloride or the like in an acid solution; reduction by sulfur compounds such as sodium sulfide, sodium hydrosulfide or sodium dithionite; and catalytic reduction making use of platinum, Raney nickel, platinum-black (Pt-C), palladium-carbon (Pd-C) or the like. Of these, a process making use of iron in an acetic acid solution is preferred. This reaction is generally conducted at 0 to 100° C., preferably room temperature to 50° C. for a period of time of generally from several minutes to 72 hours, preferably from 10 minutes to 24 hours.

When the hydroxyl-protecting group or amino-protecting group is cleaved, hydrolysis under acid conditions may also be used according to the kind (for example, benzyl group) of the protecting group in addition to the above-described reduction reaction. In this case, the reaction can be conducted in the presence of hydrochloric acid, hydrochloric acid/1,4-dioxane, hydrochloric acid/acetic acid, hydrobromic acid, hydrobromic acid/acetic acid, trifluoroacetic acid or the like in a solvent, for example, an ether such tetrahydrofuran or 1,4-dioxane; a halogenated hydrocarbon such as chloroform; water; an alcohol such as methanol; or the like. The reaction temperature is generally from 0 to 100° C., preferably from room temperature to 100° C., and the reaction time is from several minutes to 72 hours, preferably from 3 to 48 hours.

The cleavage (hydrolysis) of the carboxy-protecting group described in the subsequent (Step 6-2) may be conducted at the same time as the cleavage of the protecting group according to the combination of the conditions described here.

(Step 6-2)

This step relates to a reaction in which the carboxy-protecting group represented by $R^{9a}$ in the compound obtained in the above-described (Step 6-1) is cleaved by hydrolysis into a hydrogen atom, thereby forming the compound (F). This reaction can be conducted under the same conditions as the conditions described in (Step 5).

(Step 7)

This step relates to a reaction wherein a compound in which $L^{2a}$ in the compound (F) is a halogen atom is reacted with a compound represented by $HNR^{10}R^{11}$ to obtain the compound (G) according to the present invention, in which $R^4$ in the general formula (1) is a group $-NR^{10}R^{11}$.

In the case where $HNR^{10}R^{11}$ has a free amino group, the amino group may be suitably protected with a proper protecting group before the reaction is conducted, and the deprotection may be conducted after the reaction.

This reaction is conducted at room temperature to 160° C. in a solvent which does not affect the reaction, for example, water, an aromatic hydrocarbon such as benzene, toluene or xylene; an alcohol such as methanol or ethanol; an ether such as tetrahydrofuran, 1,4-dioxane or monoglyme; a halogenated hydrocarbon such as methylene chloride, chloroform or carbon tetrachloride; an aprotic polar solvents such as N,N-dimethylformamide, dimethyl sulfoxide or N-methylpyrrolidone; acetonitrile; or pyridine, in the presence of an acid-neutralizing agent, for example, sodium carbonate, calcium carbonate, sodium hydrogencarbonate, triethylamine, N-methylpyrrolidine or 1,8-diazabicyclo [5.4.0]undecene (DBU) as needed. The reaction time is from several minutes to 48 hours, preferably from 10 minutes to 24 hours. The amount of the compound $HNR^{10}R^{11}$ used is preferably at least equimolar to the compound (F), particularly about 1 to 5 times by mole as much as the compound (F). In the case where $R^1$ is a group $OR^{9a}$ in which $R^{9a}$ is a carboxy-projecting group, the group may be optionally hydrolyzed into a hydroxyl group.

(Step 8)

This step relates to a reaction wherein a compound in which $L^{2a}$ in the compound (F) is a halogen atom is reacted with an azide to obtain the compound (H) according to the present invention, in which $R^4$ in the general formula (1) is an azido group.

Examples of the azide used in this reaction include sodium azide and trimethylsily azide. The reaction is preferably conducted at −20 to 100° C. for 5 minutes to 5 hours in a solvent, for example, N,N-dimethylformamide or the like. The compound (H) thus obtained is optionally subjected to a reduction reaction, whereby the compound can be provided in the form of an amine.

(Step 9)

This step relates to a reaction wherein a compound in which $L^{2a}$ in the compound (F) is a nitro group is directly subjected to a reduction reaction to convert the nitro group into an amino group.

To the reduction, may be applied such a commonly used process as mentioned in (Step 6-1). In particular, the process making use of iron in an acetic acid solution is preferred.

Incidentally, a compound in which $R^9$ in the compound (1) according to the present invention is a hydrogen atom can be converted into a compound (1) according to the present invention, in which $R^9$ is a carboxy-protecting group, in accordance with, for example, the following reaction scheme:

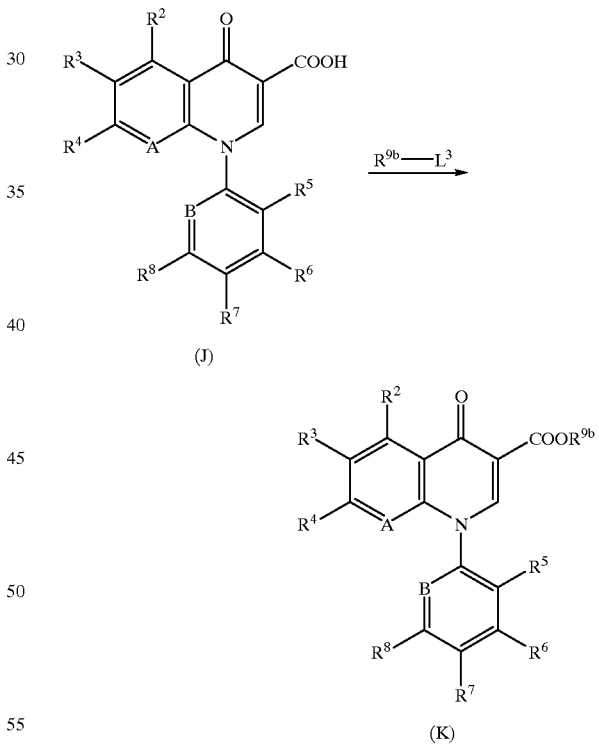

wherein $R^{9b}$ is a carboxy-protecting group, $L^3$ is a halogen atom, and $R^2$, $R^3$, $R^4$, $R^5$, $R^6$, $R^7$, $R^8$, A and B have the same meanings as defined above.

More specifically, a compound (K) according to the present invention is obtained by reacting a compound (J) according to the present invention with a halogen compound ($R^{9b}$—$L^3$). Examples of a solvent used in this reaction include inert solvents, for example, aromatic hydrocarbons such as benzene and toluene; halogenated hydrocarbons such as methylene chloride and chloroform; aprotic polar solvents such as N,N-dimethylformamide and dimethyl sulfoxide; and acetonitrile. The reaction temperature is generally room temperature to about 100° C. This reaction is preferably conducted in the presence of a basic compound such as triethylamine, diisopropylethylamine, dicyclohexylamine, 1,8-diazabicyclo[5.4.0]undecene, sodium carbonate, potassium carbonate or sodium hydroxide, from the viewpoints of yield and the like.

Incidentally, the raw compound (A) can be prepared, for example, in accordance with any of the processes described in the following documents, or a process similar to this process.

(1) J. Heterocyclic Chem., 22, 1033 (1985);
(2) Liebigs Ann. Chem., 29 (1987);
(3) J. Med. Chem., 31, 991 (1988);
(4) J. Org. Chem., 35, 930 (1970);
(5) Japanese Patent Application Laid-Open No. 246541/1987;
(6) Japanese Patent Application Laid-Open No. 262721/1987;
(7) Japanese Patent Application Laid-Open No. 145268/1988;
(8) J. Med. Chem., 29, 2363 (1986);
(9) J. Fluorln Chem., 28, 361 (1985);
(10) Japanese Patent Application Laid-open No. 198664/1988;
(11) Japanese Patent Application Laid-Open No. 264461/1988; and
(12) Japanese Patent Application Laid-Open No. 104974/1963.

The compound (C) can be prepared in accordance with an optional process. It can be prepared by replacement of a halogen atom bonded to a carbon atom making up a 6-membered ring by an amine derivative in accordance with a publicly known halogen-amine substitution reaction described in, for example, WO97/11068 and PCT/JP97/01233.

The compounds according to the present invention obtained in this manner can be isolated and purified in accordance with a method known per se in the art. They are provided in the form of salts, free carboxylic acids or free amines according to conditions for isolation and purification. These compounds are mutually converted, if desired, to prepare the compounds according to the present invention in the intended form.

The compounds (1) according to the present invention or the salts thereof can be formulated as antibacterial agents into compositions together with pharmaceutically acceptable carriers for parenteral administration such as injection administration, intrarectal administration or dropping in the eyes, or for oral administration in a solid or liquid form.

Examples of the preparation form of injection include solutions in pharmaceutically acceptable sterile water, non-aqueous solutions, suspensions and emulsions. Suitable examples of non-aqueous carriers, diluents, solvents or vehicles include propylene glycol, polyethylene glycol, vegetable oils such as olive oil, and injectable organic esters such as ethyl oleate. In such compositions, may be incorporated auxiliaries such as an antiseptic, wetting agent, emulsifier and dispersing agent. These compositions can be sterilized by filtration through a bacterial filter, or mixing a sterilizing agent right before use or mixing a sterilizing agent in the form of a sterile solid composition soluble in another medium sterilely injectable.

In the case of a preparation for dropping in the eyes, a dissolution aid, preservative, isotonicity agent, thickener and the like may preferably be added in addition to the compound according to the present invention.

Examples of solid preparations for oral administration include capsules, tablets, pills, powder and granules. Upon the formulation of such a solid preparation, the compound according to the present invention is mixed with at least one inert diluent, for example, sucrose, lactose or starch. In the general formulation of the solid preparation, other additives, for example, a lubricant such as magnesium stearate may be incorporated into this preparation in addition to the inert diluent. In the cases of the capsules, tablets and pills, a buffer may also be additionally used. The tablets and pills may be coated with an enterally soluble coating.

Examples of liquid preparations for oral administration include pharmaceutically acceptable emulsions, solutions, suspensions, syrups and elixirs containing an inert diluent commonly used by those skilled in the art, for example, water. In such compositions, may also be incorporated auxiliaries, for example, a wetting agent, emulsifier and suspending agent, as well as a sweet corrigent, taste corrigent and smell corrigent.

A preparation for intrarectal administration may preferably contain an excipient, for example, cacao butter or suppository wax, in addition to the compound according to the present invention.

The dose of the compound (1) according to the present invention or the salt thereof depends on the properties of a compound administered, the administration route thereof, desired treatment time, and other factors. However, it is preferred to administer the compound in a dose of generally 0.1 to 1,000 mg/kg, particularly, 0.5 to 100 mg/kg a day for an adult. This amount of the compound may also be administered in 2 to 4 portions a day.

The compounds (1) according to the present invention and the salts thereof exhibit an extremely high antibacterial effect, and low phototoxicity and cytotoxicity, and thus can be widely used as medicines for preventing or treating infectious diseases of the human and animals, medicines for fish' diseases, agricultural chemicals, and food preservatives. The compounds according to the present invention are expected to have an antiviral action, particularly, anti-HIV (human immunodeficiency virus) action and are hence considered to be effective for the prevention or treatment of AIDS.

EXAMPLES

The present invention will hereinafter be described in more detail by the following Examples and Referential Examples. However, the present invention is not limited to these examples.

Referential Example 1

Synthesis of Methyl 2,5-Difluoro-3-methyl-4-nitrobenzoate

Trifluoroacetic acid (50 ml), acetic acid (50 ml) and sodium perborate tetrahydrate (26.6 g) were added to methyl 4-amino-2,5-difluoro-3-methylbenzoate (7.5 g), and the mixture was stirred at 60° C. for 24 hours. Impurities in the reaction mixture was removed by filtration, chloroform was added to the resultant filtrate, and the resultant mixture was washed with water. After an organic layer was dried over anhydrous magnesium sulfate, the solvent was distilled off under reduced pressure to obtain the title compound (6.1 g) as a reddish brown oil.

$^1$H-NMR (CDCl$_3$) δ: 2.34(d,J=3 Hz,3H), 3.98(s,3H), 7.68 (dd,J=6 Hz,J=9 Hz,1H).

Referential Example 2

Synthesis of 2,5-Difluoro-3-methyl-4-nitrobenzoic Acid

Concentrated hydrochloric acid (15 ml) and acetic acid (5 ml) were added to methyl 2,5-difluoro-3-methyl-4- nitrobenzoate (9.1 g), and the mixture was heated under reflux for 3 hours. After the reaction mixture was cooled back to room temperature, water was added to conduct extraction with diethyl ether. After an organic layer was dried over anhydrous magnesium sulfate, the solvent was distilled off under reduced pressure to obtain the title compound (6.1 g) as a brown oil.

$^1$H-NMR (CDCl$_3$) δ: 2.37(d,J=3 Hz,3H), 7.75(m,1H).

Referential Example 3

Synthesis of Ethyl 2,5-Difluoro-3methyl-4-nitrobenzoylacetate:

Magnesium (733 mg), ethanol (3 mg) and carbon tetrachloride (0.1 ml) were stirred at room temperature in a three necked flask to activate them. A solution of ethyl malonate (4.5 ml) in tetrahydrofuran (20 ml) was slowly added dropwise to the activated mixture, followed by stirring at 80° C. for 4 hours. After the reaction mixture was cooled back to room temperature, it was chilled to −40° C. Oxalyl chloride (2.5 ml) and N,N-dimethylformamide (3 drops) were added to a solution of 2,5-difluoro-3-methyl-4-nitrobenzoic acid (6.1 g) in methylene chloride (10 ml). After the mixture was stirred at room temperature for 2 hours, the solvent was distilled off under reduced pressure. Toluene was added to the residue to conduct azeotropic distillation. The residue wets dissolved in tetrahydrofuran (15 ml), and the solution was slowly added dropwise at −40° C. to the reaction mixture obtained previously. After completion of the addition, the temperature of the reaction mixture was given back to room temperature to conduct stirring overnight. After the solvent was distilled off under reduced pressure, concentrated hydrochloric acid (5 ml) was added to the residue to keep its pH at about 2. The residue was then extracted with chloroform, and the solvent was distilled off under reduced pressure. Water (20 ml) and p-toluenesulfonic acid monohydrate (250 mg) were added to the resultant residue, and the mixture was heated under reflux for 5.5 hours. After the reaction mixture was cooled back to room temperature, water was added to the reaction mixture to conduct extraction with chloroform. After an organic layer was dried over anhydrous magnesium sulfate, the solvent was distilled off under reduced pressure. The residue was subjected to column chromatography on silica gel (eluent; ethyl acetate:hexane=1:7) to obtain the title compound (6.0 g) as a red oil.

Example 1

Synthesis of Ethyl 1-(5-Tert-butoxycarbonylamino-2,4-difluorophenyl)-6-fluoro-8-methyl-7-nitro-4-oxo-1,4-dihydroquinoline-3-carboxylate:

Acetic anhydride (13.7 g) and triethyl orthoformate (5.1 g) were added to ethyl 2,5-difluoro-3-methyl-4-nitrobenzoylacetate (6.0 g), and the mixture was heated under reflux for 3 hours. After the reaction mixture was cooled back to room temperature, excess reagents were distilled off under reduced pressure. Toluene was additionally added to the residue to conduct azeotropic distillation. Ethanol (10 ml) was added to a third of the resultant residue, and a solution of N-tert-butoxycarbonyl-2,4-difluoro-m-phenylenediamine (1.7 g) in ethanol (10 ml) was added dropwise to the resultant mixture, followed by stirring at room temperature for 30 minutes. The solvent was distilled off under reduced pressure to obtain a yellow solid (1.8 g). The thus-obtained compound (1.8 g) and potassium carbonate (900 mg) were added to N,N-dimethylformamide (10 ml), and the mixture was stirred at 50° C. for 0.5 hours. Ethyl acetate was added to the reaction mixture, and the resultant mixture was washed with water. After an organic layer was dried over anhydrous magnesium sulfate, the solvent was distilled off under reduced pressure. Ethanol was added to the residue, and solids were collected by filtration to obtain the title compound (760 mg) as a pale yellow powder.

Melting point: 198–199° C.

$^1$H-NMR (CDCl$_3$) δ: 1.41(t,J=7 Hz,3H), 1.52(s,9H), 1.85 (s,3H), 4.41(q,J=7 Hz,2H), 6.84(brs,1H), 7.13(t,J=10 Hz,1H), 8.39(m,3H).

Example 2

Synthesis of Ethyl 1-(6-Tert-butylamino-3,5-difluoropyridin-2-yl)-6-fluoro-8-methyl-7-nitro-4-oxo-1,4-dihydroquinoline-3-carboxylate Acetic anhydride (13.7 g) and triethyl orthoformate (5.1 g) were added to ethyl 2,5-difluoro-3-methyl-4-nitrobenzoylacetate (6.0 g), and the mixture was heated under reflux for 3 hours. After the reaction mixture was cooled back to room temperature, excess reagents were distilled off under reduced pressure. Toluene was additionally added to the residue to conduct azeotropic distillation. Ethanol (10 ml) was added to a third of the residue, and a solution of 2-amino-6-tert-butylamino-3,5-diflouropyridine (1.4 g) in ethanol (10 ml) was added dropwise to the resultant mixture, followed by stirring at room temperature for 20 minutes. The solvent was distilled off under reduced pressure to obtain a light brown oil. The thus-obtained compound and potassium carbonate (970 mg) were added to N,N-dimethylformamide (10 ml), and the mixture was stirred at 70° C. for 3 hours. Ethyl acetate was added to the reaction mixture, and the resultant mixture was washed with water. After an organic layer was dried over anhydrous magnesium sulfate, the solvent was distilled off under reduced pressure. The residue was subjected to column chromatography on silica gel (eluent; ethyl acetate:hexane= 1:4) to obtain the title compound (260 mg) as a pale yellow powder.

Melting point: 194–197° C.

$^1$H-NMR (CDCl$_3$) δ: 1.41(m,12H), 1.86(s,3H), 4.41(q, J=7 Hz,2H), 4.78(brs,1H), 7.26(t,J=9 Hz,1H), 8.28(d,J=9 Hz,1H), 8.59(s,1H).

Example 3

Synthesis of Ethyl 7-Benzylamino-1-(5-tert-butoxycarbonylamino-2,4-difluorophenyl)-8-chloro-6-fluoro-4-oxo-1,4-dihydroquinoline-3-carboxylate Benzylamine (750 mg) and ethyl 1-(5-tert-butoxycarbonylamino-2,4-difluorophenyl)-8-chloro-6,7-difluoro-4-oxo-1,4-dihydroquinoline-3-carboxylate (4,200 mg) were added to a solution of N-methylpyrrolidine (800 mg) and N,N-dimethylformamide (20 ml), and the mixture was stirred overnight at 80° C. After the reaction mixture was cooled to room temperature, ethyl acetate (100 ml) was added to the reaction mixture, and the resultant mixture was washed 3 times with water (100 ml). After an organic layer was dried over anhydrous magnesium sulfate, the solvent was distilled off under reduced pressure. The residue was subjected to column chromatography on silica gel (eluent; chloroform) to obtain the title compound (3,200 mg) as an amorphous substance.

$^1$H-NMR (CDCl$_3$) δ: 1.39(t,J=7 Hz,3H), 1.51(s,9H), 4.37 (q,J=7 Hz,2H), 4.69(s,2H), 4.88(brs,1H), 7.02(t,J=10 Hz,1H), 7.30(m,5H), 8.11(d,J=14 Hz,1H), 8.24(s,1H), 8.26 (m,1H).

Example 4

Synthesis of Ethyl 7-Azido-1-(5-tert-butoxycarbonylamino-2,4-difluorophenyl)-8-chloro-6-fluoro-4-oxo-1,4-dihydroquinoline-3-carboxylate Ethyl 1-(5-tert-butoxycarbonylamino-2,4-difluorophenyl)-8-chloro-6,7-difluoro-4-oxo-1,4-dihydroquinoline-3-carboxylate (1,545 mg) and sodium azide (230 mg) were added to N,N-dimethylformamide (20 ml), and the mixture was stirred overnight at 60° C. After the reaction mixture was cooled back to room temperature, ethyl acetate (100 ml) was added to the reaction mixture, and the resultant mixture was washed 3 times with water (100 ml). After an organic layer was dried over anhydrous magnesium sulfate, the solvent was distilled off under reduced pressure to obtain the title compound (1,280 mg) as an amorphous substance.

$^1$H-NMR (CDCl$_3$) δ: 1.39(t,J=7 Hz,3H), 1.51(s,9H), 4.38 (q,J=7 Hz,2H), 6.80(s,1H), 7.04(t,J=9 Hz,1H), 8.28(m,2H), 8.30(d,J=13 Hz,1H).

Example 5
Synthesis of Ethyl 7-Azido-8-bromo-1-(5-tert-butoxycarbonylamino-2,4-difluorophenyl)-6-fluoro-4-oxo-1,4-dihydroquinoline-3-carboxylate Ethyl 8-bromo-1-(5-tert-butoxycarbonylamino-2,4-difluorophenyl)-6,7-difluoro-4-oxo-1,4-dihydroquinoline-3-carboxylate (1,000 mg) and sodium azide (180 mg) were added to N,N-dimethylformamide (20 ml), and the mixture was stirred overnight at 60° C. After the reaction mixture was cooled back to room temperature, ethyl acetate (100 ml) was added to the reaction mixture, and the resultant mixture was washed 3 times with water (100 ml). After an organic layer was dried over anhydrous magnesium sulfate, the solvent was distilled off under reduced pressure to obtain the title compound (428 mg) as an amorphous substance.

$^1$H-NMR (CDCl$_3$) δ: 1.39(t,J=7 Hz,3H), 1.51(s,9H), 4.38 (q,J=7 Hz,2H), 6.82(s,1H), 7.04(t,J=10 Hz,1H), 8.26(m,1H), 8.29(d,J=11 Hz,1H), 8.36(s,1H).

Example 6
Synthesis of Ethyl 7-Amino-1-(5-tert-butoxycarbonylamino-2,4-difluorophenyl)-6-fluoro-8-methyl-4-oxo-1,4-dihydroquinoline-3-carboxylate Acetic acid (5 ml) and iron powder (180 mg) were added to ethyl 1-(5-tert-butoxycarbonylamino-2,4-difluorophenyl)-6-fluoro-8-methyl-7-nitro-4-oxo-1,4-dihydroquinoline-3-carboxylate (200 mg), and the mixture was stirred at 80° C. for 20 minutes. After the catalyst in the reaction mixture was removed by filtration through Celite, the solvent was distilled off under reduced pressure. The residue was subjected to column chromatography on silica gel (eluent; ethyl acetate:hexane=1:4) to obtain the title compound (170 mg) as an oil.

$^1$H-NMR (CDCl$_3$) δ: 1.41(t,J=7 Hz,3H), 1.51(s,9H), 1.69 (s,3H), 4.20(brs,2H), 4.41(q,J=7 Hz,2H), 6.78(brs,1H), 7.09 (t,J=9 Hz,1H), 8.08(d,J=10 Hz,1H), 8.24(m,1H), 8.29(s,1H).

Example 7
Synthesis of Ethyl 7-Amino-1-(6-tert-butylamino-3,5-difluoropyridin-2-yl)-6-fluoro-8-methyl-4-oxo-1,4-dihydroquinoline-3-carboxylate Acetic acid (5 ml) and iron powder (180 mg) were added to ethyl 1-(6-tert-butylamino-3,5-difluoropyridin-2-yl)-6-fluoro-8-methyl-7-nitro-4-oxo-1,4-dihydroquinoline-3-carboxylate (200 mg), and the mixture was stirred at 80° C. for 20 minutes. After the catalyst in the reaction mixture was removed by filtration through Celite, the solvent was distilled off under reduced pressure. The residue was subjected to column chromatography on silica gel (eluent; ethyl acetate:hexane=1:4) to obtain the title compound (190 mg) as an oil.

Example 8
Synthesis of Ethyl 7-Amino-1-(5-tert-butoxycarbonylamino-2,4-difluorophenyl)-8-chloro-6-fluoro-4-oxo-1,4-dihydroquinoline-3-carboxylate Ethyl 7-benzylamino-1-(5-tert-butoxycarbonylamino-2,4-difluorophenyl)-8-chloro-6-fluoro-4-oxo-1,4-dihydroquinoline-3-carboxylate (3.2 g) was dissolved in 1,2-dichloroethane (40 ml). An acetic acid suspension (10 ml) of 20% palladium hydroxide (300 mg) was added to this solution, and the mixture was stirred overnight at 60° C. in a hydrogen atmosphere. An acetic acid suspension (4 ml) of 20% palladium hydroxide (100 mg) was additionally added, and the resultant mixture was stirred overnight at the same temperature. After the reaction mixture was cooled back to room temperature, palladium hydroxide was removed by filtration. After the solvent was distilled off under reduced pressure, diisopropyl ether was added to the residue, and solids were collected by filtration to obtain the title compound (2.5 g) as an amorphous substance.

$^1$H-NMR (CDCl$_3$) δ: 1.39(t,J=7 Hz,3H), 1.51(s,9H), 4.38 (q,J=7 Hz,2H), 4.72(s,2H), 6.80(s,1H), 7.04(t,J=9 Hz,1H), 8.15(d,J=11 Hz,1H), 8.25(s,1H), 8.30(m,1H).

Example 9
Synthesis of Ethyl 7-Amino-1-(5-tert-butoxycarbonylamino-2,4-difluorophenyl)-8-chloro-6-fluoro-4-oxo-1,4-dihydroquinoline-3-carboxylate Ethyl 7-azido-1-(5-tert-butoxycartbonylamino-2,4-difluorophenyl)-8-chloro-6-fluoro-4-oxo-1,4-dihydroquinoline-3-carboxylate (1.0 g) was dissolved in methanol (15 ml). An acetic acid suspension (4 ml) of 20% palladium hydroxide (200 mg) was added to this solutions and the mixture was stirred at room temperature for 2 hours in a hydrogen atmosphere. After palladium hydroxide was removed by filtration, the solvent was distilled off under reduced pressure. The residue was subjected to column chromatography on silica gel (eluent; chloroform) to obtain the title compound (850 mg) as a colorless powder.

Melting point: 143–150° C.

$^1$H-NMR (CDCl$_3$) δ: 1.39(t,J=7 Hz,3H), 1.51(s,9H), 4.38 (q,J=7 Hz,2H), 4.72(s,2H), 6.80(s,1H), 7.04(t,J=9 Hz,1H), 8.15(d,J=11 Hz,1H), 8.25(s,1H), 8.33(m,1H).

Example 10
Synthesis of Ethyl 7-Amino-8-bromo-1-(5-tert-butoxycarbonylamino-2,4-difluorophenyl)-6-fluoro-4-oxo-1,4-dihydroquinoline-3-carboxylate Ethyl 7-azido-8-bromo-1-(5-tert-butoxycarbonylamino-2,4-difluorophenyl)-6-fluoro-4-oxo-1,4-dihydroquinoline-3-carboxylate (650 mg) was dissolved in methanol (20 ml). An acetic acid suspension (3 ml) of 20% palladium hydroxide (100 mg) was added to this solution, and the mixture was stirred at room temperature for 3 hours in a hydrogen atmosphere. After palladium hydroxide was removed by filtration, the solvent was distilled off under reduced pressure. The residue was subjected to column chromatography on silica gel (eluent; chloroform) to obtain the title compound (423 mg) as a liver-colored amorphous substance.

$^1$H-NMR (CDCl$_3$) δ: 1.39(t,J=7 Hz,3H), 1.51(s,9H), 4.38 (q,J=7 Hz,2H), 4.89(s,2H), 6.80(s,1H), 7.05(t,J=9 Hz,1H), 8.19(d,J=11 Hz,1H), 8.28(s,$_1$H).

Example 11
Synthesis of 7-Amino-1-(5-amino-2,4-difluorophenyl)-8-chloro-6-fluoro-4-oxo-1,4-dihydroquinoline-3-carboxylic Acid Ethyl 7-amino-1-(5-tert-butoxycarbonylamino-2,4-difluorophenyl)-8-chloro-6-fluoro-4-oxo-1,4-dihydroquinoline-3-carboxylate was dissolved in a mixed liquid of acetic acid (10 ml) and 2N hydrochloric acid (8 ml), and the solution was stirred at 100° C. for 2 hours. After the solution was cooled back to room temperature, the solvent was distilled off under reduced pressure. The residue was washed with ethanol and then dissolved in N,N-dimethylformamide (3 ml). Ethanol (3 ml) was further added to the solution, and the mixture was left to stand overnight at room temperature. Crystals deposited were collected by filtration and washed with ethanol to obtain the title compound (740 mg) as colorless crystals.

Melting point: >270° C. (decomposed).

$^1$H-NMR (d$^6$-DMSO) δ: 7.00(m,3H), 7.39(t,J=10 Hz,1H), 7.96(d,J=11 Hz,1H), 8.46(s,1H).

Example 12

Synthesis of 7-Amino-1-(5-amino-2,4-difluorophenyl)-6-fluoro-8-methyl-4-oxo-1,4-dihydroquinoline-3-carboxylic Acid Concentrated hydrochloric acid (2 ml) was added to ethyl 7-amino-1-(5-tert-butoxycarbonylamino-2,4-difluorophenyl)-6-fluoro-8-methyl-4-oxo-1,4-dihydroquinoline-3-carboxylate (170 mg), and the mixture was heated under reflux for 5 hours. After the reaction mixture was cooled back to room temperature, water (2 ml) was added thereto. Solids deposited were collected by filtration and then washed successively with water, ethanol and diethyl ether to obtain the title compound (68 mg) as a pale yellow powder.

Melting point: >276° C. (decomposed).

$^1$H-NMR (d$^6$-DMSO) δ: 1.65(s,3H), 6.49(brs,2H), 6.97 (t,J=9 Hz,1H), 7.44(t,J=10 Hz,1H), 7.84(d,J=11 Hz,1H), 8.45(s,1H).

Example 13

Synthesis of 7-Amino-1-(6-amino-3,5-difluoropyridin-2-yl)-6-fluoro-8-methyl-4-oxo-1,4-dihydoquinoline-3-carboxylic Acid Concentrated hydrochloric acid (2 ml) was added to ethyl 7-amino-1-(6-tert-butylamino-3,5-difluoropyridin-2-yl)-6-fluoro-8-methyl-4-oxo-1,4-dihydroquinoline-3-carboxylate, and the mixture was heated under reflux for 5 hours. After the reaction mixture was cooled back to room temperature, water (2 ml) was added thereto. Solids deposited were collected by filtration and washed successively with water, ethanol and diethyl ether to obtain the title compound (72 mg) as a pale yellow powder.

Melting point: >280° C.

$^1$H-NMR (d$^6$-DMSO) δ: 1.63(s,3H), 6.53(brs,2H), 6.87 (brs,2H), 7.83(d,J=11 Hz,1H), 7.99(t,J=9 Hz,1H), 8.67(s,1H).

Example 14

Synthesis of 1-(5-Amino-2,4-difluorophenyl)-8-chloro-6-fluoro-7-methylamino-4-oxo-1,4-dihydroquinoline-3-carboxylic Acid A 40% aqueous solution (100 mg) of methylamine and 1-(5-amino-2,4-difluorophenyl)-8-chloro-6,7-difluoro-4-oxo-1,4-dihydroquinoline-3-carboxylic acid (100 mg) were added to pyridine (2 ml), and the mixture was stirred at room temperature for 2 hours. After the solvent was distilled off under reduced pressure, ethanol was added to the residue, and the mixture was left to stand overnight. Solids deposited were collected by filtration to obtain the title compound (40 mg) as a colorless powder.

Melting point: 170–173° C.

$^1$H-NMR (d$^6$-DMSO) δ: 3.13(m,3H), 5.45(s,2H), 6.66(s, 1H), 6.97(dd,J=8 Hz,J=9 Hz,1H), 7.38(t,J=10 Hz,1H), 7.96 (d,J=14 Hz,1H), 8.45(s,1H).

Example 15

Synthesis of 1-(5-Amino-2,4-difluorophenyl)-8-bromo-6-fluoro-7-methylamino-4-oxo-1,4-dihydroquinoline-3-carboxylic Acid A 40% aqueous solution (150 mg) of methylamine and 1-(5-amino-2,4-difluorophenyl)-8-bromo-6,7-difluoro-4-oxo-1,4-dihydroquinoline-3-carboxylic acid (150 mg) were added to pyridine (3 ml), and the mixture was stirred at room temperature for 2 hours. After the solvent was distilled off under reduced pressure, a mixed liquid of ethanol and diethyl ether was added to the residue, and solids were collected by filtration to obtain the title compound (40 mg) as a light brown powder.

Melting point: 181–185° C.

$^1$H-NMR (d$^6$-DMSO) δ: 3.21(m,3H), 5.49(s,2H), 6.50(m, 2H), 6.90(m,1H), 7.38(m,1H), 7.99(d,J=15 Hz,1H), 8.45(s, 1H).

Example 16

Synthesis of 1-(5-Amino-2,4-difluorophenyl)-6-fluoro-8-methyl-7-methylamino-4-oxo-1,4-dihydroquinoline-3-carboxylic Acid Pyridine (200 mg) and a 40% aqueous solution (250 mg) of methylamine were added to 1(5-amino-2,4-difluorophenyl)-6,7-difluoro-8-methyl-4-oxo-1,4-dihydroquinoline-3-carboxylic acid (100 mg), arid the mixture was heated and stirred overnight at 70° C. After the solvent was distilled off under reduced pressure, and ethanol (2 ml) and acetic acid (1 drop) were added to the residue to stir the mixture, solids deposited were collected by filtration and washed successively with ethanol and diethyl ether to obtain the title compound (51 mg) as a pale brown powder.

Melting point: 225–228° C.

$^1$H-NMR (d$^6$-DMSO) δ: 1.86(s,3H), 3.02(m,3H), 5.49 (brs,2H), 6.09(brs.1H), 6.95(t,J=9 Hz,1H), 7.44(t,J=11 Hz,1H), 7.83(d,J=14 Hz,1H), 8.47(s,1H).

Example 17

Synthesis of 1-(5-Amino-2,4-difluorophenyl)-6-fluoro-7-methylamino-8-nitro-4-oxo-1,4-dihydroquinoline-3-carboxylic Acid Methylamine Salt 1-(5-Amino-2,4-difluorophenyl)-6,7-difluoro-8-nitro-4-oxo-1,4-dihydroquinoline-3-carboxylic acid (200 mg) and a 40% aqueous solution (172 mg) of methylamine were added to pyridine (1 ml), and the mixture was stirred overnight at room temperature. The solvent was distilled off under reduced pressure, and ethanol was added to the residue to collect solids by filtration. The solids were washed successively with ethanol and diethyl ether to obtain the title compound (122 mg) as an orange powder.

Melting point: 270–274° C. (decomposed).

$^1$H-NMR (d$^6$-DMSO) δ: 2.33(s,3H), 2.97(m,3H), 5.36(s, 2H), 6.74(t,J=9 Hz,1H), 7.31(t,J=11 Hz,1H), 7.95(t,J=14 Hz,1H), 8.06(s,1H).

Example 18

Synthesis of 1-(5-Amino-2,4-difluorophenyl)-6-fluoro-5-methyl-7-methylamino-4-oxo-1,4-dihydroquinoline-3-carboxylic Acid 1-(5-Amino-2,4-difluorophenyl)-6,7-difluoro-5-methyl-4-oxo-1,4-dihydroquinoline-3-carboxylic acid (200 mg) and a 40% aqueous solution (210 mg) of methylamine were added to pyridine (1 ml), and the mixture was heated and stirred overnight at 60° C. After the reaction mixture was allowed to cool, the solvent was distilled off under reduced pressure. Ethanol was added to the residue to collect solids. The solids were washed successively with ethanol and diethyl ether to obtain the title compound (115 mg) as a colorless powder.

Melting point: >270° C.

$^1$H-NMR (d$^6$-DMSO) δ: 2.59(s,3H), 2.76(s,3H), 5.53(s, 2H), 5.81(d,J=8 Hz,1H), 7.01(m,1H), 7.12(brs.1H), 7.50(t, J=10 Hz,1H), 8.54(s,1H).

Example 19
Synthesis of 1-(5-Amino-2-chloro-4-fluorophenyl)-8-chloro-6-fluoro-7-methylamino-4-oxo-1,4-dihydroquinoline-3-carboxylic Acid A 40% aqueous solution (100 mg) of methylamine and 1-(5-amino-2-chloro-4-fluorophenyl)-8-chloro-6,7-difluoro-4-oxo-1,4-dihydroquinoline-3-carboxylic acid (100 mg) were added to pyridine (2 ml), and the mixture was stirred at room temperature for 2 hours. After the solvent was distilled off under reduced pressure, ethanol was added to the residue, and solids were collected by filtration to obtain the title compound (46 mg) as pale yellow crystals.

Melting point: 273° C.

$^1$H-NMR (d$^6$-DMSO) δ: 3.16(m,3H), 5.79(s,2H), 6.67 (brs,1H), 7.02(d,J=9 Hz,1H), 7.48(d,J=11 Hz,1H), 7.97(d, J=14 Hz,1H), 8.36(s,1H).

Example 20
Synthesis of 1-(5-Amino-2-bromo-4-fluorophenyl)-8-chloro-6-fluoro-7-methylamino-4-oxo-1,4-dihydroquinoline-3-carboxylic Acid A 40% aqueous solution (60 mg) of methylamine and 1-(5-amino-2-bromo-4-fluorophenyl)-8-chloro-6,7-difluoro-4-oxo-1,4-dihydroquinoline-3-carboxylic acid (60 mg) were added to pyridine (2 ml), and the mixture was stirred at room temperature for 2 hours. After the solvent was distilled off under reduced pressure, a mixed liquid of ethanol and diethyl ether was added to the residue, and solids were collected by filtration to obtain the title compound (46 mg) as a pale brown powder.

Melting point: >280° C.

$^1$H-NMR (d$^6$-DMSO) δ: 3.46(m,3H), 6.14(s,2H), 6.99 (brs,1H), 7.37(d,J=8 Hz,1H), 7.89(d,J=11 Hz,1H), 8.30(d, J=14 Hz,1H), 8.65(s,1H).

Example 21
Synthesis of 1-(5-Amino-4-fluoro-2-methylphenyl)-8-chloro-6-fluoro-7-methylamino-4-oxo-1,4-dihydroquinoline-3-carboxylic Acid A 40% aqueous solution (100 mg) of methylamine and 1-(5-amino-4-fluoro-2-methylphenyl)-8-chloro-6,7-difluoro-4-oxo-1,4-dihydroquinoline-3-carboxylic acid (100 mg) were added to pyridine (2 ml), and the mixture was stirred at room temperature for 2 hours. After the solvent was distilled off under reduced pressure, a mixed liquid of ethanol and diethyl ether was added to the residue, and the mixture was left to stand overnight. Solids deposited were collected by filtration to obtain the title compound (63 mg) as colorless crystals.

Melting point: 239° C.

$^1$H-NMR (d$^6$-DMSO) δ: 1.84(s,3H), 3.13(m,3H), 5.37(s, 2H), 6.60(m,1H), 6.79(m,1H), 7.08(d,J=13 Hz,1H), 7.97(d, J=14 Hz,1H), 8.28(s,1H).

Example 22
Synthesis of 8-chloro-6-fluoro-1-(2,4-difluoro-5-methylaminophenyl)-7-methylamino-4-oxo-1,4-dihydroquinoline-3-carboxylic Acid Methylamine Salt 8-Chloro-6,7-difluoro-1-(2,4-difluoro-5-methylaminophenyl)-4-oxo-1,4-dihydroquinoline-3-carboxylic acid (200 mg) and a 40% aqueous solution (220 mg) of methylamine were added to pyridine (600 mg), and the mixture was stirred at room temperature for 5 hours. After the solvent was distilled off under reduced pressure, ethanol (1 ml) was added to the residue, and the mixture was stirred for 30 minutes. Deposits were collected by filtration and washed successively with ethanol and diisopropyl ether to obtain the title compound (92 mg) as a colorless powder.

Melting point: 255–258° C.

$^1$H-NMR (d$^6$-DMSO) δ: 2.67(d,J=5 Hz,3H), 3.09(m,3H), 5.86(m,1H), 6.34(brs,1H), 6.91(t,J=8 Hz,1H), 7.37(t,J=11 Hz,1H), 7.89(d,J=14 Hz,1H), 8.23(s,1H).

Example 23
Synthesis of 8-Chloro-6-fluoro-1-(2,4-difluoro-3-methylaminophenyl)-7-methylamino-4-oxo-1,4-dihydroquinoline-3-carboxylic Acid 8-Chloro-6,7-difluoro-1-(2,4-difluoro-3-methylaminophenyl)-4-oxo-1,4-dihydroquinoline-3-carboxylic acid (120 mg) and a 40% aqueous solution (120 mg) of methylamine were added to pyridine (500 mg), and the mixture was stirred at room temperature for 3 hours. Ethanol (1 ml) was added to the reaction mixture, and the resultant mixture was stirred for 2 hours. Deposits were collected by filtration and washed successively with ethanol and diisopropyl ether to obtain the title compound (193 mg) as a colorless powder.

Melting point: 245–248° C.

$^1$H-NMR (d$^6$-DMSO) δ: 2.92(t,J=2 Hz,3H), 3.13(dd,J=5 Hz,J=8 Hz,3H), 5.66(m,1H), 6.63(brs,1H), 6.95(m,1H), 7.12(t,J=10 Hz,1H), 7.96(d,J=14 Hz,1H), 8.47(s,1H).

Example 24
Synthesis of 7-(2-Aminoethyl)amino-1-(5-amino-2,4-difluorophenyl)-8-chloro-6-fluoro-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (100 mg), ethylenediamine (16 mg) and triethylamine (70 mg) were added to acetonitrile (5 ml), and the mixture was heated under reflux for 2 hours. After the reaction mixture was allowed to cool, deposits were collected by filtration. The deposits were washed successively with ethanol and diethyl ether to obtain the title compound (72 mg) as a pale yellow powder.

Melting point: 204–210° C. (decomposed).

$^1$H-NMR (d$^6$-DMSO) δ: 2.80(brs,2H), 3.53(brs,2H), 5.44 (s,2H), 6.96(t,J=9 Hz,1H), 7.37(t,J=10 Hz,1H), 7.96(d,J=13 Hz,1H), 8.43(s,1H).

Example 25
Synthesis of 1-(5-Amino-2,4-difluorophenyl)-8-chloro-7-cyclopropylamino-6-fluoro-4-oxo-1,4-dihydroquinoline-3-carboxylic Acid Cyclopropylamine (50 mg) and 1-(5-amino-2,4-difluorophenyl)-8-chloro-6,7-difluoro-4-oxo-1,4-dihydroquinoline-3-carboxylic acid (150 mg) were, added to N,N-dimethylformamide (2 ml), and the mixtures was stirred at 60° C. for 2 hours. After the reaction mixture was cooled back to room temperature, the solvent was, distilled off under reduced pressure. Ethanol was added to the residue, and solids deposited were collected by filtration to obtain the title compound (80 mg) as a pale yellow powder.

Melting point: 141–143° C.

$^1$H-NMR (d$^6$-DMSO) δ: 0.97(m,2H), 1.05(m,2H), 3.35 (m,1H), 5.77(s,2H), 7.01(s,1H), 7.29(dd,J=8 Hz,J=9 Hz,1H), 7.71(t,J=10 Hz,1H), 8.34(d,J=13 Hz,1H), 8.81(s, 1H).

Example 26
Synthesis of 1-(5-Amino-2,4-difluorophenyl)-8-chloro-7-dimethylamino-6-fluoro-4-oxo-1,4-dihydroquinoline-3-carboxylic Acid Hydrochloride 1-(5-Amino-2,4-difluorophenyl)-8-chloro-6,7-difluoro-4-oxo-1,4-dihydroquinoline-3-carboxylic acid (100 mg), dimethylamine hydrochloride (94 mg) and triethylamine (140 mg) were added to acetonitrile (10 ml), and the mixture was heated and stirred overnight at 60° C. After the reaction mixture was allowed to cool, the solvent was distilled off under reduced pressure. Ethanol and concentrated hydrochloric acid were added to the residue, and the mixture was concentrated again under reduced pressure. Ethanol was added to the residue, and solids were collected by filtration. The solids were washed successively with ethanol and diethyl ether to obtain the title compound (70 mg) as a yellow powder.

Melting point: 228–235° C.

$^1$H-NMR (d$^6$-DMSO) δ: 2.93(s,3H), 2.94(s,3H), 7.09(m, 1H), 7.43(t,J=10 Hz,1H), 8.04(d,J=12 Hz,1H), 8.59(s,1H).

Example 27

Synthesis of 1-(5-amino-2,4-difluorophenyl)-6-fluoro-7-methylamino-4-oxo-1,4-dihydro-1,8-naphthyridine-3-carboxylic Acid A 40% aqueous solution (150 mg) of methylamine and 1-(5-amino-2,4-difluorophenyl)-7-chloro-6-fluoro-4-oxo-1,4-dihydro-1,8-naphthyridine-3-carboxylic acid (150 mg) were added to pyridine (2 ml), and the mixture was stirred at room temperature for 2 hours. After the solvent was distilled off under reduced pressure, ethanol was added to the residue, and solids deposited were collected by filtration to obtain the title compound (40 mg) as colorless crystals.

Melting point: >270° C. (decomposed).

$^1$H-NMR (d$^6$-DMSO) δ: 2.67(d,J=4 Hz,3H), 5.37(s,2H), 6.98(t,J=8 Hz,1H), 7.37(t,J=10 Hz,1H), 7.99(d,J=11 Hz,1H), 8.36(brs,1H), 8.68(s,1H).

Example 28

Synthesis of 1-(6-Amino-3,5-difluoropyridin-2-yl)-8-chloro-6-fluoro-7-methylamino-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (200 mg) and a 40% aqueous solution (220 mg) of methylamine were added to pyridine (820 mg), and the mixture was stirred at room temperature for 2 hours. The solvent was distilled off under reduced pressure, and ethanol (2 ml) was added to the residue. Deposits were collected by filtration and washed successively with ethanol and diisopropyl ether to obtain the title compound (182 mg) as a colorless powder.

Melting point: 251–253° C.

$^1$H-NMR (d$^6$-DMSO) δ: 3.13(dd,J=5 Hz,J=8 Hz,3H), 6.71(brs,1H), 6.77(brs,2H), 7.94(d,J=14 Hz,1H), 7.96(t,J=9 Hz,1H), 8.70(s,1H).

Example 29

Synthesis of 1-(6-Amino-3,5-difluoropyridin-2-yl)-6,8-difluoro-7-methylamino-4-oxo-1,4-dihydroquinoline-3-carboxylic Acid 1-(6-Amino-3,5-difluoropyridin-2-yl)-6,7,8-trifluoro-4-oxo-1,4-dihydroquinoline-3-carboxylic acid (60 mg) and a 40% aqueous solution (110 mg) of methylamine were added to pyridine (1,160 mg), and the mixture was stirred at 40° C. for 16 hours. The solvent was distilled off under reduced pressure, and ethanol (1 ml) was added to the residue. Deposits were collected by filtration and washed successively with ethanol and diisopropyl ether to obtain the title compound (58 mg) as a colorless powder.

Melting point: 270–273° C.

$^1$H-NMR (d$^6$-DMSO) δ: 2.98(brd,J=4 Hz,3H), 6.76(brs, 1H), 6.80(brs,2H), 6.95(m,1H), 7.80(d,J=13 Hz,1H), 8.01(t, J=10 Hz,1H), 8.76(s,1H).

Example 30

Synthesis of 1-(6-Amino-3,5-difluoropyridin-2-yl)-8-bromo-6-fluoro-7-methylamino-4-oxo-1,4-dihydroquinoline-3-carboxylic Acid 1-(6-Amino-3,5-difluoropyridin-2-yl)-8-bromo-6,7-difluoro-4-oxo-1,4-dihydroquinoline-3-carboxylic acid (200 mg) and a 40% aqueous solution (230 mg) of methylamine were added to pyridine (620 mag), and the mixture was stirred at room temperature for 2 hours. The solvent was distilled off under reduced pressure, and ethanol (2 ml) was added to the residue. Deposits were collected by filtration and washed successively with ethanol and diisopropyl ether to obtain the title compound (103 mg) as a colorless powder.

Melting point: 205–208° C.

$^1$H-NMR (d$^6$-DMSO) δ: 3.14(dd,J=5 Hz,J=8 Hz,3H), 6.51(m,1H), 6.77(brs,2H), 7.94(t,J=9 Hz,1H), 7.97(d,J=14 Hz,1H), 8.69(s,1H).

Example 31

Synthesis of 5-Amino-1-(6-amino-3,5-difluoropyridin-2-yl)-8-chloro-6-fluoro-7-methylamino-4-oxo-1,4-dihydroquinoline-3-carboxylic Acid 5-Amino-1-(6-amino-3,5-difluoropyridin-2-yl)-8-chloro-6,7-difluoro-4-oxo-1,4-dihydroquinoline-3-carboxylic acid (23 mg) and a 40% aqueous solution (60 mg) of methylamine were added to pyridine (240 mg), and the mixture was stirred at room temperature for 20 hours. The solvent was distilled off under reduced pressure, and ethanol (0.5 ml) was added to the residue. Deposits were collected by filtration and washed successively with ethanol and diisopropyl ether to obtain the title compound (6 mg) as a yellow powder.

Melting point: 250–253° C. (decomposed).

$^1$H-NMR (d$^6$-DMSO) δ: 3.09(dd,J=5 Hz,J=8 Hz,3H), 6.26(m,1H), 6.72(brs,2H), 7.57(brs,1H), 7.90(t,J=10 Hz,1H), 8.47(s,1H).

Example 32

Synthesis of 1-(6-Amino-3-fluoropyridin-2-yl)-8-chloro-6-fluoro-7-methylamino-4-oxo-1,4-dihydroquinoline-3-carboxylic Acid 1-(6-Amino-3-fluoropyridin-2-yl)-8-chloro-6,7-difluoro-4-oxo-1,4-dihydroquinoline-3-carboxylic acid (45 mg) and a 40% aqueous solution (50 mg) of methylamine were added to pyridine (200 mg), and the mixture was stirred at room temperature for 5 hours. The solvent was distilled off under reduced pressure, and ethanol (0.5 ml) was added to the residue. Deposits were collected by filtration and washed successively with methanol and diisopropyl ether to obtain the title compound (182 mg) as a yellow powder.

Melting point: 237–242° C. (decomposed).

$^1$H-NMR (d$^6$-DMSO) δ: 3.13(m,3H), 6.48(brs,2H), 6.67 (m+brs,2H), 7.62(t,J=9 Hz,1H), 7.95(d,J=14 Hz,1H), 8.65 (s,1H).

Referential Example 4

Synthesis of Ethyl 2,4-Difluoro-5-nitrobenzoylacetate 2,4-Difluoro-5-nitrobenzoic acid (5.0 g) was dissolved in dichloromethane (25 ml) and N,N-dimethylformamide (0.5 ml). Oxalyl chloride (5.6 ml) was added dropwise to this solution, and the mixture was stirred at room temperature for 19 hours. The solvent was distilled off under reduced pressure, and azeotropic distillation was conduct 3 times with dry tetrahydrofuran. The residue was dissolved in tetrahydrofuran (10 ml). This solution is regarded as Solution A. Magnesium (610 mg) was added to ethanol (1 ml), and carbon tetrachloride (0.2 ml) was added to the resultant mixture. A solution of ethyl malonate (4.0 g) in tetrahydrofuran (10 ml) and ethanol (1.5 ml) were added dropwise to the mixture at the time a reaction started. Thereafter, the reaction mixture was stirred for 4 hours while heating under reflux. After the reaction mixture was cooled, it was slowly added dropwise to Solution A at −70° C. The temperature of the reaction mixture was slowly raised to room temperature. The solvent was distilled off under reduced pressure. The residue was extracted with chloroform (50 ml), and the resultant extract was washed with 3N hydrochloric acid. The solvent was distilled off under reduced pressure. Water (50 ml) and p-toluenesulfonic acid monohydrate (0.5 g) were added to the residue, and the mixture was stirred for 30 hours while heating under reflux. The reaction mixture was extracted with chloroform. An organic layer was dried and then concentrated. The resultant residue. was subjected to column chromatography on silica gel (eluent; chloroform) to obtain the title compound (4.5 g) as a yellow oil.

$^1$H-NMR (CDCl$_3$) δ: 1.25–1.45(m,3H), 4.20–4.45(m, 2H), 5.87(s), 7.16(dd,J=8 Hz,J=11 Hz,1H), 8.72(dd,J=8 Hz,9 Hz,1H).

Referential Example 5

Synthesis of 2,3,4-Trifluoro-5-nitrobenzoic Acid 2,3,4-Trifluorobenzoic acid (2.5 g) was dissolved in concentrated sulfuric acid (15 ml). Potassium nitrate (1.62 g) was added to the solution under ice cooling. The temperature of the reaction mixture was (given back to room temperature to conduct stirring for 2 days. The reaction mixture was poured into ice water (300 ml) and extracted with ether (200 ml). An organic layer was dried and concentrated. Hexane was added to the residue to conduct filtration, thereby obtaining the title compound (3.06 g) as a pale yellow powder.

$^1$H-NMR (d$^6$-DMSO) δ: 8.40–8.47(m,1H).

Referential Example 6

Synthesis of Ethyl 2,3,4-Trifluoro-5-nitrobenzoylacetate 2,3,4-Trifluoro-5-nitrobenzoic acid (3.0 g) was dissolved in dichloromethane (20 ml) and N,N-dimethylformamide (0.3 ml). Oxalyl chloride (3 ml) was added dropwise to this solution, and the mixture was stirred at room temperature for 15 hours. The solvent was distilled off under reduced pressure, and azeotropic distillation was conducted 3 times with dry tetrahydrofuran. The residue was dissolved in tetrahydrofuran (10 ml). This solution is regarded as Solution A. Magnesium (336 mg) was added to ethanol (1 ml), and carbon tetrachloride (0.1 ml) was added to the resultant mixture. A solution of ethyl malonate (2.25 g) in tetrahydrofuran (10 ml) and ethanol (0.5 ml) was added dropwise to the mixture at the time a reaction started. Thereafter, the reaction mixture was stirred for 4 hours while heating under reflux. The reaction mixture was slowly added dropwise to Solution A at −70° C. The temperature of the reaction mixture was slowly raised to room temperature. The solvent was distilled off under reduced pressure. The residue was extracted with chloroform (50 ml), and the resultant extract was washed with 3N hydrochloric acid. The solvent was distilled off under reduced pressure. Water (30 ml) and p-toluenesulfonic acid monohydrate (0.3 g) were added to the resultant residue, and the mixture was stirred for 3.5 hours while heating under ref lux. The reaction mixture was extracted with chloroform, and an organic layer was dried and then concentrated. The resultant residue was subjected to column chromatography on silica gel (eluent; ethyl acetate:hexane=1:8) to obtain the title compound (1.4 g) as a yellow oil.

$^1$H-NMR (CDCl$_3$) δ: 1.20–1.40(m,3H), 4.15–4.35(m, 2H), 5.88(s), 8.45–8.65(m,1H).

Referential Example 7

Synthesis of 3-Chloro-2,4,5-trifluoro-6-methylbenzoic Acid

A 1.69 M hexane solution (14 ml) of n-butyllithium was added dropwise to a solution of diisopropylamine (3.6 ml) in tetrahydrofuran (15 ml) at −65° C. in a nitrogen gas stream, and the mixture was stirred at the same temperature for 15 minutes. A solution of 3-chloro-2,4,5-trifluorobenzoic acid (2.1 g) in tetrahydrofuran (15 ml) was added dropwise to the reaction mixture at −60° C., and the mixture was stirred at the same temperature for 15 minutes. Methyl iodide (1.9 ml) was added dropwise at −70° C., and the resultant mixture was stirred for 30 minutes at the same temperature and for 30 minutes at room temperature. Diethyl ether and water were added to the reaction mixture to conduct liquid separation. A water layer was collected, to which 12N hydrochloric acid was added to acidify the water layer. The water layer was then extracted with diethyl ether. An organic layer was dried over anhydrous magnesium sulfate, and the solvent was distilled off under reduced pressure to obtain the title compound (2.3 g) as an oil.

$^1$H-NMR (CDCl$_3$) δ: 2.43(d,J=3 Hz,3H).

Referential Example 8

Synthesis of Ethyl 3-Chloro-2,4,5-trifluoro-6-methylbenzoylacetate

Magnesium (240 mg), ethanol (1 ml) and carbon tetrachloride (0.1 ml) were stirred at room temperature in a three necked flask to activate them. A solution of ethyl malonate (1.5 ml) in tetrahydrofuran (8 ml) was slowly added dropwise to the activated mixture, followed by stirring at 80° C. for 4 hours. After the reaction mixture was allowed to cool, it was chilled to −40° C. Oxalyl chloride (0.8 ml) and N,N-dimethylformamide (1 drop) were added to a solution of 3-chloro-2,4,5-trifluoro-6-methylbenzoic acid (2 g) in methylene chloride (5 ml). The mixture was stirred at room temperature for 3.5 hours, and the solvent and reagents remaining in the reaction mixture were distilled off under reduced pressure. Toluene was added to the residue to conduct azeotropic distillation. The resultant residue was dissolved in tetrahydrofuran (5 ml), and the solution was slowly added dropwise at −40° C. to the reaction mixture obtained previously. After completion of the addition, the temperature of the reaction mixture was given back to room temperature to conduct stirring overnight. The solvent in the reaction mixture was distilled off, and 12N hydrochloric acid (2 ml) was added to the resultant residue to keep its pH at about 2. The residue was then extracted with chloroform, and the solvent was distilled off under reduced pressure. Water (10 ml) and p-toluenesulfonic acid monohydrate (100 mg) were added to the resultant residue, and the mixture was stirred for 4.5 hours while heating under reflux. After the reaction mixture was allowed to cool, it was extracted with chloroform. An organic layer was washed with water dried over anhydrous magnesium sulfate, and then concentrated under reduced pressure. The residue was subjected to column chromatography on silica gel to obtain the title compound (600 mg) as a pale yellow oil from a fraction eluted with a 1:10 mixture of ethyl acetate and hexane.

Referential Example 9

Synthesis of 5-Bromo-2-fluoro-4-nitrotoluene

5-Bromo-2-fluorotoluene (7.65 g) was added to concentrated sulfuric acid (40 ml), and potassium nitrate (4.2 g) was added portionwise to the mixture at −20° C. The temperature of the reaction mixture was given back to room temperature to conduct stirring for 3 days, and then poured into ice water to conduct extraction with ethyl acetate. After an organic layer was dried over anhydrous magnesium sulfate, the solvent was distilled off to obtain the title compound (9.9 g) as a pale yellow oil.

$^1$H-NMR (CDCl$_3$) δ: 2.38(s,3H), 7.57–7.68(m,2H).

Referential Example 10
Synthesis of 2-Bromo-5-fluoro-4-methylaniline

Iron powder (18.5 g) was added to a solution of 5-bromo-2-fluoro-4-nitrotoluene (9.7 g) in acetic acid (30 ml), and the mixture was stirred at 70° C. for 3 hours. The catalyst was removed by filtration through Celite, and the filtrate was washed with chloroform. The solvent and the like in the filtrate were distilled off under reduced pressure. The residue was subjected to column chromatography on silica gel to conduct elution with chloroform, thereby obtaining the title compound (7.9 g) as a red oil.

$^1$H-NMR (CDCl$_3$) δ: 2.13(s,3H), 6.46(d,J=11 Hz,1H), 7.20(d,J=8 Hz,1H).

Referential Example 11
Synthesis of 5-Bromo-4-chloro-2-fluorotoluene

Cupric chloride (6 g) and butyl nitrite (4.8 g) were added to acetonitrile (16 ml), and the mixture was stirred at 60° C. for 10 minutes. A solution of 2-bromo-5-fluoro-4-methylaniline (7.6 g) in acetonitrile (30 ml) was added dropwise to the mixture at the same temperature, and the resultant mixture was then stirred at the same temperature for 30 minutes. After the reaction mixture was allowed to cool, 2N hydrochloric acid was added to acidify the reaction mixture, and it was extracted with diethyl ether. After an organic layer was dried over anhydrous magnesium sulfate, the solvent was distilled off. The residue was subjected to column chromatography on silica gel to conduct elution with n-hexane, thereby obtaining the title compound (5.6 g) as a pale yellow oil.

$^1$H-NMR (CDCl$_3$) δ: 2.24(s,3H), 7.14(d,J=9 Hz,1H), 7.43 (d,J=8 Hz,1H).

Referential Example 12
Synthesis of 2-Chloro-4-fluoro-5-methylbenzoic Acid n-Butyllithium (1.69 M hexane solution; 14 ml) was added dropwise to a solution of 5-bromo-4-chloro-2-fluorotoluene (5.6 g) in absolute diethyl ether (100 ml) at −70° C. in a nitrogen gas stream, and the mixture was stirred at the same temperature for 1 hour. Carbon dioxide was blown into the mixture at −70° C. for 30 minutes. The temperature of the reaction mixture was given back to room temperature to conduct stirring for 2 days. Diethyl ether and water were added to the reaction mixture to conduct liquid separation. A water layer was collected, to which concentrated hydrochloric acid was added to acidify the water layer. The water layer was then Extracted with diethyl ether. An organic layer was dried over anhydrous magnesium sulfate, and the solvent was distilled off to obtain the title compound (3.3 g) as a yellow solid.

$^1$H-NMR (CDCl$_3$) δ: 2.30(s,3H), 7.17(d,J=9 Hz,1H), 7.93 (d,J=8 Hz,1H).

Referential Example 13
Synthesis of Ethyl 2-Chloro-4-fluoro-5-methylbenzoylacetate Magnesium (110 mg), ethanol (2 ml) and carbon tetrachloride (0.2 ml) were stirred at room temperature to activate them. A solution of ethyl malonate (0.7 ml) in tetrahydrofuran (6 ml) was added dropwise to the activated mixture, followed by stirring at 80° C. for 4 hours. After the reaction mixture was allowed to cool, it was chilled to −40° C. Oxalyl chloride (0.4 ml) and N,N-dimethylformamide (1 drop) were added to a solution of 2-chloro-4-fluoro-5-methylbenzoic acid (800 mg) in methylene chloride (2 ml). The mixture was stirred at room temperature for 3.5 hours, and the solvent and the like were distilled off. Toluene was added to the residue to conduct azeotropic distillation. The resultant residue was dissolved in tetrahydrofuran (5 ml), and the solution was added dropwise at −40° C. to the reaction mixture obtained previously. After the addition, the temperature of the reaction mixture was given back to room temperature to conduct stirring overnight. The solvent was distilled off, and 12N hydrochloric acid (1 ml) was added to the resultant residue to keep its pH at about 2. The residue was then extracted with chloroform, and the solvent was distilled off. Water (10 ml) and p-toluenesulfonic acid monohydrate (50 mg) were added to the resultant residue, and the mixture was stirred for 4 hours while heating under reflux. After the reaction mixture was allowed to cool, it was extracted with chloroform. An organic layer was washed with water, dried over anhydrous magnesium sulfate, and then concentrated under reduced pressure to obtain the title compound (1.0 g) as a pale yellow oil.

Referential Example 14
Synthesis of 2-Chloro-4-fluoro-5-methyl-3-nitrobenzoic Acid 2-Chloro-4-fluoro-5-methylbenzoic acid (2.0 g) was added to concentrated sulfuric acid (20 ml) to dissolve it, and potassium nitrate (1.07 g) was added portionwise to the solution under ice cooling. After the addition, the temperature of the reaction mixture was given back to room temperature to conduct stirring overnight. The reaction mixture was poured into ice water and extracted with diethyl ether. After an organic layer was collected and dried over anhydrous magnesium sulfate, the solvent was distilled off to obtain the title compound (2.25 g) as a reddish brown oil.

$^1$H-NMR (CDCl$_3$) δ: 2.40(d,J=2 Hz,3H), 8.05(d,J=8 Hz,1H).

Referential Example 15
Synthesis of Ethyl 2-Chloro-4-fluoro-5-methyl-3-nitrobenzoylacetate Magnesium (115 mg), ethanol (1 ml) and carbon tetrachloride (0.1 ml) were stirred at room temperature to activate them. A solution of ethyl malonate (0.69 ml) in tetrahydrofuran (5 ml) was added dropwise to the activated mixture, followed by stirring at 80° C. for 3 hours. After the reaction mixture was allowed to cool, it was chilled to −40° C. Oxalyl chloride (650 mg) and N,N-dimethylformamide (1 drop) were added to a solution of 2-chloro-4-fluoro-5-methyl-3-nitrobenzoic acid (1.0 g) in methylene chloride (10 ml). The mixture was stirred overnight at room temperature, and the solvent and the like were distilled off. Toluene was added to the residue to conduct azeotropic distillation. The resultant residue was dissolved in tetrahydrofuran (5 ml), and the solution was added dropwise at −40° C. to the reaction mixture obtained previously. After the addition, the temperature of the reaction mixture was given back to room temperature to conduct stirring overnight. The solvent was distilled off, and 12N hydrochloric acid (1 ml) was added to the resultant residue to keep its pH at about 2. The residue was then extracted with chloroform, and the solvent was distilled off. Water (10 ml) and p-toluenesulfonic acid monohydrate (50 mg) were added to the resultant residue, and the mixture was stirred for 1 hour while heating under reflux. After the reaction mixture was allowed to cool, it was extracted with chloroform. An organic layer was washed with water, dried over anhydrous magnesium sulfate, and then concentrated under reduced pressure. The resultant residue was subjected to column chromatography on silica gel to obtain the title compound (630 mg) as a pale yellow oil from a fraction eluted with a 1:10 mixture of ethyl acetate and hexane.

Referential Example 16
Synthesis of 2-Fluoro-5-methoxy-3-methyl-4-nitrobenzoic Acid Sodium methoxide (28% methanol solution; 1.66 g) was added to a solution of methyl 2,5-difluoro-3-methyl-4-nitrobenzoate (1.0 g) in acetonitrile (5 ml) under ice cooling, and the mixture was stirred for 1 hour at 0° C. and for 2 hours at 50° C. The reaction mixture was additionally stirred overnight at room temperature and then poured into ice water. The mixture was acidified with citric acid and then extracted with diethyl ether. An organic layer was dried over anhydrous magnesium sulfate, and the solvent was distilled off under reduced pressure. Diethyl ether was added to the residue, and insoluble matter was removed by filtration. The filtrate was concentrated under reduced pressure to obtain the title compound (1.1 g).

Referential Example 17
Synthesis of Ethyl 2-Fluoro-5-methoxy-3-methyl-4-nitrobenzoylacetate Magnesium (150 mg), ethanol (1 ml) and carbon tetrachloride (0.05 ml) were stirred at room temperature to activate them. A solution of ethyl malonate (1.0 ml) in tetrahydrofuran (6 ml) was added dropwise to the activated mixture, followed by stirring at 80° C. for 4 hours. After the reaction mixture was allowed to cool, it was chilled to −40° C. Oxalyl chloride (0.5 ml) and N,N-dimethylformamide (1 drop) were added to a solution of 2-fluoro-5-methoxy-3-methyl-4-nitrobenzoic acid (1.4 g) in methylene chloride (5 ml). The mixture was stirred at room temperature for 3 hours, and the solvent and the like in the reaction mixture were distilled off. Toluene was added to the residue to conduct azeotropic distillation. The resultant residue was dissolved in tetrahydrofuran (5 ml), and the solution was added dropwise at −40° C. to the reaction mixture obtained previously. After the addition, the temperature of the reaction mixture was given back to room temperature to conduct stirring overnight. The solvent was distilled off, and 12N hydrochloric acid (3 ml) was added to the resultant residue to keep its pH at about 2. The residue was then extracted with chloroform, and the solvent was distilled off. Water (10 ml) and p-toluenesulfonic acid monohydrate (80 mg) were added to the resultant residue, and the mixture was stirred for 5 hours while heating under reflux. After the reaction mixture was allowed to cool, it was extracted with chloroform. An organic layer was washed with water, dried over anhydrous magnesium sulfate, and then concentrated under reduced pressure. The resultant residue was subjected to column chromatography on silica gel to obtain the title compound (240 mg) as a pale yellow oil from a fraction eluted with a 1:10 mixture of ethyl acetate and hexane.

Referential Example 18
Synthesis of Ethyl 6,7-Difluoro-1-(4-fluoro-3-ethoxyphenyl)-8-methyl-4-oxo-1,4-dihydroquinoline-3-carboxylate 4-Fluoro-3-methoxyaniline (1.4 g) was added to a chloroform solution (10 ml) of ethyl 3-ethoxy-2-(2,4,5-trifluoro-3-methylbenzoyl)acrylate synthesized from ethyl 2,4,5-trifluoro-3-methylbenzoylacetate (2.6 g) in accordance with a method known per se in the art. The mixture was concentrated under reduced pressure, and anhydrous potassium carbonate (3.0 g) and N,N-dimethylformamide (7 ml) were added to the residue, followed by stirring at 90° C. for 15 minutes. The reaction mixture was allowed to cool, and chloroform (100 ml) and distilled water (250 ml) were added to the mixture, thereby conducting liquid separation. A chloroform layer was then washed twice with distilled water (250 ml), dried over anhydrous magnesium sulfate and concentrated under reduced pressure. Deposits were dispersed in ethanol, collected by filtration and washed with ethanol and diisopropyl ether in that order to obtain the title compound (2.59 g) as a colorless powder.

Melting point: 273–277° C.
$^1$H-NMR (CDCl$_3$) δ: 1.40(t,J=7 Hz,3H), 1.76(d,J=3 Hz,3H), 3.94(s,3H), 4.39(q,J=7 Hz,2H), 6.97(m,2H), 7.25 (dd,J=8 Hz,10 Hz,1H), 8.23(t,J=9 Hz,1H), 8.43(s,1H).

Referential Example 19
Synthesis of Ethyl(2,4-difluoro-!5-methoxyphenyl)-6,7-difluoro-8-methyl-4-oxo-1,4-dihydroquinoline-3-carboxylate 2,4-Difluoro-5-methoxyaniline hydrobromide (2.4 g) was added together with triethylamine (1.2 g) to a chloroform solution of ethyl 3-ethoxy-2-(2,4,5-trifluoro-3-methylbenzoyl)acrylate (2.6 g) synthesized from ethyl 2,4,5-trifluoro-3-methylbenzoylacetate (10 ml) in accordance with the method known per se in the art. The mixture was concentrated under reduced pressure, and anhydrous potassium carbonate (3.7 g) and N,N-dimethylformamide (15 ml) were added to the residue, followed by stirring at 90° C. for 15 minutes. The reaction mixture was allowed to cool, and chloroform (60 ml) and distilled water (300 ml) were added thereto, thereby conducting liquid separation. A chloroform layer was washed twice with distilled water (300 ml), dried over anhydrous magnesium sulfate and then concentrated under reduced pressure. Deposits were dispersed in ethanol, collected by filtration and washed with ethanol and diisopropyl ether in that order to obtain the title compound (2.96 g) as a colorless powder.

Melting point: 262–264° C.
$^1$H-NMR (CDCl$_3$) δ: 1.38(t,J=7 Hz,3H), 1.80(d,J=3 Hz,3H), 3.96(s,3H), 4.36(q,J=7 Hz,2H), 7.12(t,J=10 Hz,1H), 7.17(t,J=8 Hz,1H), 8.16(t,J=9 Hz,1H), 8.30(s,1H).

Referential Example 20
Synthesis of Ethyl 8-Chloro-6,7-difluoro-1-[3,5-difluoro-6-(2-hydroxyethylamino)pyridin-2-yl]-4-oxo-1,4-dihydroquinoline-3-carboxylate 2-Amino-3,5,6-trifluoropyridine (1.5 g) and ethanolamine (1.8 g) were added to N-methylpyrrolidone (5 ml) to conduct a reaction at 140° C. for 22 hours. The reaction mixture was allowed to cool, and chloroform (50 ml) and distilled water (50 ml) were added thereto, thereby conducting liquid separation. A water layer was extracted again with chloroform (20 ml). The chloroform layers were put together, dried over anhydrous magnesium sulfate and then concentrated under reduced pressure. The resultant residue was added to a chloroform solution (8 ml) of ethyl 3-ethoxy-2-(3-chloro-2,4,5-trifluorobenzoyl)acrylate synthesized from ethyl 3-chloro-2,4,5-trifluorobenzoylacetate (2.15 g) in accordance with a method known per se in the art. The mixture was concentrated under reduced pressure, and anhydrous potassium carbonate (2 g) and N,N-dimethylformamide (2 ml) were added to the resultant residue, followed by stirring at 90° C. for 15 minutes. The reaction mixture was allowed to cool, and chloroform (60 ml) and distilled water (300 ml) were added thereto, thereby conducting liquid separation. A chloroform layer was washed twice with distilled water (300 ml), dried over anhydrous magnesium sulfate and concentrated under reduced pressure. Ethanol (6 ml) was added to the resultant residue, and the mixture was left to stand. Deposits were collected by filtration and washed with ethanol and diisopropyl ether in that order to obtain the title compound (2.15 g) as a pale brown powder.

Melting point: 163–164° C.

$^1$H-NMR (CDCl$_3$) δ: 1.40(t,J=7 Hz,3H), 2.01(t,J=5 Hz,1H), 3.58(m,2H), 3.82(q,J=5 Hz,2H), 4.40(q,J=7 Hz,2H), 5.33(br.1H), 7.26(dd,J=8Ha,9 Hz,1H), 8.31(dd,J=3 Hz,10 Hz,1H), 8.47(s,1H).

Referential Example 21

Synthesis of Ethyl 1-(5-Tert-butoxycarbonylamino-2,4-difluorophenyl)-7-fluoro-6-methyl-4-oxo-1,4-dihydroquinoline-3-carboxylate Acetic anhydride (2.3 g) and triethyl orthoformate (930 mg) were added to ethyl 2-chloro-4-fluoro-5-methylbenzoylacetate (1.0 g), and the mixture was heated under reflux for 2 hours. After the reaction mixture was allowed to cool, the reagents and the like were distilled off under reduced pressure. Toluene was additionally added to the residue to conduct azeotropic distillation. Chloroform (10 ml) was added to the residue, and a solution of N-tert-butoxycarbonyl-2,4-difluoro-m-phenylenediamine (951 mg) in chloroform (5 ml) was added dropwise to the resultant mixture, followed by stirring at room temperature for 10 minutes. The solvent was distilled off, and hexane was added to the residue to conduct filtration, thereby obtaining a pale yellow powder (1.1 g). Potassium carbonate (290 mg) was added to a solution of the whole amount of the thus-obtained compound in N,N-dimethylformamide (3 ml), and the mixture was stirred for 3 hours at room temperature and for 5 hours at 70° C. Ethyl acetate and water were added to the reaction mixture to collect an organic layer. After the organic layer was dried over anhydrous magnesium sulfate, the solvent was distilled off. The residue was subjected to column chromatography on silica gel to obtain the title compound (410 mg) as a pale yellow powder from a fraction eluted with a 1:2 mixture of ethyl acetate and hexane.

Melting point: 205–207° C.

$^1$H-NMR (CDCl$_3$) δ:

1.40(t,J=7 Hz,3H), 1.52(s,9H), 2.38(s,3H), 4.39(q,J=7 Hz,2H), 6.53(d,J=10 Hz,1H), 6.86(brs,1H), 7.17(t,J10 Hz,1H), 8.31–8.45(m,3H).

Referential Example 22

Synthesis of Ethyl 1-(5-Tert-butoxycarbonylamino-2,4-difluorophenyl)-7-fluoro-6-methyl-8-nitro-4-oxo-1,4-dihydroquinoline-3-carboxylate Acetic anhydride (610 mg) and triethyl orthoformate (450 mg) were added to ethyl 2-chloro-4-fluoro-5-methyl-3-nitrobenzoylacetate (630 mg), and the mixture was heated under reflux for 1.5 hours. After the reaction mixture was allowed to cool, the reagents and the like were distilled off under reduced pressure. Toluene was additionally added to the residue to conduct azeotropic distillation. Chloroform (5 ml) was added to the residue, and a solution of N-tert-butoxycarbonyl-2,4-difluoro-m-phenylenediamine (500 mg) in chloroform (7 ml) was added dropwise to the resultant mixture, followed by stirring at room temperature for 10 minutes. The solvent was distilled off, and potassium carbonate (280 mg) was added to a solution of the resultant residue in N,N-dimethylformamide (3 ml), followed by stirring at 60° C. for 30 minutes. Ethyl acetate and water were added to the reaction mixture to collect an organic layer. After the organic layer was dried over anhydrous magnesium sulfate, the solvent was distilled off. Solids deposited were collected by filtration and washed with ethanol to obtain the title compound (470 mg) as a pale yellow powder.

Melting point: 224–225° C.

$^1$H-NMR (CDCl$_3$) δ: 1.39(t,J=7 Hz,3H), 1.51(s,9H), 2.46 (s,3H), 4.39(q,J=7 Hz,2H), 6.76(brs,1H), 7.04(t,J=9 Hz,1H), 8.24–8.35(m,2H), 8.55(d,J=8 Hz,1H).

Referential Example 23

Synthesis of Ethyl 1-(5-Tert-butoxycarbonylamino-2,4-difluorophenyl)-6-methoxy-8-methyl-7-nitro-4-oxo-1,4-dihydroquinoline-3-carboxylate Acetic anhydride (250 mg) and triethyl orthoformate (180 mg) were added to ethyl 2-fluoro-5-methoxy-3-methyl-4-nitrobenzoylacetate (240 mg), and the mixture was heated under reflux for 1.5 hours. After the reaction mixture was allowed to cool, the reagents and the like were distilled off under reduced pressure. Toluene was additionally added to the residue to conduct azeotropic distillation. Chloroform (5 ml) was added to the residue, and a solution of N-tert-butoxycarbonyl-2,4-difluoro-m-phenylenediamine (195 mg) in chloroform (5 ml) was added dropwise to the resultant mixture, followed by stirring at room temperature for 20 minutes. The solvent in the reaction mixture was distilled off, and potassium carbonate (110 mg) was added to a solution of the resultant residue in N,N-dimethylformamide (3 ml), followed by stirring at 80C for 40 minutes. Ethyl acetate and water were added to the reaction mixture to collect an organic layer. After the organic layer was dried over anhydrous magnesium sulfate, the solvent was distilled off. Ethanol was added to the residue, and solids deposited were collected by filtration to obtain the title compound (235 mg) as a colorless powder.

Melting point: 223–224° C.

$^1$H-NMR (CDCl$_3$) δ: 1.41(t,J=7 Hz,3H), 1.51(s,9H), 1.78 (s,3H), 4.01(s,3H), 4.40(q,J=7 Hz,2H), 6.79(brs,1H), 7.10 (t,J=10 Hz,1H), 8.09(s,1H), 8.30–8.42(m,2H)).

Referential Example 24

Synthesis of Ethyl 1-(5-Tert-butoxycarbonylamino-2,4-difluorophenyl)-7-fluoro-8-methyl-6-nitro-4-oxo-1,4-dihydroquinoline-3-carboxylate Acetic anhydride (47 g) and triethyl orthoformate (20 g) were added to ethyl 2-chloro-4-fluoro-3-methyl-5-nitrobenzoylacetate (12.5 g), and the mixture was heated under reflux for 1 hour. After the reaction mixture was allowed to cool, the reagents and the like were distilled off under reduced pressure. Toluene was additionally added to the residue to conduct azeotropic distillation. Chloroform (30 ml) was added to the resldue, and a solution of N-tert-butoxycarbonyl-2,4-difluoro-m-phenylenediamine (10 g) in chloroform (20 ml) was added dropwise to the resultant mixture, followed by stirring at room temperature for 20 minutes. The solvent was distilled off, and potassium carbonate (5.5 g) was added to a solution of the resultant residue in N,N-dimethylformamide (30 ml), followed by stirring at 80° C. for 30 minutes. Ethyl acetate and water were added to the reaction mixture to collect an organic layer. After the organic layer was dried over anhydrous magnesium sulfate, the solvent was distilled off. Ethanol was added to the residue, and solids deposited were collected by filtration to obtain the title compound (11.3 g) as a pale yellow powder.

Melting point: 182–185° C.

$^1$H-NMR (CDCl$_3$) δ: 1.40(t,J=7 Hz,3H), 1.52(s,9H), 1.87 (d,J=3 Hz,3H), 4.40(q,J=7 Hz,2H), 6.92(brs,1H), 7.15(t,J=9 Hz,1H), 8.30–8.43(m,2H)), 9.11(d,J=8 Hz,1H).

Referential Example 25

Synthesis of Ethyl 7-Amino-1-(5-tert-butoxycarbonylamino-2,4-difluorophenyl)-6-methoxy-8-methyl-4-oxo-1,4-dihydroquinoline-3-carboxylate Acetic acid (2 ml) and iron powder (150 mg) were added to ethyl 1-(5-tert-butoxycarbonylamino-2,4-difluorophenyl)-6-methoxy-8-methyl-7-nitro-4-oxo-1,4-dihydroquinoline-3-carboxylate (200 mg), and the mixture was stirred at 80° C. for 40 minutes. The catalyst was removed by filtration through Celite, and the solvent and the like in the filtrate were distilled off. The residue was subjected to column chromatography on silica gel to conduct elution with chloroform, thereby obtaining the title compound (140 mg) as an amorphous substance.

$^1$H-NMR (CDCl$_3$) δ: 1.39(t,J=7 Hz,3H), 1.50(s,9H), 1.66 (s,3H), 4.00(s,3H), 4.37(q,J=7 Hz,2H), 6.82(brs,1H), 7.06 (t,J=10 Hz,1H), 7.82(s,$_1$H), 8.13–8.31(m,2H).

Referential Example 26

Synthesis of 6,7-Difluoro-1-(4-fluoro-3-methoxyphenyl)-8-methyl-4-oxo-1,4-dihydroquinoline-3-carboxylic Acid Ethyl 6,7-difluoro-1-(4-fluoro-3-methoxyphenyl)-8-methyl-4-oxo-1,4-dihydroquinoline-3-carboxylate (400 mg) was added to a mixed liquid (1:1, v/v; 4 ml) of 2N hydrochloric acid and acetic acid, and the mixture was stirred and heated under reflux for 5 hours. Deposits were collected by filtration and washed with ethanol and diisopropyl ether in that order to obtain the title compound (358 mg) as a colorless powder.

Melting point: >280° C.

$^1$H-NMR (d$^6$-DMSO) δ: 1.74(d,J=3 Hz,3H), 3.88(s,3H), 7.29(m,1H), 7.47(dd,J=9 Hz,11 Hz,1H), 7.64(m,1H), 8.27 (t,J=10 Hz,1H), 8.67(s,1H)).

Example 33

Synthesis of 1-(5-Amino-2-fluorophenyl)-8-chloro-6-fluoro-7-methylamino-4-oxo-1,4-dihydroquinoline-3-carboxylic Acid 1-(5-Amino-2-fluorophenyl)-8-chloro-6,7-difluoro-4-oxo-1,4-dihydroquinoline-3-carboxylic acid (100 mg) was added to a mixed liquid of a 40% aqueous solution (103 mg) of methylamine and pyridine (1 ml), and the mixture was stirred at room temperature for 2 hours. The solvent was distilled off under reduced pressure, and ethanol was added to the residue. Solids formed were collected by filtration and washed with hexane to obtain the title compound (85 mg) as a pale yellow powder.

Melting point: 269.5–271.0° C.

$^1$H-NMR (d$^6$-DMSO) δ: 3.12(dd,J=6 Hz,7 Hz,3H), 5.39 (brs,2H), 6.65(d,1H), 6.70–6.75(m,2H), 7.12(t,J=10 Hz,1H), 7.96(d,J=14 Hz,1H), 8.40(s,1H).

Example 34

Synthesis of 1-(5-Amino-2,4-difluorophenyl)-7-methylamino-6-nitro-4-oxo-1,4-dihydroquinoline-3-carboxylic Acid 1-(5-Amino-2,4-difluorophenyl)-7-fluoro-6-nitro-4-oxo-1,4-dihydroquinoline-3-carboxylic acid (100 mg) was added to a mixed liquid of a 40% aqueous solution (120 mg) of methylamine and pyridine (3 ml), and the mixture was stirred at room temperature for 3 hours. The solvent was distilled off under reduced pressure. The residue was acidified with 3% citric acid, and solids formed were collected by filtration. The solids were washed with water, ethanol and hexane to obtain the title compound (70 mg) as a yellow powder.

Melting point: >275.0° C. (decomposed).

$^1$H-NMR (d$^6$-DMSO) δ: 2.73(d,J=4 Hz,3H), 5.57(brs, 2H), 6.12(s,1H), 7.11(t,J=9 Hz,1H), 7.52(t,J=10 Hz,1H), 8.44(brs,1H), 8.71(s,1H), 8.99(s,$_1$H).

Example 35

Synthesis of 7-Amino-1-(5-amino-2,4-difluorophenyl)-6-nitro-4-oxo-1,4-dihydroquinoline-3-carboxylic Acid 1-(5-Amino-2,4-difluorophenyl)-7-fluoro-6-nitro-4-oxo-1,4-dihydroquinoline-3-carboxylic acid (70 mg) was added to a mixed liquid of 28% aqueous ammonia (85 mg) and pyridine (2 ml), and the mixture was stirred at 50° C. for 15 hours. The reaction mixture was acidified with 3% citric acid (20 ml), and solids formed were collected by filtration. The solids were subjected to azeotropic distillation with ethanol and toluene. Hexane was added to the residue to conduct filtration, thereby obtain the title compound (50 mg) as a yellow powder.

Melting point: >279.0° C. (decomposed).

$^1$H-NMR (d$^6$-DMSO) δ: 5.57(brs,2H), 6.61(brs,1H), 7.02(t,J=9 Hz,1H), 7.56(t,J= 10 Hz,1H), 7.78(brs,2H), 8.62(s,1H), 8.92(s,1H).

Referential Example 27

Synthesis of 1-(5-Amino-2,4-difluorophenyl)-7-fluoro-6-nitro-4-oxo-1,4-dihydroquinoline-3-carboxylic Acid Ethyl orthoformate (1.3 ml) and acetic anhydride (1.6 ml) were added to ethyl 2,4-difluoro-5-nitrobenzoylacetate (1.4 g), and the mixture was stirred at 120° C. for 19 hours. The reaction mixture was concentrated under reduced pressure, and the residue was subjected 3 times to azeotropic distillation with toluene. The resultant residue was dissolved in dichloromethane (20 ml), to which N-tert-butoxycarbonyl-2,4-difluoro-m-phenylenediamine (1.27 g) was added under ice cooling. The mixture was then stirred at room temperature for 3 hours. The solvent was distilled off under reduced pressure, and the residue was dissolved in N,N-dimethylformamide (5 ml). Anhydrous potassium carbonate (663 mg) was added to the solution, and the mixture was stirred at 40° C. for 20 minutes. The solvent was distilled off under reduced pressure, and the resultant residue was extracted with chloroform (100 ml). An organic layer was washed with 3% citric acid (80 ml) and saturated brine (60 ml), dried and then concentrated. The residue was subjected to column chromatography on silica gel (eluent; chloroform-:ethyl acetate=25:1) to obtain a pale yellow powder (1.46 g). This powder was dissolved in acetic acid (6 ml), and 3N hydrochloric acid (10 ml) was added to the solution, followed by stirring at 100° C. for 15 hours. The solvent was distilled off under reduced pressure to conduct azeotropic distillation with toluene. Ether was added to the resultant residue to conduct filtration, thereby obtaining the title compound (630 mg) as a yellow powder.

Melting point: 258.7–259.50C.

$^1$H-NMR (d$^6$-DMSO) δ: 5.58(brs,2H), 7.07(t,J=9 Hz,1H), 7.44–7.56(m,2H), 8.90(s,1H), 8.99(d,J=8 Hz,1H).

Example 36

Synthesis of 1-(5-Amino-2,4-difluorophenyl)-7-(1-methylhydrazino)-6-nitro-4-oxo-1,4-dihydroquinoline-3-carboxylic Acid 1-(5-Amino-2,4-difluorophenyl)-7-fluoro-6-nitro-4-oxo-1,4-dihydroquinoline-3-carboxylic acid (60 mg) was added to a mixed liquid of methylhydrazine (32 mg) and pyridine (0.5 ml), and the mixture was stirred at room temperature for 3 hours. Water (5 ml) was added. At this time, the pH of the reaction mixture was about 5. Solids formed were collected by filtration and subjected to azeotropic distillation with ethanol and toluene. Hexane was added to the resultant residue to conduct filtration, thereby obtaining the title compound (60 mg) as a brown powder.

Melting point: >168.0° C. (decomposed).

$^1$H-NMR (d$^6$-DMSO) δ: 2.94(brs,3H), 5.02(brs,2H), 5.57 (brs,2H), 6.27(s,1H), 7.06(t,J=8 Hz,1H), 7.52(t,J=10 Hz,1H), 8.36(s,1H), 8.72(s,1H).

Referential Example 28

Synthesis of 1-(5-Amino-2,4-difluorophenyl)-7,8-difluoro-6-nitro-4-oxo-1,4-dihydroquinoline-3-carboxylic Acid Ethyl orthoformate (1.2 ml) and acetic anhydride (1.5 ml) were added to ethyl 2,3,4-trifluoro-5-nitrobenzoylacetate (1.4 g), and the mixture was stirred at 120° C. for 19 hours. The reaction mixtures was concentrated under reduced pressure, and the residue was subjected 3 times to azeotropic distillation with toluene. The resultant residue was dissolved in dichloromethane (20 ml), to which N-tert-butoxycarbonyl-2,4-difluoro-m-phenylenediamine (1.17 g) was added under ice cooling. The mixture was then stirred at room temperature for 3 hours. The solvent was distilled off under reduced pressure, and the residue was dissolved in N,N-dimethylforamide (5 ml). Anhydrous potassium carbonate (663 mg) was added to the solution, and the mixture was stirred at 40° C. for 20 minutes. The solvent was distilled off under reduced pressure, and the residue was extracted with chloroform (100 ml). An organic layer was washed with 3% citric acid (80 ml) and saturated brine (60 ml), dried and then concentrated. The residue was subjected to column chromatography on silica gel (eluent; hexane-:ethyl acetate=4:1→chlorofom:ethyl acetate=25:1) to obtain a light-colored powder (0.56 g). This powder was dissolved in acetic acid (2 ml), and 3N hydrochloric acid (3 ml) was added to the solution, followed by stirring at 100° C. for 15 hours. The solvent was distilled off under reduced pressure to conduct azeotropic distillation with toluene. Ether was added to the resultant residue to conduct filtration, thereby obtaining the title compound (400 mg) as a yellow powder.

Melting point: 141.5–143.0° C.

$^1$H-NMR (d$^6$-DMSO) δ: 5.50–6.50(br,2H), 7.16(dd,J=8 Hz,9 Hz,1H), 7.46(dd,J=10 Hz,11 Hz,1H), 8.72(s,1H), 8.82 (d,J=7 Hz,1H).

Example 37

Synthesis of 1-(5-Amino-2,4-difluorophenyl)-8-fluoro-7-methylamino-6-nitro-1,4-dihydro-oxoquinoline-3-carboxylic Acid 1-(5-Amino-2,4-difluorophenyl)-7,8-difluoro-6-nitro-4-oxo-1,4-dihydroquinoline-3-carboxylic acid (70 mg) was added to a mixed liquid of a 40% aqueous solution (80 mg) of methylamine and pyridine (2 ml), and the mixture was stirred at room temperature for 1 hour. The solution was acidified with 3% citric acid (10 ml), and solids formed were collected by filtration. The solids were washed with water, ethanol and hexane to obtain the title compound (56 mg) as a yellow powder.

Melting point: 186.0–188.0° C.

$^1$H-NMR (d$^6$-DMSO) δ: 2.98(brs,3H), 5.47(brs,2H), 6.12 (s,1H), 7.11(t,J=8 Hz,1H), 7.52(dd,J=9 Hz,10 Hz,1H), 7.95 (brs,1H), 8.51(s,1H), 8.76(s,1H).

Example 38

Synthesis of 8-chloro-6-fluoro-1-(2,4-difluoro-5-hydroxyphenyl)-7-methylamino-4-oxo-1,4-dihydroquinoline-3-carboxylic Acid 8-Chloro-6,7-difluoro-1-(2,4-difluoro-5-hydroxyphenyl)-4-oxo-1,4-dihydroquinoline-3-carboxylic acid (200 mg) and an aqueous solution (about 40%; 550 mg) of methylamine were added to pyridine (1,200 mg), and the mixture was stirred at room temperature for 21 hours. The reaction mixture was concentrated under reduced pressure, and ethanol (1 ml) was added to the residue. Deposits were collected by filtration and washed with ethanol and diisopropyl ether in that order to obtain the title compound (173 mg) as a pale brown powder.

Melting point: 265–271° C. (decomposed).

$^1$H-NMR (d$^6$-DMSO) δ: 3.14(m,3H), 6.57(m,1H), 7.20(t, J=8 Hz,1H), 7.46(t,J10 Hz,1H), 8.43(s,1H).

Example 39

Synthesis of 1-(6-Amino-5-fluoropyridin-2-yl)-8-chloro-6-fluoro-7-methylamino-4-oxo-1,4-dihydroquinoline-3-carboxylic Acid 1-(6-Amino-5-fluoropyridin-2-yl)-8-chloro-6,7-difluoro-4-oxo-1,4-dihydroquinoline-3-carboxylic acid (158 mg) and an aqueous solution (about 40%; 165 mg) of methylamine were added to pyridine (480 mg), and the mixture was stirred at room temperature for 17 hours. The reaction mixture was concentrated under reduced pressure, and ethanol (1 ml) was added to the residue. Deposits were collected by filtration and washed with ethanol and diisopropyl ether in that order to obtain the title compound (168 mg) as a pale yellow powder.

Melting point: 233–238° C.

$^1$H-NMR (d$^6$-DMSO) δ: 3.13(m,3H), 6.57(m,1H), 6.81 (m,3H), 7.61(t,J=9 Hz,1H), 7.92(d,J=14 Hz,1H), 8.53(s,1H).

Example 40

Synthesis of 5-Amino-1-(6-amino-3,5-difluoropyridin-2-yl)-8-chloro-7-dimethylamino-6-fluoro-4-oxo-1,4-dihydroquinoline-3-carboxylic Acid 5-Amino-1-(6-amino-3, 5-difluoropyridin-2-yl)-8-chloro-6,7-difluoro-4-oxo-1,4-dihydroquinoline-3-carboxylic acid (100 mg) and an aqueous solution (about 50%; 170 mg) of dimethylamine were added to pyridine (500 mg), and the mixture was stirred at room temperature for 4 days. The reaction mixture was concentrated under reduced pressure, and ethanol (1 ml) was added to the residue. Deposits were collected by filtration and washed with ethanol and diisopropyl ether in that order to obtain the title compound (86 mg) as a yellow powder.

Melting point: 230–234° C. (decomposed).

$^1$H-NMR (d$^6$-DMSO) δ: 2.90(d,J=3 Hz,6H), 6.73(brs, 2H), 7.71(brs,2H), 7.90(t,J=10 Hz,1H), 8.62(s,1H).

Example 41

Synthesis of 8-Chloro-1-(2,4-difluoro-5-methoxyphenyl)-6-fluoro-7-methylamino-4-oxo-1,4-dihydroquinoline-3-carboxylic Acid 8-Chloro-6,7-difluoro-1-(2,4-difluoro-5-methoxyphenyl)-4-oxo-1,4-dihydroquinoline-3-carboxylic acid (90 mg) and an aqueous solution (about 40%; 200 mg) of methylamine were added to pyridine (520 mg), and the mixture was stirred at room temperature for 66 hours. The reaction mixture was concentrated under reduced pressure, and ethanol (1 ml) was added to the residue. Deposits were collected by filtration and washed with ethanol and diisopropyl ether in that order to obtain the title compound (88 mg) as a colorless powder.

Melting point: 239–241° C.

$^1$H-NMR (d$^6$-DMSO) δ: 3.13(dd,J=5 Hz,8 Hz,3H), 3.83 (s,3H), 6.65(m,1H), 7.70(t,J=11 Hz,1H), 7.72(t,J=8 Hz,1H), 7.98(d,J=14 Hz,1H), 8.59(s,1H).

Referential Example 29

Synthesis of 8-Chloro-6,7-difluoro-1-(4-fluoro-3-methoxyphenyl)-4-oxo-1,4-dihydroquinoline-3-carboxylic Acid Ethyl 8-chloro-6,7-difluoro-1-(4-fluoro-3-methoxyphenyl)-4-oxo-1,4-dihydroquinoline-3-carboxylate (400 mg) was added to a mixed liquid (1:1, v/v; 2.5 ml) of 2N hydrochloric acid and acetic acid, and the mixture was stirred and heated under reflux for 2 hours. Deposits were collected by filtration and washed with ethanol and diisopropyl ether in that order to obtain the title compound (351 mg) as a colorless powder.

Melting point: >280° C.

$^1$H-NMR (d$^6$-DMSO) δ: 3.85(s,3H), 7.27(m,1H), 7.45 (dd,J=9 Hz,11 Hz,1H), 7.63(dd,J=3 Hz,8 Hz,1H), 7.97(dd, J=9 Hz,10 Hz,1H), 8.67(s,1H).

Example 42

Synthesis of 8-Chloro-6-fluoro-1-(4-fluoro-3-methoxyphenyl)-7-methylamino-4-oxo-1,4-dihydroquinoline-3-carboxylic Acid 8-Chloro-6,7-difluoro-1-(4-fluoro-3-methoxyphenyl)-4-oxo-1,4-dihydroquinoline-3-carboxylic acid (160 mg) and an aqueous solution (about 40%; 400 mg) of methylamine were added to pyridine (1,000 mg), and the mixture was stirred at room temperature for 27 hours. The reaction mixture was concentrated under reduced pressure, and ethanol (1 ml) was added to the residue. Deposits were collected by filtration and washed with ethanol and diisopropyl ether in that order to obtain the title compound (145 mg) as a colorless powder Melting point: 250–253° C.

$^1$H-NMR (d$^6$-DMSO) δ: 3.13(dd,J=5 Hz,7 Hz,3H), 3.84 (s,3H), 6.57(m,1H), 7.17(m,1H), 7.40(dd,J=9 Hz,11 Hz,1H), 7.72(dd,J=3 Hz,8 Hz,1H), 7.97(d,J=14 Hz,1H), 8.48(s,1H).

Referential Example 30

Synthesis of 8-Chloro-6,7-difluoro-1-(4-fluoro-3-hydroxyphenyl)-4-oxo-1,4-dihydroquinoline-3-carboxylic Acid Ethyl 8-chloro-6,7-difluoro-1-(4-fluoro-3-methoxyphenyl)-4-oxo-1,4-dihydroquinoline-3-carboxylate (2.3 g) was added to a mixed liquid (1:1, v/v; 20 ml) of 47% hydrobromic acid and acetic acid, and the mixture was stirred and heated under reflux for 78 hours. Deposits were collected by filtration and washed with ethanol and diisopropyl ether in that order to obtain the title compound (1.63 g) as a colorless powder.

Melting point: >280° C.

$^1$H-NMR (d$^6$-DMSO) δ:

7.12(m,1H), 7.25(dd,J=3 Hz,8 Hz,1H), 7.37(dd,J=9 Hz,11 Hz,1H), 8.41(dd,J=9 Hz,10 Hz,1H), 8.60(s,1H).

Example 43

Synthesis of 8-Chloro-6-fluoro-1-(4-fluoro-3-hydroxyphenyl)-7-methylamino-4-oxo-1,4-dihydroquinoline-3-carboxylic Acid 8-Chloro-6,7-difluoro-1-(4-fluoro-3-hydroxyphenyl)-4-oxo-1,4-dihydroquinoline-3-carboxylic acid (300 mg) and an aqueous solution (about 40%; 600 mg) of methylamine were added to pyridine (1,500 mg), and the mixture was stirred at room temperature for 63 hours. The reaction mixture was concentrated under reduced pressure. A process of adding ethanol (3 ml) to the residue and then concentrating the mixture under reduced pressure was conducted twice repeatedly. Ethanol (4 ml) was added to the resultant residue, and the mixture was heated under reflux for 30 minutes. The reaction mixture was allowed to cool, and deposits were collected by filtration and washed with ethanol and diisopropyl ether in that order to obtain the title compound (305 mg) as a colorless powder.

Melting point: >280° C.

$^1$H-NMR (d$^6$-DMSO) δ: 3.11(dd,J=5 Hz,8 Hz,3H), 6.58 (m,1H), 7.03(m,1H), 7.13(dd,J=2 Hz,8 Hz,1H), 7.33(dd,J=9 Hz,11 Hz,1H), 7.95(d,J=14 Hz,1H), 8.40(s,1H).

Referential Example 31

Synthesis of 6,7-Difluoro-1-(4-fluoro-3-hydroxyphenyl)-8-methyl-4-oxo-1,4-dihydroquinoline-3-carboxylic Acid Ethyl 6,7-difluoro-1-(4-fluoro-3-methoxyphenyl)-8-methyl-4-oxo-1,4-dihydroquinoline-3-carboxylate (2.3 g) was added to a mixed liquid (1:1, v/v; :30 ml) of 47% hydrobromic acid and acetic acid, and the mixture was stirred and refluxed for 44 hours. Deposits were collected by filtration and washed with ethanol and diisopropyl ether in that order to obtain the title compound (1.65 g) as a colorless powder.

Melting point: >280° C.

$^1$H-NMR (d$^6$-DMSO) δ: 1.76(d,J=3 Hz,3H), 7.13(m,1H), 7.28(dd,J=3 Hz,8 Hz,1H), 7.41(dd,J=9 Hz,11 Hz,1H), 8.24 (t,J=9 Hz,1H), 8.60(s,1H)).

Example 44

Synthesis of 6-Fluoro-1-(4-fluoro-3-hydroxyphenyl)-8-methyl-7-methylamino-4-oxo-1,4-dihydroquinoline-3-carboxylic Acid 6,7-Difluoro-1-(4-fluoro-3-hydroxyphenyl)-8-methyl-4-oxo-1,4-dihydroquinoline-3-carboxylic acid (403 mg) and an aqueous solution (about 40%; 2.0 g) of methylamine were added to pyridine (2.0 g), and the mixture was stirred at 60° C. for 6 days. The reaction mixture was concentrated under reduced pressure. A process of adding ethanol (5 ml) to the residue and then concentrating the mixture under reduced pressure was conducted 3 times repeatedly. Ethanol (2 ml) was added to the resultant residue, and deposits were collected by filtration and washed with ethanol and diisopropyl ether in that order to obtain the title compound (311 mg) as a colorless powder.

Melting point: >280° C.

$^1$H-NMR (d$^6$-DMSO) δ: 1.61(s,3H), 3.02(m,3H), 6.02(m, 1H), 7.03(m,1H), 7.09(dd,J=3 Hz,8 Hz,1H), 7.36(dd,J=9 Hz,11 Hz,1H), 7.82(d,J=14 Hz,1H), 8.46(s,1H).

Referential Example 32

Synthesis of 4-Fluoro-3-methoxyaniline 3,4-Difluoroaniline (2.6 g) was added to a 28% methanol solution of sodium methoxide, and the mixture was heated for 2 days at about 60° C. and for 4 days at 110° C. After distilled water (50 ml) was added to the reaction mixture, it was extracted with chloroform (50 ml). A chloroform layer was washed with distilled water (20 ml) and then dried over anhydrous magnesium sulfate. The dry chloroform layer was concentrated under reduced pressure to obtain the title compound (2.8 g) as a dark brown oil.

$^1$H-NMR (CDCl$_3$) δ: 3.54(br,2H), 3.84(s,3H), 6.17(dt,J=8 Hz,3 Hz,1H), 6.31(dd,J=3 Hz,7 Hz,1H), 6.86(dd,J=8 Hz,11 Hz,1H).

Referential Example 33

Synthesis of Ethyl 8-Chloro-6,7-difluoro-1-(4-fluoro-3-methoxyphenyl)-4-oxo-1,4-dihydroquinoline-3-carboxylate 4-Fluoro-3-methoxyaniline (1.4 g) was added to a chloroform solution (10 ml) with ethyl 3-ethoxy-2-(3-chloro-2,4,5-trifluorobenzoyl)acrylate synthesized from ethyl 3-chloro-2,4,5-trifluorobenzoylacetate (2.8 g) in accordance with a method known per se in the art dissolved therein. The reaction mixture was concentrated under reduced pressure, and anhydrous potassium carbonate (2.7 g) and N,N-dimethylformamide (6 ml) were added to the residue, followed by stirring at 90° C. for 15 minutes. The reaction mixture was allowed to cool, and chloroform (80 ml) and distilled water (300 ml) were added to the reaction mixture, thereby conducting liquid separation. A chloroform layer was washed twice with distilled water (300 ml), dried over anhydrous magnesium sulfate and then concentrated under reduced pressure. Deposits were dispersed in ethanol, collected by filtration and washed with ethanol and diisopropyl ether in that order to obtain the title compound (2.98 g) as a colorless powder.

Melting point: 245–246° C.

$^1$H-NMR (CDCl$_3$) δ: 1.40(t,J=7 Hz,3H), 3.92(s,3H), 4.39 (q,J=7 Hz,2H), 6.95(m,2H), 7.23(dd,J=8 Hz,11 Hz,1H), 8.33(t,J=9 Hz,1H), 8.45(s,1H).

Referential Example 34

Synthesis of Ethyl 8-Chloro-6,7-difluoro-1-(4-fluoro-5-methoxy-2-nitrophenyl)-4-oxo-1,4-dihydroquinoline-3-carboxylate Ethyl 8-chloro-6,7-difluoro-1-(4-fluoro-3-methoxyphenyl)-4-oxo-1,4-dihydroquinoline-3-carboxylate (830 mg) was added to concentrated sulfuric acid (4 ml), and anhydrous potassium nitrate (250 mg) was added portionwise to the mixture while stirring under ice cooling. The resultant mixture was stirred for 15 minutes under ice cooling and for 50 minutes at room temperature. The reaction mixture was poured into ice water (50 ml) and then extracted with chloroform (50 ml). After a chloroform layer was washed with distilled water (20 ml), dried over anhydrous magnesium sulfate and then concentrated under reduced pressure. Deposits were dispersed in ethanol, collected by filtration and washed with ethanol and diisopropyl ether in that order to obtain the title compound (528 mg) as a colorless powder.

Melting point: 244–248° C.
$^1$H-NMR (CDCl$_3$) δ: 1.37(t,J=7 Hz,3H), 4.11(s,3H), 4.34 (q,J=7 Hz,2H), 7.37(d,J=7 Hz,1H), 8.13(d,J=10 Hz,1H), 8.27(t,J=10 Hz,1H), 8.27(s,1H).

Referential Example 35

Synthesis of 8-Chloro-6,7-difluoro-1-(4-fluoro-5-hydroxy-2-nitrophenyl)-4-oxo-1,4-dihydroquinoline-3-carboxylic Acid Ethyl 8-chloro-6,7-difluoro-1-(4-fluoro-5-methoxy-2-nitrophenyl)-4-oxo-1,4-dihydroquinoline-3-carboxylate (510 mg) was added to a mixed liquid (1:1, v/v; 5 ml) of 47% hydrobromic acid and acetic acid, aid the mixture was stirred and heated under reflux for 46 hours. The reaction mixture was concentrated under reduced pressure. A process of adding distilled water (5 ml) to the residue and then concentrating the mixture under reduced pressure was conducted twice repeatedly. Distilled water (5 ml) was added to the resultant residue, and deposits were collected by filtration. The deposits were dispersed in ethanol (2 ml) and heated to reflux. The reaction mixture was allowed to cool, and deposits were collected by filtration and washed with ethanol and diisopropyl ether in that order to obtain the title compound (220 mg) as a pale brown powder.

Melting point: 248–255° C.
$^1$H-NMR (d$^6$-DMSO) δ: 7.47(d,J=8 Hz,1H), 8.38(d,J=11 Hz,1H), 8.44(t,J=9 Hz,1H), 8.93(s,1H).

Example 45

Synthesis of 8-chloro-6-fluoro-1-(4-fluoro-5-hydroxy-2-nitrophenyl)-7-methylamino-4--oxo-1,4-dihydroquinoline-3-carboxylic Acid Methylamine Salt 8-Chloro-6,7-difluoro-1-(4-fluoro-5-hydroxy-2-nitrophenyl)-4-oxo-1,4-dihydroquinoline-3-carboxylic acid (150 mg) was added to an aqueous solution (about 40%; 750 mg) of methylamine, and the mixture was stirred at room temperature for 6 hours. The reaction mixture was concentrated under reduced pressure. A process of adding ethanol (2 ml) to the residue and then concentrating the mixture under reduced pressure was conducted 3 times repeatedly. Isopropyl alcohol (1.5 ml) was added to the resultant residue. Deposits were collected by filtration and washed with isopropyl alcohol and diisopropyl ether in that order to obtain the title compound (120 mg) as a yellow powder.

Melting point: 200–208° C.
$^1$H-NMR (d$^6$-DMSO) δ: 2.35(s,3H), 3.11(m,3H), 6.28(d, J=8 Hz,1H), 6.53(m,1H), 7.78(d,J=13 Hz,1H), 7.33(dd,J=9 Hz,11 Hz,1H), 7.95(d,J=14 Hz,1H), 8.34(s,1H).

Referential Example 36

Synthesis of 1-(2,4-Difluoro-5-hydroxyphenyl)-6,7-difluoro-8-methyl-4-oxo-1,4-dihydroquinoline-3-carboxylic Acid Ethyl 1-(2,4-difluoro-5-methoxyphenyl)-6,7-difluoro-8-methyl-4-oxo-1,4-dihydroquinoline-3-carboxylate (2.32 g) was added to a mixed liquid (1:1, v/v; 30 ml) of 47% hydrobromic acid and acetic acid, and the mixture was stirred and refluxed for 44 hours. After distilled water (20 ml) was added to the reaction mixture, it was allowed to cool. Deposits were collected by filtration and washed with ethanol and diisopropyl ether in that order to obtain the title compound (1.37 g) as a colorless powder.

Melting point: 270–278° C.
$^1$H-NMR (d$^6$-DMSO) δ: 1.82(d,J=3 Hz,3H), 7.43(d,J=8 Hz,1H), 7.63(t,J=11 Hz,1H), 8.26(d,J=10 Hz,1H), 8.75(s, 1H).

Example 46

Synthesis of 1-(2,4-Difluoro-5-hydroxyphenyl)-6-fluoro-8-methyl-7-methylamino-4-oxo-1,4-dihydroquinoline-3-carboxylic Acid 1-(2,4-Difluoro-5-hydroxyphenyl)-6,7-difluoro-8-methyl-4-oxo-1,4-dihydroquinoline-3-carboxylic acid (300 mg) was added to an aqueous solution (about 40%; 3.0 g) of methylamine to conduct a reaction at 75° C. for 4 days. The reaction mixture was concentrated under reduced pressure. A process of adding ethanol (4 ml) to the residue and then concentrating the mixture under reduced pressure was conducted twice repeatedly. Ethanol (2 ml) was added to the resultant residue. Deposits were collected by filtration and washed with ethanol and diisopropyl ether in that order to obtain the title compound (295 mg) as a pale yellow powder.

Melting point: 269–273° C.
$^1$H-NMR (d$^6$-DMSO) δ: 1.62(s,3H), 3.00(t,J=6 Hz,3H), 6.03(m,1H), 7.13(t,J=9 Hz,1H), 7.48(t,J=10 Hz,1H), 7.80(d, J=13 Hz,1H), 8.46(s,1H).

Example 47

Synthesis of 1-(3-Amino-4-fluorophenyl)-8-chloro-6-fluoro-7-methylamino-4-oxo-1,4-dihydroquinoline-3-carboxylic Acid 1-(3-Amino-4-fluorophenyl)-8-chloro-6,7-difluoro-4-oxo-1,4-dihydroquinoline-3-carboxylic acid (300 mg) and an aqueous solution (about 40%; 500 mg) of methylamine were added to pyridine (1,200 mg), and the mixture was stirred at room temperature for 15 hours. The reaction mixture was concentrated under reduced pressure. A process of adding ethanol (2 ml) to the residue and then concentrating the mixture under reduced pressure was conducted twice repeatedly. Ethanol (2 ml) was added to the resultant residue. Deposits were collected by filtration and washed with ethanol and diisopropyl ether in that order to obtain the title compound (210 mg) as a pale brown powder.

Melting point: 162–166° C.
$^1$H-NMR (d$^6$-DMSO) δ: 3.12(dd,J=5 Hz,8 Hz,3H), 5.59 (brs,2H), 6.59(m,1H), 6.71(m,1H), 6.83(d,J=8 Hz,1H), 7.16 (dd,J=9 Hz,11 Hz,1H), 7.94(d,J=14 Hz,1H), 8.37(s,1H).

Example 48

Synthesis of 1-(5-Amino-2,4-difluorophenyl)-8-chloro-6-fluoro-7-(2-hydroxyethylamino)-4-oxo-1,4-dihydroquinoline-3-carboxylic Acid Ethanolamine Salt 1-(5-Amino-2,4-difluorophenyl)-8-chloro-6,7-difluoro-4-oxo-1,4-dihydroquinoline-3-carboxylic acid (600 mg) and ethanolamine (600 mg) were added to pyridine (2,500 mg), and the mixture was stirred at 50° C. for 1.5 hours. The reaction mixture was concentrated under reduced pressure, and ethanol (6 ml) was added to the residue. Deposits were collected by filtration and washed with ethanol and diisopropyl ether in that order to obtain the title compound (603 mg) as a colorless powder.

Melting point: 153–156° C.
$^1$H-NMR (d$^6$-DMSO) δ: 2.63(m,2H), 3.41(m,2H), 3.54 (brs,4H), 4.85(brs,1H), 5.41(brs,2H), 6.18(brs,1H), 6.92(t, J=8 Hz,1H), 7.36(t,J=11 Hz,1H), 7.92(d,J=14 Hz,1H), 8.30 (s,1H).

Example 49
Synthesis of 1-(5-Amino-2,4-difluorophenyl)-8-chloro-6-fluoro-7-(2-hydroxyethylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (200 mg), ethanolamine (35 mg) and triethylamine (200 mg) were added to pyridine (600 mg), and the mixture was stirred at 50° C. for 15.5 hours. The reaction mixture was concentrated under reduced pressure. A process of adding ethanol (3 ml) to the residue and then concentrating the mixture under reduced pressure was conducted twice repeatedly. Ethanol (1 ml) was added to the resultant residue, and deposits were collected by filtration and washed with ethanol and diisopropyl ether in that order to obtain the title compound (188 mg) as a pale brown powder.

Melting point: 215–219° C.

$^1$H-NMR (d$^6$-DMSO) δ: 3.56(brs,4H), 4.86(br,1H), 5.44 (brs,2H), 6.37(br,1H), 6.98(t,J=8 Hz,1H), 7.39(t,J=11 Hz,1H), 7.95(d,J=14 Hz,1H), 8.47(s,1H).

Example 50
Synthesis of 1-(6-Amino-3,5-difluoropyridin-2-yl)-8-chloro-6-fluoro-7-(2-hydroxyethylamino)-4-oxo-1,4-dihydroquinoline-3-carboxylic Acid Ethanolamine Salt 1-(6-Amino-3,5-difluoropyridin-2-yl)-8-chloro-6,7-difluoro-4-oxo-1,4-dihydroquinoline-3-carboxylic acid (300 mg) and ethanolamine (300 mg) were added to pyridine (1,300 mg), and the mixture was stirred at 50° C. for 2.5 hours. The reaction mixture was concentrated under reduced pressure. A process of adding ethanol (2 ml) to the residue and then concentrating the mixture under reduced pressure was conducted twice repeatedly. Ethanol (4 ml) was added to the resultant residue, and deposits were collected by filtration and washed with ethanol and diisopropyl ether in that order to obtain the title compound (290 mg) as a colorless powder.

Melting point: 218–221° C.

$^1$H-NMR (d$^6$-DMSO) δ: 2.64(m,2H), 3.41(m,2H), 3.54 (brs,4H), 4.89(brs,1H), 6.19(m,1H), 6.73(brs,2H), 7.90(d,J=14 Hz,1H), 7.94(t,J=9 Hz,1H), 8.49(s,1H).

Example 51
Synthesis of 1-(5-Amino-2,4-difluorophenyl)-8-chloro-6-fluoro-7-(2-hydroxy-1-methylethylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (200 mg) and 2-amino-1-propanol (200 mg) were added to pyridine (700 mg), and the mixture was stirred at 50° C. for 1.5 hours. Concentrated hydrochloric acid (200 mg) was added to the reaction mixture, and the resultant mixture was concentrated under reduced pressure. Ethanol (3 ml) was added to the residue, and deposits were collected by filtration and washed with ethanol and disopropyl ether in that order to obtain the title compound (167 mg) as a yellow powder.

Melting point: 153–158° C.

$^1$H-NMR (d$^6$-DMSO) δ: 1.17(d,J=7 Hz,3H), 3.47(m,2H), 4.04(m,1H), 7.04(t,J=9 Hz,1H), 7.41(t,J=11 Hz,1H), 8.01(d, J=14 Hz,1H), 8.50(s,1H).

Example 52
Synthesis of 1-(6-Amino-3,5-difluoropyridin-2-yl)-8-chloro-6-fluoro-7-(2-hydroxy-1-methylethylamino)-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (300 mg) and 2-amino-1-propanol (400 mg) were added to pyridine (1,200 mg), and the mixture was stirred at 45° C. for 16 hours. Concentrated hydrochloric acid (600 mg) was added to the reaction mixture, and the resultant mixture was concentrated under reduced pressure. Ethanol (2 ml) was added to the residue, and deposits were collected by filtration and washed with ethanol and diisopropyl ether in that order to obtain the title compound (168 mg) as a colorless powder.

Melting point: 227–231° C.

$^1$H-NMR (d$^6$-DMSO) δ: 1.17(d,J=6 Hz,3H), 3.47(m,2H), 4.05(m,1H), 5.78(d,J=8 Hz,1H), 6.78(brs,2H), 7.96(t,J=9 Hz,1H), 7.99(d,J=13 Hz,1H), 8.75(s,1H).

Referential Example 37
Synthesis of 8-Chloro-6,7-difluoro-1-[3,5-difluoro-6-(2-hydroxyethylamino)pyridin-2-yl]-4-oxo-1,4-dihydroquinoline-3-carboxylic Acid Ethyl 8-chloro-6,7-difluoro-1-[2,4-difluoro-5-(2-hydroxyethylamino)pyridin-2-yl]-4-oxo-1,4-dihydroquinoline-3-carboxylate (0.91 g) was added to a mixed liquid (1:1, v/v; 4 ml) of 4N hydrochloric acid and acetic acid, and the mixture was stirred and refluxed for 2 hours. After distilled water (2 ml) was added to the reaction mixture, it was allowed to cool. Deposits were collected by filtration and washed with 6N hydrochloric acid, ethanol and diisopropyl ether in that order to obtain the title compound (0.71 g) as a pale brown powder.

Melting point: 160–163° C.

$^1$H-NMR (d$^6$-DMSO) δ: 3.46(m,4H), 4.08(t,J=6 Hz,1H), 7.20(m,1H), 7.80(t,J=10 Hz,1H), 8.39(t,J=9 Hz,1H), 8.93(s,1H).

Example 53
Synthesis of 8-Chloro-6-fluoro-1-[3,5-difluoro-6-(2-hydroxyethylamino)pyridin-2-yl]-7-methylamino-4-oxo-1,4-dihydroquinoline-3-carboxylic Acid 8-Chloro-6,7-difluoro-1-[3,5-difluoro-6-(2-hydroxyethylamino)pyridin-2-yl]-4-oxo-1,4-dihydroquinoline-3-carboxylic acid (250 mg) and an aqueous solution (about 40%; 3 g) of methylamine were added to isopropyl alcohol (4 ml), and the mixture was stirred at room temperature for 15 hours. The reaction mixture was concentrated under reduced pressure. A process of adding ethanol (2 ml) to the residue and then concentrating the mixture under reduced pressure was conducted twice repeatedly. Ethanol (2 ml) was added to the resultant residue, and deposits were collected by filtration and washed with ethanol and diisopropyl ether in that order to obtain the title compound (175 mg) as a pale brown powder.

Melting point: 201–205° C.

$^1$H-NMR (d$^6$-DMSO) δ: 3.13(dd,J=5 Hz,8 Hz,3H), 3.47 (m,4H), 6.64(m,1H), 7.13(m,1H), 7.94(t,J=10 Hz,1H), 7.94 (d,J=14 Hz,1H), 8.63(s,1H).

Example 54
Synthesis of 1-(5-Amino-2,4-difluorophenyl)-6-fluoro-7-methylamino-8-methylthio-4-oxo-1,4-dihydroquinoline-3-carboxylic Acid 1-(5-Amino-2,4-difluorophenyl)-6,7-difluoro-8-methylthio-4-oxo-1,4-dihydroquinoline-3-carboxylic acid (50 mg) was added to pyridine (100 mg). A 40% aqueous solution (120 mg) of methylamine was added, and the resultant mixture was stirred overnight at room temperature and for additional 2 days at 50° C. After the reaction mixture was allowed to cool, the solvent was distilled off under reduced pressure. Ethanol (1 ml) was added to the residue, and solids deposited were collected by filtration to obtain the title compound (25 mg) as a pale brown powder.

Melting point: >232° C. (decomposed).

$^1$H-NMR (d$^6$-DMSO) δ: 1.89(s,3H), 3.16(t,J=6 Hz,3H), 5.37(brs,2H), 6.78–7.00(m,2H), 7.36(t,J=11 Hz,1H), 7.94(d, J=13 Hz,1H), 8.40(s,1H).

Example 55

Synthesis of 1-(5-Amino-2,4-difluorophenyl)-6-fluoro-8-methoxy-7-methylamino-4-oxo-1,4-dihydroquinoline-3-carboxylic Acid Pyridine (200 mg) and a 40% aqueous solution (200 mg) of methylamine were added to 1-(5-amino-2,4-difluorophenyl)-6,7-difluoro-8-methoxy-4-oxo-1,4-dihydroquinoline-3-carboxylic acid (100 mg), and the mixture was stirred at 50° C. for 25 hours. The solvent was distilled off, and ethanol was added to the residue. The resultant mixture was stirred, and solids were collected by filtration and washed with ethanol and diethyl ether to obtain the title compound (33 mg) as a yellow powder.

Melting point: 225–227° C.

$^1$H-NMR (d$^6$-DMSO) δ: 3.02(t,J=5 Hz,3H), 3.15(s,3H), 5.38(brs,2H), 6.41(brs,1H), 7.14(t,J=8 Hz,1H), 7.31(t,J=11 Hz,1H), 7.78(d,J=13 Hz,1H), 8.39(s,1H).

Referential Example 38

Synthesis of 1-(5-Amino-2,4-difluorophenyl)-8-chloro-6,7-difluoro-5-methyl-4-oxo-1,4-dihydroquinoline-3-carboxylic Acid 12N Hydrochloric acid (10 ml) was added to ethyl 1-(5-amino-2,4-difluorophenyl)-8-chloro-6,7-difluoro-5-methyl-4-oxo-1,4-dihydroquinoline-3-carboxylate (400 mg), and the mixture was stirred overnight while heating under reflux. After the reaction mixture was allowed to cool, solids deposited were collected by filtration and washed successively with water and ethanol to obtain the title compound (230 mg) as a colorless powder.

Melting point: 271–274° C.

$^1$H-NMR (d$^6$-DMSO) δ:
2.83(d,J=3 Hz,3H), 7.02(t,J=8 Hz,1H), 7.42(t,J=11 Hz,1H), 8.61(s,1H).

Example 56

Synthesis of 1-(5-Amino-2,4-difluorophenyl)-8-chloro-6-fluoro-5-methyl-7-methylamino-4-oxo-1,4-dihydroquinoline-3-carboxylic Acid Pyridine (200 mg) and a 40% aqueous solution (160 mg) of methylamine were added to 1-(5-amino-2,4-difluorophenyl)-8-chloro-6,7-difluoro-5-methyl-4-oxo-1,4-dihydroquinoline-3-carboxylic acid (50 mg), and the mixture was stirred overnight at room temperature. The solvent and the like were distilled off under reduced pressure, and ethanol (0.5 ml) was added to the residue. Solids deposited were collected by filtration and washed with ethanol and diethyl ether to obtain the title compound (8 mg) as a colorless powder.

Melting point: 239–246° C.

$^1$H-NMR (d$^6$-DMSO) δ: 2.75(d,J=3 Hz,3H), 3.11(m,3H), 5.39(brs,2H), 6.57(brs,1H), 6.87(t,J=8 Hz,1H), 7.37(t,J=11 Hz,1H), 8.38(s,1H).

Example 57

Synthesis of 1-(5-Amino-2,4-difluorophenyl)-6-chloro-8-fluoro-7-methylamino-4-oxo-1,4-diydroquinoline-3-carboxylic Acid Pyridine (200 mg) and a 40% aqueous solution (160 mg) of methylamine were added to 1-(5-amino-2,4-difluorophenyl)-6-chloro-7,8-difluoro-4-oxo-1,4-dihydroquinoline-3-carboxylic acid (140 mg), and the mixture was stirred overnight at room temperature. The solvent and the like were distilled off under reduced pressure, and ethanol (0.5 ml) was added to the residue. Solids deposited were collected by filtration and washed with ethanol and diethyl ether to obtain the title compound (47 mg) as a colorless powder.

Melting point: >280° C.

$^1$H-NMR (d$^6$-DMSO) δ: 2.98(t,J=6 Hz,3H), 5.45(brs,2H), 6.43(brs,1H), 7.10(t,J=8 Hz,1H), 7.40(t,J=10 Hz,1H), 8.05 (s,1H), 8.47(s,1H).

Referential Example 39

Synthesis of 1-(5-Amino-2,4-difluorophenyl)-7-fluoro-6-methyl-4-oxo-1,4-dihydroquinoline-3-carboxylic Acid 12N Hydrochloric acid (5 ml) was added to ethyl 1-(5-tert-butoxycarbonylamino-2,4-difluorophenyl)-7-fluoro-6-methyl-4-oxo-1,4-dihydroquinoline-3-carboxylate (400 mg), and the mixture was stirred for 4 hours while heating under reflux. After the reaction mixture was allowed to cool, solids deposited were collected by filtration, washed successively with water and ethanol and dried to obtain the title compound (250 mg) as a pale yellow powder.

Melting point: >280° C.

$^1$H-NMR (d$^6$-DMSO) δ: 2.42(s,3H), 7.02–7.11(m,2H), 7.51(t,J=11 Hz,1H), 8.37(d,J=8 Hz,1H), 8.83(s,1H).

Example 58

Synthesis of 1-(5-Amino-2,4-difluorophenyl)-6-methyl-7-methylamino-4-oxo-1,4-dihydroquinoline-3-carboxylic Acid Dimethyl sulfoxide (100 mg) and a 40% aqueous solution (50 mg) of methylamine were added to 1-(5-amino-2,4-difluorophenyl)-7-fluoro-6-methyl-4-oxo-1,4-dihydroquinoline-3-carboxylic acid (30 mg), and the mixture was heated and stirred at 40° C. for 3 days. The solvent and the like were distilled off under reduced pressure, and ethanol (0.5 ml) was added to the residue. The mixture was left to stand for 3 days, and solids deposited were collected by filtration and washed with (ethanol and diethyl ether to obtain the title compound (11 mg) as a pale gray powder.

Melting point: >280° C.

$^1$H-NMR (d$^6$-DMSO) δ: 2.23(s,3H), 2.60(d,J=4 Hz,3H), 5.52(brs,2H), 5.79(s,1H), 6.06(brs,1H), 6.99–7.10(m,1H), 7.50(t,J=11 Hz,1H), 7.95(s,1H), 8.56(s,1H).

Example 59

Synthesis of 1-(5-Amino-2,4-difluorophenyl)-6-fluoro-5,8-dimethyl-7-methylamino-4-oxo-1,4-dihydroquinoline-3-carboxylic Acid Pyridine (300 mg) and a 40% aqueous solution (150 mg) of methylamine were added to 1-(5-amino-2,4-difluorophenyl)-6,7-difluoro-5,8-dimethyl-4-oxo-1,4-dihydroquinoline-3-carboxylic acid (110 mg), and the mixture was heated and stirred at 40° C. for 8 days. The solvent and the like were distilled off under reduced pressure, and ethanol (0.5 ml) was added to the residue. The mixture was left to stand for 3 days, and solids deposited were collected by filtration and washed with ethanol and diethyl ether to obtain the title compound (20 mg) as a pale yellow powder.

Melting point: 247–253° C.

$^1$H-NMR (d$^6$-DMSO) δ: 1.63(s,3H), 2.73(s,3H), 2.99(t, J=5 Hz,3H), 5.43(brs,2H), 6.04(brs,1H), 6.85(t,J=8 Hz,1H), 7.41(t,J=11 Hz,1H), 8.42(s,1H).

Referential Example 40

Synthesis of 1-(5-Amino-2,4-difluorophenyl)-7-fluoro-6-methyl-8-nitro-4-oxo-1,4-dihydroquinoline-3-carboxylic Acid 12N Hydrochloric acid (2 ml) was added to ethyl 1-(5-tert-butoxycarbonylamino-2,4-difluorophenyl)-7-fluoro-6- methyl-8-nitro-4-oxo-1,4-dihydroquinoline-3-carboxylate (270 mg), and the mixture was stirred for 2 hours while heating under reflux. After the reaction mixture was allowed to cool, solids deposited were collected by filtration, washed successively with water and ethanol and dried to obtain the title compound (140 mg) as a pale yellow powder.

Melting point: 236–242° C.

$^1$H-NMR (d$^6$-DMSO) δ:
2.49(d,J=2 Hz,3H), 6.97(t,J=8 Hz,1H), 7.36(t,J=11 Hz,1H), 8.62(d,J=8 Hz,1H), 8.72(s,$_1$H).

Example 60

Synthesis of 1-(5-Amino-2,4-difluorophenyl)-6-methyl-7-methylamino-8-nitro-4-oxo-1,4-dihydroquinoline-3-carboxylic Acid Pyridine (500 mg) and a 40% aqueous solution (300 mg) of methylamine were added to 1-(5-amino-2,4-difluorophenyl)-7-fluoro-6-methyl-8-nitro-4-oxo-1,4-dihydroquinoline-3-carboxylic acid (70 mg), and the mixture was heated and stirred overnight at 40° C. Dimethyl sulfoxide (10 drops) was added to the reaction mixture, followed by stirring at 40° C. for 5 hours. The solvent and the like were distilled off under reduced pressure, and ethanol (0.5 ml) was added to the residue. Solids deposited were collected by filtration aid washed with ethanol and diethyl ether to obtain the title compound (53 mg) as a yellow powder.

Melting point: 238–241° C.

$^1$H-NMR (d$^6$-DMSO) δ: 2.34(s,3H), 2.68(s,3H), 5.40(brs, 2H), 6.83(t,J=8 Hz,1H), 7.31(t,J=11 Hz,1H), 8.12(s,1H), 8.40(s,1H).

Referential Example 41

Synthesis of Ethyl 1-[5-(N-tert-butoxycarbonyl-N-methylamino)-2,4-difluorophenyl]-6,7-difluoro-8-methyl-4-oxo-1,4-dihydroquinoline-3-carboxylate N,N-Dimethylformamide (4 ml), potassium carbonate (0.6 g) and methyl iodide (0.6 g) were added to ethyl 1-(5-tert-butoxycarbonylamino-2,4-difluorophenyl)-6,7-difluoro-8-methyl-4-oxo-1,4-dihydroquinoline-3-carboxylate (1.0 g), and the mixture was stirred overnight at 60° C. Ethyl acetate and water were added to the reaction mixture to collect an organic layer. After the organic layer was dried over anhydrous magnesium sulfate, the solvent was distilled off. Ethanol was added to the residue, and solids deposited were collected to obtain the title compound (410 mg) as a colorless powder.

Melting point: 217–218° C.

$^1$H-NMR (CDCl$_3$) δ: 1.34–1.50(m,12H), 1.81(d,J=3 Hz,3H), 3.22(s,3H), 4.41(q,J=7 Hz,2H), 7.15(t,J=9 Hz,1H), 7.30–7.41(m,1H), 8.25(t,J=10 Hz,1H), 8.34(s,1H).

Referential Example 42

Synthesis of 6,7-Difluoro-1-(2,4-difluoro-5-methylaminophenyl)-8-methyl-4-oxo-1,4-dihydroquinoline-3-carboxylic Acid 12N Hydrochloric acid (4 ml) was added to ethyl 1-[5-(N-tert-butoxycarbonyl-N-methylamino)-2,4-difluorophenyl]-6,7-difluoro-8-methyl-4-oxo-1,4-dihydroquinoline-3-carboxylate (400 mg), and the mixture was stirred for 3 days while heating under reflux. After the reaction mixture was allowed to cool, solids were collected by filtration, washed with ethanol and dried to obtain the title compound (240 mg) as a colorless powder.

Melting point: 237.5–238° C.

$^1$H-NMR (d$^6$-DMSO) δ: 1.85(d,J=3 Hz,3H), 2.70(s,3H), 7.12(t,J=8 Hz,1H), 7.49(t,J=10 Hz,1H), 8.27(d,J=10 Hz,1H), 8.72(s,1H).

Example 61

Synthesis of 6-Fluoro-1-(2,4-difluoro-5-methylaminophenyl)-8-methyl-7-methylamino-4-oxo-1,4-dihydroquinoline-3-carboxylic Acid Pyridine (300 mg) and a 40% aqueous solution (150 mg) of methylamine were added to 6,7-difluoro-1-(2,4-difluoro-5-methylaminophenyl)-8-methyl-4-oxo-1,4-dihydroquinoline-3-carboxylic acid (80 mg), and the mixture was heated and stirred at 40° C. for 3 days. After the reaction mixture was allowed to cool, diethyl ether was added, followed by stirring. A supernatant liquid was removed, and ethanol (1 ml) was added to the residue to disperse solids therein. The solids were collected by filtration and washed with ethanol and dried to obtain the title compound (20 mg) as a pale yellow powder.

Melting point: 220–222° C.

$^1$H-NMR (d$^6$-DMSO) δ: 1.68(s,3H), 2.70(d,J=5 Hz,3H), 3.02(t,J=6 Hz,3H), 6.00(brs,1H), 6.07(brs,2H), 7.04(t,J=8 Hz,1H), 7.45(t,J=11 Hz,1H), 7.84(d,J=13 Hz,1H), 8.59(s, 1H).

Example 62

Synthesis of 7-Amino-1-(5-amino-2,4-difluorophenyl)-6-methoxy-8-methyl-4-oxo-1,4-dihydroquinoline-3-carboxylic Acid 12N Hydrochloric acid (2 ml) was added to ethyl 7-amino-1-(5-tert-butoxycarbonylamino-2,4-difluorophenyl)-6-methoxy-8-methyl-4-oxo-1,4-dihydroquinoline-3-carboxylate, and the mixture was heated under reflux for 3 hours. After the reaction mixture was allowed to cool, solids deposited were collected by filtration, washed successively with water and ethanol and then dried to obtain the title compound (52 mg) as a yellow powder.

Melting point: >266° C. (decomposed).

$^1$H-NMR (d$^6$-DMSO) δ: 3.98(s,3H), 6.99(t,J=8 Hz,1H), 7.43(t,J=11 Hz,1H), 7.55(s,1H), 8.38(s,1H).

Example 63

Synthesis of 1-(5-Amino-2,4-difluorophenyl)-6-fluoro-8-hydroxymethyl-7-methylamino-4-oxo-1,4-dihydroquinoline-3-carboxylic Acid Pyridine (300 mg) and a 40% aqueous solution (150 mg) of methylamine were added to 1(5-amino-2,4-difluorophenyl)-6,7-difluoro-8-hydroxymethyl-4-oxo-1,4-dihydroquinoline-3-carboxylic acid (100 mg), and the mixture was stirred overnight at 40° C. The solvent and the like were distilled off, and diethyl ether was added to the residue. A supernatant liquid was removed, and ethanol was added to the resultant residue. Solids deposited were collected by filtration to obtain the title compound (34 mg) as a yellow powder.

Melting point: 243–248° C.

$^1$H-NMR (d$^6$-DMSO) δ: 3.07(m,3H), 4.11(d,J=12 Hz,2H), 4.84(brs,1H), 5.42(brs,2H), 6.27(brs,1H), 7.01(t, J=8 Hz,1H), 7.35(t,J=10 Hz,1H), 7.88(d,J=14 Hz,1H), 8.41 (s,1H).

Example 64

Synthesis of 1-(5-Amino-2,4-difluorophenyl)-8-methyl-7-methylamino-6-nitro-4-oxo-1,4-dihydroquinoline-3-carboxylic Acid Pyridine (500 mg) and a 40% aqueous solution (300 mg) of methylamine were added to 1-(5-amino-2,4-difluorophenyl)-7-fluoro-8-methyl-6-nitro-4-oxo-1,4-dihydroquinoline-3-carboxylic acid (220 mg), and the mixture was stirred for 3 hours at 40° C. and for 2 days at room temperature. Diethyl ether was added to the reaction mixture, followed by stirring. A supernatant liquid was removed, and acetic acid (3 drops) was added to the residue, followed by stirring. Solids deposited were recrystallized from ethanol and N,N-dimethylformamide to obtain the title compound (190 mg) as a reddish brown powder.

Melting point: 275–281° C.

$^1$H-NMR (d$^6$-DMSO) δ: 1.75(s,3H), 2.80(d,J=3 Hz,2H), 5.51(brs,2H), 7.02(t,J=8 Hz,1H), 7.27(brs,1H), 7.45(d,J=11 Hz,1H), 8.55(s,1H), 8.66(s,1H).

Example 65

Synthesis of 7-Amino-1-(5-amino-2,4-difluorophenyl)-8-methyl-6-nitro-4-oxo-1,4-dihydroquinoline-3-carboxylic Acid Pyridine (1.0 ml) and 28% aqueous ammonia (100 mg) were added to 1-(5-amino-2,4-difluorophenyl)-7-fluoro-8-methyl-6-nitro-4-oxo-1,4-dihydroquinoline-3-carboxylic acid (100 mg), and the mixture was stirred at 50° C. for 2 days. Additional 28% aqueous ammonia (0.5 ml) was added, and the mixture was further stirred overnight at 50° C. Diethyl ether was added to the reaction mixture, followed by stirring. A supernatant liquid was removed, and ethanol was added to the residue. Solids deposited were collected by filtration and washed with ethanol to obtain the title compound (59 mg) as a yellow powder.

Melting point: >280° C.

$^1$H-NMR (d$^6$-DMSO) δ:

1.70(s,3H), 5.48(brs,2H), 6.92(t,J=8 Hz,1H), 7.39–7.58 (m,3H), 8.26(s,1H), 8.87(s,1H).

Referential Example 43

Synthesis of 1-(5-Amino-2,4-difluorophenyl)-7-fluoro-8-methyl-6-nitro-4-oxo-1,4-dihydroquinoline-3-carboxylic Acid 12N Hydrochloric acid (10 ml) was added to ethyl 1-5-(tert-butoxycarbonylamino-2,4-difluorophenyl)-7-fluoro-8-methyl-6-nitro-4-oxo-1,4-dihydroquinoline-3-carboxylate (2.0 g), and the mixture was stirred for 2.5 hours while heating under reflux. After the reaction mixture was allowed to cool, solids deposited were collected by filtration, washed successively with water, ethanol and chloroform, and dried to obtain the title compound (1.2 g) as a yellow powder.

Melting point: 250–252° C.

$^1$H-NMR (d$^6$-DMSO) δ: 1.86(d,J=3 Hz,3H), 7.11(t,J=8 Hz,1H), 7.48(t,J=10 Hz,1H), 8.71(s,1H), 8.92(d,J=8 Hz,1H).

Example 66

Synthesis of 1-(5-Amino-2,4-difluorophenyl)-7-ethylamino-8-methyl-6-nitro-4-oxo-1,4-dihydroquinoline-3-carboxylic Acid Pyridine (300 mg) and a 70% aqueous solution (150 mg) of ethylamine were added to 1-(5-amino-2,4-difluorophenyl)-7-fluoro-8-methyl-6-nitro-4-oxo-1,4-dihydroquinoline-3-carboxylic acid (110 mg), and the mixture was stirred at 50° C. for 3 hours. Diethyl ether was added to the reaction mixture, followed by stirring. A supernatant liquid was removed, and solids deposited were recrystallized from N,N-dimethylformamide. The solids were collected by filtration and washed with ethanol to obtain the title compound (75 mg) as a reddish brown powder.

Melting point: 250–254° C.

$^1$H-NMR (d$^6$-DMSO) δ: 1.34–1.50(m,3H), 1.75(s,3H), 3.73–3.86(m,2H), 5.47(brs,2H), 7.25–7.37(m,2H), 7.42(t,J=11 Hz,1H), 8.29(s,1H), 8.71(s,1H).

Referential Example 44

Synthesis of Ethyl 1-(5-Amino-2,4-difluorophenyl)-8-chloro-6,7-difluoro-5-methyl-4-oxo-1,4-dihydroquinoline-3-carboxylate Acetic anhydride (613 mg) and triethyl orthoformate (453 mg) were added to ethyl 3-chloro-2,4,5-trifluoro-6-methylbenzoylacetate (600 mg), and the mixture was heated under reflux for 1 hour. After the reaction mixture was allowed to cool, the reagents and the like were distilled off under reduced pressure. Toluene was additionally added to the residue to conduct azeotropic distillation. Chloroform (3 ml) was added to the residue, and a solution of N-tert-butoxycarbonyl-2,4-difluoro-m-phenylenediamine (490 mg) in chloroform (5 ml) was added dropwise to the resultant mixture, followed by stirring at room temperature for 10 minutes. The solvent in the reaction mixture was distilled off, and the residue was subjected to column chromatography on silica gel to obtain an oily compound (1.1 g) from a fraction eluted with a 1:10 mixture of ethyl acetate and hexane. Potassium carbonate (270 mg) was added to a solution of the whole amount of the thus-obtained compound in N,N-dimethylformamide (5 ml), and the mixture was stirred overnight at room temperature. Ethyl acetate and water were added to the reaction mixture to collect an organic layer. After the organic layer was dried over anhydrous magnesium sulfate, the solvent was distilled off. The resultant residue was subjected to column chromatography on silica gel to obtain the title compound (430 mg) as a pale brown amorphous substance from a fraction eluted with a 1:2 mixture of ethyl acetate and hexane.

$^1$H-NMR (CDCl$_3$) δ: 1.37(t,J=7 Hz,3H), 1.51(s,9H), 2.88 (d,J=3 Hz,3H), 4.38(q,J=7 Hz,2H), 6.78(brs,1H), 7.05(t,J= 10 Hz,1H), 8.28–8.34(m,2H).

Referential Example 45

Synthesis of Ethyl 7-Azido-1-(5-tert-butoxycarbonylamino-2,4-difluorophenyl)-8-chloro-6-fluoro-5-methyl-4-oxo-1,4-dihydroquinoline-3-carboxylate Sodium azide (500 mg) was added to a solution of ethyl 1-(5-tert-butoxycarbonylamino-2 4-difluorophenyl)-8-chloro-6,7-difluoro-5-methyl-4-oxo-1,4-dihydroquinoline-3-carboxylate (2 g) in N,N-dimethylformamide (20 ml), and the mixture was heated and stirred at 70° C. for 4 hours. After water and ethyl acetate were added to the reaction mixture, and an organic layer was collected and dried over anhydrous magnesium sulfate, the solvent was distilled off. The residue was subjected to column chromatography on silica gel to conduct elution with chloroform, thereby obtaining the title compound (1.75 g) as a brown oil.

$^1$H-NMR (CDCl$_3$) δ: 1.37(t,J=7 Hz,3H), 1.51(s,9H), 2.86 (d,J=3 Hz,3H), 4.38(q,J=7 Hz,2H), 6.77(brs,1H), 7.02(dd, J=9 Hz,10 Hz,1H), 8.13–8.25(m,2H).

Referential Example 46

Synthesis of Ethyl 7-Amino-1-(5-tert-butoxycarbonylamino-2,4-difluorophenyl)-8-chloro-6-fluoro-5-methyl-4-oxo-1,4-dihydroquinoline-3-carboxylate Palladium hydroxide-carbon (180 mg) was added to a solution of ethyl 7-azido-1-(5-tert-butoxycarbonylamino-2, 4-difluorophenyl)-8-chloro-6-fluoro-5-methyl-4-oxo-1,4-dihydroquinoline-3-carboxylate (1.75 g) in methanol (9 ml), and the mixture was stirred at room temperature for 2.5 hours in a hydrogen atmosphere. The catalyst was removed by filtration through a membrane filter, and the solvent in the filtrate was distilled off under reduced pressure. The residue was subjected to column chromatography on silica gel to conduct elution with chloroform, thereby obtaining the title compound (1.75 g) as a brown oil.

$^1$H-NMR (CDCl$_3$) δ: 1.37(t,J=7 Hz,3H), 1.50(s,9H), 2.83 (d,J=3 Hz,3H), 4.37(brs,2H), 4.65(brs,2H), 6.75(brs,1H), 7.01(t,J=10 Hz,1H), 8.07–8.25(m,2H).

Example 67

Synthesis of 7-Amino-1-(5-amino-2,4-difluorophenyl)-8-chloro-6-fluoro-5-methyl-4-oxo-1,4-dihydroquinoline-3-carboxylic Acid 12N Hydrochloric acid (5 ml) was added to ethyl 7-amino-1-(5-tert-butoxycarbonylamino-2,4-difluorophenyl)-8-chloro-6-fluoro-5-methyl-4-oxo-1,4-dihydroquinoline-3-carboxylate (1.75 g), and the mixture wags stirred overnight while heating under reflux. After the reaction mixture was allowed to cool, it was neutralized with a 20% aqueous solution of sodium hydroxide, arid solids deposited were collected by filtration. The solids were washed with ethanol and dried to obtain the title compound (570 mg) as a pale brown powder.

Melting point: >280° C.
$^1$H-NMR (d$^6$-DMSO) δ: 2.75(d,J=3 Hz,3H), 5.40(brs, 2H), 6.85–7.00(m,3H), 7.37(t,J=11 Hz,1H), 8.39(s,1H).

Example 68

Synthesis of 1-(5-Amino-2,4-difluorophenyl)-8-chloro-6-fluoro-7-(2,2,2-trifluoroethylamino)-4-oxo-1,4-dihydroquinoline-3-carboxylic Acid 2,2,2-Trifluoroethylamine (50 mg) and pyridine (300 ml) were added to 1-(5-amino-2,4-difluorophenyl)-8-chloro-6,7-difluoro-4-oxo-1,4-dihydroquinoline-3-carboxylic acid (110 mg), and the mixture was stirred at 40° C. for 2 days. Additional 2,2,2-trifluoroethylamine (50 mg) was added, and the mixture was stirred at 40° C. for 2 days. Diethyl ether was added to the reaction mixture, followed by stirring. A supernatant liquid was removed, and solids deposited were collected by filtration and washed with ethanol to obtain the title compound (90 mg) as a colorless powder.

Melting point: 240–241° C.
$^1$H-NMR (d$^6$-DMSO) δ: 4.19–4.36(m,2H), 5.46(brs,2H), 6.94–7.08(m,2H), 7.39(t,J=11 Hz,1H), 8.07(d,J=14 Hz,1H), 8.51(s,1H).

Example 69

Synthesis of 7-(N-2-aminoethyl-N-methylamino)-1-(5-amino-2,4-difluorophenyl)-8-chloro-6-fluoro-4-oxo-1,4-dihydroquinoline-3-carboxylic Acid N-Methylenediamine (17 mg) and triethylamine (35 mg) were added to acetonitrile (5 ml), to which 1-(5-amino-2,4-difluorophenyl)-8-chloro-6,7-difluoro-4-oxo-1,4-dihydroquinoline-3-carboxylic acid (100 mg) was added with heating and stirring at 60° C. The resultant mixture was heated under reflux for 2 hours as it was. After the reaction mixture was allowed to cool, solids deposited were collected by filtration and washed with ethanol and diethyl ether to obtain the title compound (40 mg) as a pale brown powder.

Melting point: 186–194° C. (decomposed)
$^1$H-NMR (d$^6$-DMSO) δ: 2.33(s,3H), 2.79(br,2H), 5.45 (brs,2H), 6.96(t,1H), 7.37(t,J=11 Hz,1H), 7.96(d,J=14 Hz,1H), 8.44(s,1H).

Example 70

Synthesis of 5-Amino-1-(5-amino-2,4-difluorophenyl)-8-chloro-6-fluoro-7-methylamino-4-oxo-1,4-dihydroquinoline-3-carboxylic Acid 5-Amino-1-(5-amino-2,4-difluorophenyl)-8-chloro-6,7-difluoro-4-oxo-1,4-dihydroquinoline-3-carboxylic acid (100 mg) and a methylamine solution (82 mg) were added to pyridine (1 ml), and the mixture was heated and stirred at 30° C. for 4 days. After the reaction mixture was allowed to cool, it was concentrated under reduced pressure. Ethanol was added to the residue, and solids were collected by filtration and washed with diethyl ether to obtain the title compound (63 mg) as a brown powder.

Melting point: 246–255° C. (decomposed).
$^1$H-NMR (d$^6$-DMSO) δ: 3.08(s,3H), 5.38(brs,2H), 6.25 (brs,1H), 6.87(m,1H), 7.34(m,1H), 8.24(s,1H).

Example 71

Synthesis of 1-(5-Amino-2,3,4-trifluorophenyl)-8-chloro-6-fluoro-7-methylamino-4-oxo-1,4-dihydroquinoline-3-carboxylic Acid 1-(5-Amino-2,3,4-trifluorophenyl)-8-chloro-6,7-difluoro-4-oxo-1,4-dihydroquinoline-3-carboxylic acid (100 mg) and a 40% methylamine solution (88 mg) were added to pyridine (1 ml), and the mixture was stirred at room temperature for 2 hours. The reaction mixture was concentrated under reduced pressure, and ethanol was added to the residue. Solids were collected by filtration and washed with diethyl ether to obtain the title compound (55 mg) as a yellow powder.

Melting point: 238–241° C.
$^1$H-NMR (d$^6$-DMSO) δ: 3.35(s,3H), 5.80(s,2H), 6.68(brs,1H), 6.79(m,1H), 7.98(d, J=14 Hz,1H), 8.57(s,1H).

Example 72

Synthesis of 7-Amino-1-(5-amino-2,3,4-trifluorophenyl)-8-chloro-6-fluoro-4-oxo-1,4-dihydroquinoline-3-carboxylic Acid Ethyl 1-(5-tert-butoxycarbonylamino-2,3,4-trifluorophenyl)-8-chloro-6,7-difluoro-4-oxo-1,4-dihydroqinoline-3-carboxylate (300 mg) was added to dimethyl sulfoxide (5 ml), and sodium azide (44 mg) was added portionwise to the mixture. The mixture was stirred overnight at room temperature and heated and stirred for 4 hours at 60° C. After the reaction mixture was allowed to cool, ethyl acetate was added thereto. The resultant mixture was washed 3 times with water, dried over anhydrous magnesium sulfate and then concentrated under reduced pressure. Diethyl ether was added to the residue, and solids were collected by filtration to obtain ethyl 7-azido-1-(5-tert-butoxycarbonylamino-2,3,4-trifluorophenyl)-8-chloro-6-fluoro-4-oxo-1,4-dihydroquinoline-3-carboxylate (200 mg).

This compound (200 mg) was added to methanol (5 ml), and an acetic acid solution of palladium hydroxide-carbon (5 mg) was added to the mixture to conduct stirring at room temperature for 3 hours in a hydrogen atmosphere. The catalyst was removed by filtration through a membrane filter, and the filtrate was concentrated under reduced pressure. Concentrated hydrochloric acid (4 ml) and acetic acid (1 ml) were added to the residue, and the mixture was heated under reflux overnight. After the reaction mixture was allowed to cool, it was concentrated under reduced pressure. Ethanol was added to the resultant residue to conduct concentration under reduced pressure again. Diethyl ether was added to the residue, and solids were collected by filtration to obtain the title compound (140 mg) as a pale brown powder.

Melting point: 166–171° C. (decomposed).
$^1$H-NMR (d$^6$-DMSO) δ: 6.83(m,1H), 7.96(d,J=11 Hz,1H), 8.58(s,1H).

Example 73

Synthesis of 1-(5-Amino-2,4-difluorophenyl)-8-chloro-7-ethylamino-6-fluoro-4-oxo-1,4-dihydroquinoline-3-carboxylic Acid Pyridine (200 mg) and a 40% aqueous solution (250 mg) of methylamine were added to 1-(5-amino-2,4-difluorophenyl)-8-chloro-6,7-difluoro-4-oxo-1,4-dihydroquinoline-3-carboxylic acid (100 mg), and the mixture was heated and stirred overnight at 70° C. The solvent was distilled off under reduced pressure, ethanol (2 ml) was added to the residue, and solids were collected by filtration to obtain the title compound (87 mg) as an orange powder.

Melting point: 252–255° C.
$^1$H-NMR (d$^6$-DMSO) δ: 1.03–1.09(m,3H), 3.36–3.51(m, 2H), 5.45(s,2H), 6.58–6.64(m,1H), 6.97–7.04(m,1H), 7.35–7.43(m,1H), 7.98(d,J=14 Hz,1H), 8.46(s,1H).

Example 74

Synthesis of 1-(5-Amino-2,4-difluorophenyl)-8-fluoro-7-methylamino-4-oxo-1,4-dihydroquinoline-3-carboxylic Acid A 40% aqueous solution (100 mg) of methylamine and 1-(5-amino-2,4-difluorophenyl)-7,8-difluoro-4-oxo-1,4-dihydroquinoline-3-carboxylic acid (100 mg) were added to pyridine (2 ml), and the mixture was stirred at room temperature for 2 hours. The solvent was distilled off under reduced pressure, ethanol (2 ml) was added to the residue, and solids were collected by filtration to obtain the title compound (40 mg) as an orange powder.

Melting point: >300° C. (decomposed).

$^1$H-NMR (d$^6$-DMSO) δ: 2.83(d,J=4 Hz,3H), 5.44(s,2H), 6.88(brs,1H), 7.07–7.13(m,2H), 7.40(t,J=10 Hz,1H), 8.07(d, J=9 Hz,1H), 8.45(s,1H).

Example 75

Synthesis of 1-(5-Amino-2,4-difluorophenyl)-8-chloro-6-fluoro-7-(2-hydroxy-n-propylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (150 mg) and 1-amino-2-propanol (150 mg) were added to pyridine (500 mg), and the mixture was stirred at 45° C. for 16 hours. The reaction mixture was concentrated under reduced pressure. A process of adding ethanol (2 ml) to the residue and then concentrating the mixture under reduced pressure was conducted twice repeatedly. Concentrated hydrochloric acid (150 mg) was added to the residue, and the mixture was concentrated under reduced pressure. Ethanol (1 ml) was added to the resultant residue, and deposits were collected by filtration and washed with ethanol and diisopropyl ether in that order to obtain the title compound (157 mg) as a pale brown powder.

Melting point: 233–236° C.

$^1$H-NMR (d$^6$-DMSO) δ: 1.05(d,J=6 Hz,3H), 3.45(m,2H), 3.77(m,1H), 6.27(br,1H), 6.98(t,J=8 Hz,1H), 7.39(t,J=11 Hz,1H), 7.98(d,J=14 Hz,1H), 8.47(s,1H).

Example 76

Synthesis of 1-(6-amino-3,5-difluoropyridin-2-yl)-8-chloro-6-fluoro-7-(3-hydroxy-n-propylamino)-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (150 mg), 3-amino-1-propanol (75 mg) and triethylamine (110 mg) were added to pyridine (400 mg), and the mixture was stirred at 40° C. for 65 hours. The reaction mixture was concentrated under reduced pressure. A process of adding ethanol (2 ml) to the residue and then concentrating the mixture under reduced pressure was conducted twice repeatedly. Concentrated hydrochloric acid (100 mg) was added to the residue, and the mixture was concentrated under reduced pressure. Ethanol (1.5 ml) was added to the resultant residue, and deposits were collected by filtration and washed with ethanol and diisopropyl ether in that order to obtain the title compound (85 mg) as a pale yellow powder.

Melting point: 136–142° C.

$^1$H-NMR (d$^6$-DMSO) δ: 1.71(m,2H), 3.48(m,2H), 3.59 (m,2H), 4.64(brs,1H), 6.68(m,1H), 6.77(brs,2H), 7.96(t,J=9 Hz,1H), 7.97(d,J=14 Hz,1H), 8.72(s,1H).

Example 77

Synthesis of 7-Allylamino-1-(6-amino-3,5-difluoropyridin-2-yl)-8-chloro-6-fluoro-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (150 mg), allylamine (35 mg) and triethylamine (300 mg) were added to pyridine (400 mg), and the mixture was stirred for 2 hours at 40° C. and for 63 hours at room temperature. The reaction mixture was concentrated under reduced pressure. A process of adding ethanol (2 ml) to the residue and then concentrating the mixture under reduced pressure was conducted twice repeatedly. Ethanol (1.5 ml) was added to the resultant residue, and deposits were collected by filtration and washed with ethanol and diisopropyl ether in that order to obtain the title compound (100 mg) as a pale brown powder.

Melting point: 205–208° C.

$^1$H-NMR (d$^6$-DMSO) δ: 4.10(m,2H), 5.07(m,2H), 5.92 (m,1H), 6.77(brs,2H), 6.87(m,1H), 7.95(d,J=14 Hz,1H), 7.97(J=10 Hz,1H), 8.72(s,1H).

Example 78

Synthesis of 1-(6-Amino-3, 5-difluoropyridin-2-yl)-8-chloro-6-fluoro-4-oxo-7-(pyrrolidin-3-yl)amino-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (200 mg), 3-amino-1-benzylpyrrolidine (97 mg) and triethylamine (160 mg) were added to pyridine (600 mg), and the mixture was stirred for 26 hours at room temperature and f or 15 hours at 60° C. The reaction mixture was concentrated under reduced pressure. A process of adding ethanol (3 ml) to the residue and then concentrating the mixture under reduced pressure was conducted twice repeatedly. Acetic acid (2 ml) and 10% palladium-carbon (25 mg) were added to the resultant residue to conduct hydrogenation for 20 hours at 45° C. and for 21 hours at room temperature. After the catalyst was separated by filtration and washed with acetic acid, the filtrate and washings were concentrated under reduced pressure. A process of adding ethanol (3 ml) to the residue and then concentrating the mixture under reduced pressure was conducted twice repeatedly. Ethanol (2 ml) was added to the resultant residue, and deposits were collected by filtration and washed with ethanol and diisopropyl ether in that order to obtain the title compound (115 mg) as a pale brown powder.

Melting point: 243–248° C. (decomposed).

$^1$H-NMR (d$^6$-DMSO) δ: 1.75(m,2H), 2.07(m,1H), 2.85–3.07(m,4H), 4.43(m,1H), 5.92(m,1H), 6.77(brs,2H), 7.96(t,J=9 Hz,1H), 7.99(d,J=14 Hz,1H), 8.69(s,1H).

Example 79

Synthesis of 1-(5-Amino-2,4-difluorophenyl)-8-chloro-6-fluoro-7-(3,3,3-trifluoro-2-hydroxypropylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (150 mg), 1-amino-3,3,3-trifluoro-2-propanol (120 mg) and triethylamine (120 mg) were added to pyridine (400 mg), and the mixture was stirred for 20 hours at room temperature and for 6 hours at 60° C. The reaction mixture was concentrated under reduced pressure. A process of adding ethanol (3 ml) to the residue and then concentrating the mixture under reduced pressure was conducted twice repeatedly. Concentrated hydrochloric acid (150 mg) was added to the residue, and the mixture was concentrated under reduced pressure. Ethanol (2 ml) was added to the resultant residue, and deposits were collected by filtration and washed with ethanol and diisopropyl ether in that order to obtain the title compound (153 mg) as a colorless powder.

Melting point: 134–138° C.

$^1$H-NMR (d$^6$-DMSO) δ: 3.67(m,1H), 3.79(m,1H), 4.17 (m,1H), 6.55(brs,1H), 7.00(t,J=8 Hz,1H), 7.40(t,J=10 Hz,1H), 8.02(d,J=14 Hz,1H), 8.49(s,1H).

Example 80

Synthesis of 1-(6-Amino-3,5-diflucropyridin-2-yl)-8-chloro-6-fluoro-7-(2-methoxyethylamino)-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (140 mg), 2-methoxyethylamine (40 mg) and triethylamine (200 mg) were added to pyridine (400 mg), and the mixture was stirred for 4 hours at 40° C. and for 65 hours at room temperature. The reaction mixture was concentrated under reduced pressure. Ethanol (2 ml) was added to the residue, and the mixture was then concentrated under reduced pressure. Ethanol (1 ml) was added to the resultant residue, and deposits were collected by filtration and washed with ethanol and diisopropyl ether in that order to obtain the title compound (110 mg) as a colorless powder.

Melting point: 178–179° C.

$^1$H-NMR (d$^6$-DMSO) δ: 3.23(s,3H), 3.41(m,2H), 3.65(m, 2H), 6.45(m,1H), 6.78(brs,2H), 7.96(t,J=9 Hz,1H), 7.97(d, J=14 Hz,1H), 8.73(s,1H).

Example 81

Synthesis of 1-(6-Amino-3,5-difluoropyridin-2-yl)-8-chloro-6-fluoro-7-(2,3-dihydroxy-n-propylamino)-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (150 mg), 3-amino-1,2-propanediol (45 ml) and triethylamine (150 mg) were added to pyridine (500 mg), and the mixture was stirred at 50° C. for 18 hours. The reaction mixture was concentrated under reduced pressure. A process of adding ethanol (2 ml) to the residue and then concentrating the mixture under reduced pressure was conducted twice repeatedly. Concentrated hydrochloric acid (60 mg) was added to the residue, and the mixture was concentrated under reduced pressure. Ethanol (1.5 ml) was added to the resultant residue, and deposits were collected by filtration and washed with ethanol and diisopropyl ether in that order to obtain the title compound (107 mg) as a colorless powder.

Melting point: 166–169° C.

$^1$H-NMR (d$^6$-DMSO) δ: 3.65(m,2H), 4.74(brs,1H), 5.03 (br,1H), 6.23(m,1H), 6.77(brs,2H), 7.96(t,J=9 Hz,1H), 7.97 (d,J=14 Hz,1H), 8.73(s,1H).

Example 82

Synthesis of 5-Amino-1-(6-amino-3,5-difluoropyridin-2-yl)-8-chloro-6-fluoro-7-methoxy-4-oxo-1,4-dihydroquinoline-3-carboxylic Acid 5-Amino-1-(6-amino-3,5-difluoropyridin-2-yl)-8-chloro-6,7-difluoro-4-oxo-1,4-dihydroquinoline-3-carboxylic acid (150 mg) and a methanol solution (about 28%; 200 mg) of sodium methoxide were added to methanol (2 ml), and the mixture was stirred at 45° C. for 3 days. Acetic acid (80 mg) was added to the reaction mixture, and the mixture was heated under reflux for 1 hour. After the reaction mixture was allowed to cool, deposits were collected by filtration and washed with methanol and diisopropyl ether in that order to obtain the title compound (122 mg) as a yellow powder.

Melting point: 230–232° C. (decomposed).

$^1$H-NMR (d$^6$-DMSO) δ: 4.00(d,J=3 Hz,3H), 6.73(brs, 2H), 7.91(t,J=9 Hz,1H), 8.62(s,1H).

Example 83

Synthesis of 7-Allylamino-1-(5-amino-2,4-difluorophenyl)-8-chloro-6-fluoro-4-oxo-1,4-dihydroguinoline-3-carboxylic Acid 1-(5-Amino-2,4-difluorophenyl)-8-chloro-6,7-difluoro-4-oxo-1,4-dihydroquinoline-3-carboxylic acid (100 mg) and allylamine (120 mg) were added to pyridine (300 mg), and the mixture was stirred for 3 hours at 40° C. and for 16 hours at room temperature. The reaction mixture was concentrated under reduced pressure. A process of adding ethanol (2 ml) to the residue and then concentrating the mixture under reduced pressure was conducted twice repeatedly. Ethanol (1 ml) was added to the resultant residue, and deposits were collected by filtration and washed with ethanol and diisopropyl ether in that order to obtain the title compound (67 mg) as a pale brown powder.

Melting point: 187–190° C.

$^1$H-NMR ( d$^6$-DMSO) δ: 4.10(m,2H), 5.05(m,2H), 5.45 (brs,2,H), 5.92(m,1H), 6.85(brt,1H), 6.99(t,J=9 Hz,1H), 7.39(t,J=11 Hz,1H), 7.98(J=14 Hz,1H), 8.46(s,1H).

Example 84

Synthesis of 1-(5-Amino-2,4-difluorophenyl)-8-chloro-6-fluoro-7-(3-hydroxy-n-propylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (150 mg), 3-amino-1-propanol (75 mg) and triethylamine (200 mg) were added to pyridine (350 mg), and the mixture was stirred at 45° C. for 43 hours. The reaction mixture was concentrated under reduced pressure. A process of adding ethanol (2 ml) to the residue and then concentrating the mixture under reduced pressure was conducted twice repeatedly. Concentrated hydrochloric acid (120 mg) was added to the residue, and the mixture was concentrated under reduced pressure. Ethanol (1 ml) was added to the resultant residue, and deposits were collected by filtration and washed with ethanol and diisopropyl ether in that order to obtain the title compound (80 mg) as a colorless powder.

$^1$H-NMR (d$^6$-DMSO) δ: 1.70(m,2H), 3.47(m,2H), 3.59 (m,2H), 6.68(br,1H), 6.99(t,J=9 Hz,1H), 7.39(t,J=11 Hz,1H), 7.98(J=14 Hz,1H), 8.46(s,1H).

Example 85

Synthesis of 1-(6-Amino-3,5-difluoropyridin-2-yl)-8-chloro-7-(ethoxycarbonylmethylamino)-6-fluoro-4-oxo-1,4-dihydroquinoline-3-carboxylic Acid 1-(6-Amino-3,5-difluoropyridin-2-yl)-8-chloro-6,7-difluoro-4-oxo-1,4-dihydroquinoline-3-carboxylic acid (200 mg), glycine ethyl ester hydrochloride (135 mg) and triethylamine (450 mg) were added to pyridine (1,000 mg), and the mixture was stirred at room temperature for 15 hours. The reaction mixture was concentrated under reduced pressure. A process of adding ethanol (2 ml) to the residue and then concentrating the mixture under reduced pressure was conducted 4 times repeatedly. Ethanol (1 ml) and distilled water (1 ml) were added to the resultant residue, and deposits were collected by filtration and washed with ethanol and diisopropyl ether in that order to obtain an about 1:1 mixture (106 mg) of the title compound and 1-(6-amino-3,5-difluoropyridin-2-yl)-8-chloro-6,7-difluoro-4-oxo-1,4-dihydroquinoline-3-carboxylic acid, which is the raw material, as a colorless powder.

$^1$H-NMR (d$^6$-DMSO) δ: 1.19(t,J=7 Hz,3H), 4.14(q,J=7 Hz,2H), 4.27(t,J=6 Hz,2H), 6.80(brs,1H), 6.97(t,J=6 Hz,1H), 7.96(d,J=14 Hz,1H), 8.00(t,J=9 Hz,1H), 8.75(s, 1H).

Example 86

Synthesis of 1-(5-Amino-2,4-difluorophenyl)-6-fluoro-7-(2-hyroxyethylamino)-8-methyl-4-oxo-1,4-dihydroquinoline-3-carboxylic Acid 1-(5-Amino-2,4-difluorophenyl)-6,7-difluoro-8-methyl-4-oxo-1,4-dihydroquinoline-3-carboxylic acid (500 mg), monoethanolamine (410 mg) and N-methylpyrrolidine (170 mg) were added to pyridine (1,500 mg), and the mixture was stirred at 90° C. for 71 hours. The reaction mixture was concentrated under reduced pressure. A process of adding ethanol (1.5 ml) to the residue and then concentrating the mixture under reduced pressure was conducted 3 times repeatedly. The resultant residue was subjected to column chromatography (silica gel: 15 g, eluent; chloroform:methanol=50:1→10:1). Ethanol (0.5 ml) was added to a concentrate of a fraction containing a main product, and the mixture was stirred at room temperature. Deposits formed were collected by filtration and washed with ethanol and diisopropyl ether in that order to obtain the title compound (62 mg) as a brown powder.

Melting point: 166–168° C.

$^1$H-NMR (d$^6$-DMSO) δ: 1.74(s,3H), 3.40(m,2H), 3.50(m, 1H), 4.76(t,J=5 Hz,1H), 5.48(brs,2H), 5.80(m,1H), 6.96(t, J=8 Hz,1H), 7.43(t,J=11 Hz,1H), 7.85(d=13 Hz,1H), 8.49(s, 1H).

Referential Example 47

Synthesis of Ethyl 2,4,5-Trifluoro,-3-isopropyloxybenzoylacetate 2,4,5-Trifluoro-3-hydroxybenzoic acid (4.0 g) was added together with isopropyl iodide (4.7 g) to a mixed liquid of distilled water (10 ml) and ethanol (20 ml), in which sodium hydroxide (1.83 g) had been dissolved. The mixture was stirred and heated under reflux for 23 hours. The reaction mixture was concentrated under reduced pressure. The resultant residue was acidified with concentrated hydrochloric acid, and water (25 ml) was added to conduct extraction twice with chloroform (25 ml). A collected chloroform layer was dried over anhydrous magnesium sulfate and then concentrated under reduced pressure. The resultant residue was subjected to column chromatography (silica gel: 75 g, eluent; chloroform: methanol:acetic acid=500:20:1) to obtain 2,4,5-trifluoro-3-isopropyloxybenzoic acid as a solid residue.

The whole amount of this compound was dissolved in dichloromethane (5 ml), and oxalyl chloride (1 ml) and N,N-dimethylformamide (1 drop) were add(ed to the solution. The mixture was stirred overnight and then concentrated under reduced pressure. On the other hand, magnesium powder (760 mg) was added to ethanol (1 ml), and carbon tetrachloride (60 μl) was further added, followed by stirring. A solution of diethyl malonate (5.2 g) in a mixed liquid of tetrahydrofuran (16 ml) and ethanol (1 ml) was added dropwise to the reaction mixture at such a rate that the reaction mixture moderately refluxed. After completion of the addition, the mixture was heated under reflux for 1 hour. A third of the reaction mixture was chilled to −60° C., to which a solution with the above-obtained residue of the acid chloride dissolved in tetrahydrofuran (5 ml) was added dropwise. The temperature of the resultant mixture was given back to room temperature to concentrate it under reduced pressure. Concentrated hydrochloric acid (1.5 ml), distilled water (10 ml) and chloroform (20 ml) were added to the resultant residue to conduct liquid separation. A chloroform layer was concentrated under reduced pressure. p-Toluenesulfonic acid monohydrate (150 mg) was added together with distilled water (10 ml) to the resultant residue, and the mixture was stirred at 90° C. for 9 hours. The reaction mixture was allowed to cool and extracted with chloroform (50 ml). A chloroform layer was washed with a 2% aqueous solution (10 ml) of sodium hydrogencarbonate, dried over anhydrous magnesium sulfate and then concentrated under reduced pressure to obtain the title compound (2.9 g) as a yellow oil.

Referential Example 48

Synthesis of Ethyl 1-[5-(Tert-butoxycarbonylamino)-2,4-difluorophenyl]-6,7-difluoro-8-isopropyloxy-4-oxo-1,4-dihydroquinoline-3-carboxylate Ethyl 2,4,5-trifluoro-3-isopropyloxybenzoylacetate (2.9 g) was stirred together with ethyl orthoformate (2.4 g) and acetic anhydride (2.8 g) at 140° C. for 1 hour while removing distillate. The reaction mixture was concentrated under reduced pressure at the same temperature. After the residue was allowed to cool, a process of adding toluene (10 ml) to the residue and then concentrating the mixture under reduced pressure was conducted twice repeatedly. Ethyl 3-ethoxy-2-(2,4,5-trifluoro-3-isopropyloxybenzoyl)acrylate obtained as the residue was dissolved in chloroform (20 ml). N-(tert-Butoxycarbonyl)-2,4-difluoro-m-phenylenediamine (900 mg) was added to a half of this solution. The resultant mixture was concentrated under reduced pressure. Anhydrous potassium carbonate (1.3 g) and N,N-dimethylformamide (2.5 ml) were added to the resultant residue, and the mixture was stirred at 90° C. for 10 minutes. The reaction mixture was allowed to cool, and chloroform (50 ml) and distilled water (300 ml) were added to conduct liquid separation. A chloroform layer was washed twice with distilled water (300 ml), dried over anhydrous magnesium sulfate and then concentrated under reduced pressure. Deposits were dispersed in ethanol, collected by filtration and washed with ethanol to obtain the title compound (1.18 g) as a pale yellow powder.

Melting point: 194–197° C.

Referential Example 49

Synthesis of 1-(5-Amino-2,4-difluorophenyl)-6,7-difluoro-8-isopropyloxy-4-oxo-1,4-dihydroquinoline-3-carboxylic Acid Ethyl 1-[5-(tert-butoxycarbonylamino)-2,4-difluorophenyl]-6,7-difluoro-8-isopropyloxy-4-oxo-1,4-dihydroquinoline-3-carboxylate (530 mg) were added to a mixed liquid of 4N hydrochloric acid (2 ml) and acetic acid (2 ml), and the mixture was stirred and heated under reflux for 50 minutes. The reaction mixture was concentrated under reduced pressure. Deposits were dispersed in ethanol, collected by filtration and washed with ethanol and diisopropyl ether in that order to obtain the title compound (285 mg) as a pale brown powder.

Melting point: 217–222° C.

$^1$H-NMR (d$^6$-DMSO) δ: 0.84(d,J=6 Hz,3H), 0.88(d,J=6 Hz,3H), 7.10(t,J=8 Hz,1H), 7.36(t,J=11 Hz,1H), 8.08(t10 Hz,1H), 8.56(s,1H).

Example 87

Synthesis of 1-(5-Amino-2,4-difluorophenyl)-6-fluoro-8-isopropyloxy-7-methylamino-4-oxo-1,4-dihydroquinoline-3-carboxylic Acid 1-(5-Amino-2,4-difluorophenyl)-6,7-difluoro-8-isopropyloxy-4-oxo-1,4-dihydroquinoline-3-carboxylic acid (100 mg) was added to a 40% aqueous solution (2.1 g) of methylamine, and the mixture was left to stand for 24 hours at about 55° C. The reaction mixture was concentrated under reduced pressure. Diisopropyl ether (0.5 ml) was added to the residue, and deposits were separated by filtration. The filtrate was concentrated under reduced pressure. Ethanol (about 0.1 ml) was added to the resultant residue, and the mixture was left to stand. Deposits were collected by filtration and washed with ethanol and diisopropyl ether in that order to obtain the title compound (60 mg) as a pale brown powder.

Melting point: 232–236° C. (decomposed).

$^1$H-NMR (d$^6$-DMSO) δ: 0.72(d,J=6 Hz,3H), 0.82(d,J=6 Hz,3H), 3.01(m,3H), 3.90(m,1H), 5.38(brs,2H), 6.14(m, 1H), 7.13(t,J=8 Hz,1H), 7.30(t,J=11 Hz,1H), 7.77(d=13 Hz,1H), 8.39(s,1H).

Example 88

Synthesis of 1-(5-Amino-2,4-difluorophenyl)-8-methyl-6-fluoro-7-(3-hydroxy-n-propylamino)-4-oxo-1,4-dihydroquinoline-3-carboxylic Acid 1-(5-Amino-2,4-difluorophenyl)-8-methyl-6,7-difluoro-4-oxo-1,4-dihydroquinoline-3-carboxylic acid (500 mg), 3-amino-1-propanol (400 mg) and N-methylpyrrolidine (170 mg) were added to pyridine (1,500 mg), and the mixture was stirred at 70° C. for 15 hours. Since the raw material were not dissolved, N,N-dimethylformamide (1 ml) was added to the mixture, followed by stirring at 70° C. for 43 hours. The reaction mixture was concentrated under reduced pressure. A process of adding distilled water (1 ml) to the residue and then concentrating the mixture under reduced pressure was conducted 3 times repeatedly. Another process of adding toluene (1.5 ml) to the resultant residue and then concentrating the mixture under reduced pressure was conducted 3 times repeatedly. A further process of adding ethanol (1.5 ml) to the resultant residue and then concentrating the mixture under reduced pressure was conducted 3 times repeatedly. Ethanol (1 ml) was added to the resultant residue, and the mixture was heated under reflux for 5 minutes and allowed to cool. Deposits were collected by filtration and washed with ethanol and diisopropyl ether in that order to obtain the title compound (155 mg) as a colorless powder.

Melting point: 221–224° C.

$^1$H-NMR (d$^6$-DMSO) δ: 1.67(m,2H), 1.71(s,3H), 4.60(t, J=5 Hz,1H), 5.50(brs,2H), 5.99(m,$_1$H), 6.98(t,J=8 Hz,1H), 7.43(t,J=11 Hz,1H), 7.85(d=13 Hz,1H), 8.49(s,1H).

Example 89

Synthesis of 1-(6-Amino-3,5-difluoropyridin-2-yl)-8-bromo-6-fluoro-7-(2-hydroxyethylamino)-4-oxo-1,4-dihydroquinoline-3-carboxylic Acid Ethanolamine Salt 1-(6-Amino-3,5-difluoropyridin-2-yl)-8-bromo-6,7-difluoro-4-oxo-1,4-dihydroqinoline-3-carboxylic acid (350 mg) and ethanolamine (350 mg) were added to pyridine (1,400 mg), and the mixture was stirred at 50° C. for 3.5 hours. The reaction mixture was concentrated under reduced pressure. A process of adding ethanol (2 ml) to the residue and then concentrating the mixture under reduced pressure was conducted 3 times repeatedly. Ethanol (1 ml) was added to the resultant residue, and deposits were collected by filtration and washed with ethanol and diisopropyl ether in that order to obtain the title compound (151 mg) as a colorless powder.

Melting point: 189–192° C. (decomposed).

$^1$H-NMR (d$^6$-DMSO) δ: 2.63(m,2H), 3.39(m,2H), 3.56 (brs,4H), 4.90(brs,1H), 6.03(m,1H), 6.73(brs,2H), 7.93(t, J=9 Hz,1H), 7.94(d,J=14 Hz,1H), 8.51(s,1H).

Example 90

Synthesis of (S)-1-(5-amino-2,4-difluorophenyl)-8-chloro-6-fluoro-7-(2-hydroxy-n-propylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (150 mg) and (S)-1-amino-2-propanol (150 mg) were added to pyridine (450 mg), and the mixture was stirred at 55° C. for 2.5 hours. The reaction mixture was concentrated under reduced pressure. A process of adding ethanol (2 ml) to the residue and then concentrating the mixture under reduced pressure was conducted twice repeatedly. Concentrated hydrochloric acid (150 mg) was added to the resultant residue, and the mixture was concentrated under reduced pressure. Ethanol (1 ml) was added to the resultant residue, and deposits were collected by filtration and washed with ethanol and diisopropyl ether in that order to obtain the title compound (147 mg) as a colorless powder.

Melting point: 225–226° C.

$^1$H-NMR (d$^6$-DMSO) δ: 1.06(d,J=6 Hz,3H), 3.45(m,2H), 3.77(m,1H), 4.91(m,1H), 5.45(brs,2H), 6.27(m,1H), 6.98(t, J=8 Hz,1H), 7.39(t,J=11 Hz,1H), 7.98(d=14 Hz,1H), 8.47(s, 1H).

Example 91

Synthesis of (R)-1-(5-amino-2,4-difluorophenyl)-8-chloro-6-fluoro-7-(2-hydroxy-n-propylamino)-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (150 mg) and (R)-1-amino-2-propanol (150 mg) were added to pyridine (450 mg), and the mixture was stirred at 55° C. for 2.5 hours. The reaction mixture was concentrated under reduced pressure. A process of adding ethanol (2 ml) to the residue and then concentrating the mixture under reduced pressure was conducted twice repeatedly. Concentrated hydrochloric acid (150 mg) was added to the resultant residue, and the mixture was concentrated under reduced pressure. Ethanol (1 ml) was added to the resultant residue, and deposits were collected by filtration and washed with ethanol and diisopropyl ether in that order to obtain the title compound (164 mg) as a colorless powder.

Melting point: 224–226° C.

$^1$H-NMR (d$^6$-DMSO) δ: 1.06(d,J=6 Hz,3H), 3.46(m,2H), 3.77(m,1H), 4.91(t,J=4 Hz,1H), 5.45(brs,2H), 6.27(m,1H), 6.98(t,J=8 Hz,1H), 7.39(t,J=11 Hz,1H), 7.98(d=14 Hz,1H), 8.47(s,1H).

Example 92

Synthesis of Ethyl 1-(2,4-Difluoro-5-methoxyphenyl)-6-fluoro-8-methyl-7-nitro-4-oxo-1,4-dihydroquinoline-3-carboxylate 2,4-Difluoro-5-methoxyaniline monohydrobromide (780 mg) and a solution of triethylamine (328 mg) in chloroform (10 ml) were added dropwise to a solution of ethyl 3-ethoxy-2-(2',5'-difluoro-3'-methyl-4'-nitrobenzoyl)acrylate (2.0 g) in chloroform (10 ml) at 0° C. After the mixture was stirred for 10 minutes, the solvent and the like were distilled off. Anhydrous potassium carbonate (510 mg) was added to a solution of the whole amount of the residue in N,N-dimethylformamide (10 ml), and the mixture was stirred at 70° C. for 5 hours. Ethyl acetate and water were added to the reaction mixture to collect an organic layer. After the organic layer was dried over anhydrous magnesium sulfate, the solvent was distilled off. Ethanol was added to the residue to disperse it therein, and filtration was conducted to obtain the title compound (660 mg) as a pale yellow powder.

Melting point: 248–250° C.

$^1$H-NMR (CDCl$_3$) δ: 1.40(t,J=7 Hz,3H), 1.83(s,3H), 3.92 (s,3H), 4.40(q,J=7 Hz,2H), 6.69(t,J=8 Hz,1H), 7.16(t,J=10 Hz,1H), 8.31(t=9 Hz,1H), 8.40(s,1H).

Example 93

Synthesis of Ethyl 7-Amino-1-(2,4-difluoro-5-methoxyphenyl)-6-fluoro-8-methyl-4-oxo-1,4-dihydroquinoline-3-carboxylate Acetic acid (10 ml) and iron powder (720 mg) were added to ethyl 1-(4-fluoro-2-methyl-5-nitrophenyl)-6-fluoro-8-methyl-7-nitro-4-oxo-1,4-dihydroquinoline-3-carboxylate (660 mg), and the mixture was stirred at 90° C. for 110 minutes. The catalyst in the reaction mixture was removed by filtration through Celite, and the solvent in the residue was distilled off. Chloroform and water were added to the resultant residue to collect an organic layer. After the organic layer was dried over anhydrous magnesium sulfate, the solvent was distilled off. Ethanol was added to the residue to disperse it therein, and filtration was conducted to obtain the title compound (420 mg) as a pale yellow powder.

Melting point: 232–235° C.

$^1$H-NMR (CDCl$_3$) δ: 1.39(t,J=7 Hz,3H), 1.66(s,3H), 3.88 (s,3H), 4.23(brs,2H), 4.38(q,J=7 Hz,2H), 6.91(t,J=8 Hz,1H), 7.10(t,J=10 Hz,1H), 8.06(d,J=11 Hz,1H), 8.28(s,1H).

Example 94
Synthesis of 7-Amino-1-(2,4-difluoro-5-hydroxyphenyl)-6-fluoro-8-methyl-4-oxo-1,4-dihydroquinoline-3-carboxylic Acid 48% hydrobromic acid (3 ml) and acetic acid (2 ml) were added to ethyl 7-amino-1-(2,4-difluoro-5-methoxyphenyl)-6-fluoro-8-methyl-4-oxo-1,4-dihydroquinoline-3-carboxylate (420 mg), and the mixture was stirred for 2 days while heating under reflux. After the reaction mixture was allowed to cool, solids deposited were collected by filtration. The solids were washed with water, ethanol and diethyl ether in that order and dried to obtain the title compound (108 mg) as a pale brown powder.

Melting point: >280° C.

$^1$H-NMR (d$^6$-DMSO) δ: 1.61(s,3H), 6.50(t,J=8 Hz,1H), 7.61(t,J=11 Hz,1H), 7.84(d,J=11 Hz,1H), 8.50(s,1H).

Referential Example 50
Synthesis of Ethyl 1-(4-Fluoro-2-methylphenyl)-6-fluoro-8-methyl-7-nitro-4-oxo-1,4-dihydroquinoline-3-carboxylate A solution of 4-fluoro-2-methylaniline (about 1 g) in chloroform (5 ml) was added dropwise to a solution of ethyl 3-ethoxy-2-(2',5'-difluoro-3'-methyl-4'-nitrobenzoyl)acrylate (2.0 g) in chloroform (10 ml) at room temperature (while confirming the disappearance of the acrylate by tlc). After the mixture was stirred for 10 minutes, the solvent and the like were distilled off. Potassium carbonate (800 mg) was added to a solution of the whole amount of the residue in dimethylformamide (3 ml), and the mixture was stirred at 110° C. for 20 minutes. Chloroform and water were added to the reaction mixture to collect an organic layer. After the organic layer was dried over anhydrous magnesium sulfate, the solvent was distilled off. Ethanol was added to the residue to disperse it therein, and filtration was conducted to obtain the title compound (1.1 g) as a pale yellow powder.

Melting point: 207–209° C.

$^1$H-NMR (CDCl$_3$) δ: 1.41(t,J=7 Hz,3H), 1.66(s,3H), 2.12 (s,3H), 4.41(q,J=7 Hz,2H), 7.06–7.20(m,2H), 7.35(dd,J=5 Hz,9 Hz,1H), 8.31–8.41(m,2H).

Example 95
Synthesis of Ethyl 1-(4-Fluoro-2-methyl-5-nitrophenyl)-6-fluoro-8-methyl-7-nitro-4-oxo-1,4-dihydroquinoline-3-carboxylate Ethyl 1-(4-fluoro-2-methylphenyl)-6-fluoro-8-methyl-7-nitro-4-oxo-1,4-dihydroquinoline-3-carboxylate (1.1 g) was added to concentrated sulfuric acid (10 ml), and potassium nitrate (330 mg) was added to the mixture under ice cooling. The resultant mixture was stirred at room temperature for 4 days. The reaction mixture was poured into ice water and extracted with chloroform. A chloroform layer was dried over anhydrous magnesium sulfate, and the solvent was distilled off to obtain the title compound (1.1 g) as a pale yellow amorphous substance.

$^1$H-NMR (CDCl$_3$) δ: 1.40(t,J=7 Hz,3H), 1.71(s,3H), 2.23 (s,3H), 4.39(q,J=7 Hz,2H), 7.42(d,J=11 Hz,1H), 8.20–8.40 (m,3H).

Example 96
Synthesis of Ethyl 7-Amino-1-(5-amino-4-fluoro-2-methylphenyl)-6-fluoro-8-methyl-4-oxo-1,4-dihydroquinoline-3-carboxylate Acetic acid (10 ml) and iron powder (1.6 g) were added to ethyl 1-(4-fluoro-2-methyl-5-nitrophenyl)-6-fluoro-8-methyl-7-nitro-1,4-dihydro-4-oxoquinoline-3-carboxylate (1.1 g), and the mixture was stirred overnight at 90° C. The catalyst in the reaction mixture was removed by filtration through Celite, and the solvent in the residue was distilled off. The resultant residue was purified by column chromatography on silica gel (chloroform:methanol 20:1) to obtain the title compound (230 mg) as a yellow amorphous substance.

$^1$H-NMR (d$^6$-DMSO) δ: 1.25(t,J=7 Hz,3H), 1.48(s,3H), 1.92(s,3H), 3.37(brs,2H), 4.19(q,J=7 Hz,2H), 5.95(brs,2H), 7.40(t,J=11 Hz,1H), 7.75(t,J=11 Hz,1H), 8.01(d,J=7 Hz,1H), 8.13(s,1H).

Example 97
Synthesis of 7-Amino-1-(5-amino-4-fluoro-2-methylphenyl)-6-fluoro-8-methyl-4-oxo-1,4-dihydroquinoline-3-carboxylic Acid 12N Hydrochloric acid (2 ml) was added to ethyl 7-amino-1-(5-amino-4-fluoro-2-methylphenyl)-6-fluoro-8-methyl-4-oxo-1,4-dihydroquinoline-3-carboxylate (230 mg), and the mixture was stirred for 3 hours while heating under reflux. After the reaction mixture was allowed to cool, solids deposited were collected by filtration. The solids were washed with water, ethanol and diethyl ether in that order and dried to obtain the title compound (42 mg) as a pale yellow powder.

Melting point: >240° C.

$^1$H-NMR (d$^6$-DMSO) δ: 1.57(s,3H), 1.79(s,3H), 5.44(brs, 2H), 6.41(brs,2H), 6.82(t,J=9 Hz,1H), 7.12(t,J=12 Hz,1H), 7.86(d,J=11 Hz,1H), 8.29(s,1H).

Referential Example 51
Synthesis of 3,4,6-Trifluoro-2-methoxy-5-methylbenzoic Acid n-Butyllithium (1.69 M hexane solution; 30 ml) was added dropwise to a solution of diisopropylamine (7.7 ml) in tetrahydrofuran (30 ml) at −70° C. under purging with nitrogen, and the mixture was stirred at −70° C. for 15 minutes. A solution of 3,4,6-trifluoro-2-methoxybenzoic acid (5 g) in tetrahydrofuran (40 ml) was added dropwise to the reaction mixture at the same temperature, and the resultant mixture was stirred for 15 minutes. Methyl iodide (6 ml) was added dropwise to the reaction mixture at the same temperature, and the mixture was left to stand to room temperature as it was, and then stirred overnight. The solvent was distilled off. Diethyl ether and water were added to the residue to conduct liquid separation. A water layer was acidified with concentrated hydrochloric acid and extracted with diethyl ether. An organic layer was dried over anhydrous magnesium sulfate, and the solvent and the like were distilled off to obtain the title compound (3.6 g) as a red oil.

$^1$H-NMR (CDCl$_3$) δ: 2.21(s,3H), 4.05(s,3H).

Referential Example 52
Synthesis of Ethyl 1-(5-Tert-butoxycarbonylamino-2,4-difluorophenyl)-6,7-difluoro-5-methoxy-8-methyl-4-oxo-1,4-dihydroquinoline-3-carboxylate Ethyl 2,4,5-trifluoro-2-methoxy-5-methylbenzoylacetate (1.9 g) was synthesized from 2,4,5-trifluoro-2-methoxy-5-methylbenzoic acid (3.6 g) in accordance with a method known per se in the art.

Acetic anhydride (1.8 g) and triethyl orthoformate (1.2 g) were added to benzoyl acetate (1.9 g), and the mixture was heated under reflux for 70 hours. After the reaction mixture was allowed to cool, the reagents and the like were distilled off under reduced pressure. Chloroform (10 ml) was added to a half of the resultant residue, and a solution of N-tert-butoxycarbonyl-4,6-difluoro-phenylenediamine (910 mg) in chloroform (10 ml) was added dropwise to the resultant mixture, followed by stirring at room temperature for 20 minutes. The solvent in the reaction mixture was distilled off to obtain an aminoacrylate derivative.

Potassium carbonate (520 mg) was added to a solution of the whole amount of the aminoacrylate derivative in N,N-dimethylformamide (5 ml), and the mixture was stirred at 80° C. for 90 minutes. Ethyl acetate and water were added to the reaction mixture to collect an organic layer. After the organic layer was dried over anhydrous magnesium sulfate, the solvent was distilled off. Ethanol was added to the residue to collect solids deposited, thereby obtaining the title compound (630 mg) as a pale yellow powder.

Melting point: 193–194° C.

$^1$H-NMR (CDCl$_3$) δ: 1.40(t,J=7 Hz,3H), 1.51(s,9H), 1.71 (d,J=3 Hz,3H), 4.11(s,3H), 4.38(q,J=7 Hz,2H), 6.78(brs, 1H), 7.08(t,J=10 Hz,1H), 8.20(s,1H), 8.20–8.30(m,2H).

Referential Example 53

Synthesis of 1-(5-Amino-2,4-difluorophenyl)-6,7-difluoro-5-hydroxy-8-methyl-4-oxo-1,4-dihydroquinoline-3-carboxylic Acid 12N Hydrochloric acid (2 ml) was added to ethyl 1-5-(tert-butoxycarbonylamino-2,4-difluorophenyl)-6,7-difluoro-5-methoxy-8-methyl-4-oxo-1,4-dihydroquinoline-3-carboxylate (600 mg), and the mixture was heated and stirred at 100° C. for 2 hours. The reaction mixture was allowed to cool, and solids deposited were collected by filtration and washed with ethanol to obtain the title compound (280 mg).

Melting point: >280° C.

$^1$H-NMR (d$^6$-DMSO) δ: 1.69(d,J=3 Hz,3H), 5.55(brs, 2H), 7.04(t,J=8 Hz,1H), 7.45(t,J=11 Hz,1H), 8.58(s,$_1$H).

Example 98

Synthesis of 1-(5-Amino-2,4-difluorophenyl)-6-fluoro-5-hydroxy-8-methyl-7-methylamino-4-oxo-1,4-dihydroquinoline-3-carboxylic Acid Pyridine (300 mg) and a 40% aqueous solution (300 mg) of methylamine were added to 1-(5-amino-2,4-difluorophenyl)-6,7-difluoro-5-hydroxy-8-methyl-4-oxo-1,4-dihydroquinoline-3-carboxylic acid (100 mg), and the mixture was stirred at 30° C. for 2 days. Acetic acid (1 drop) and ethanol (1 ml) were added to the reaction mixture, and the solvent was distilled off. Methanol was added to the residue, and solids were collected by filtration to obtain the title compound (33 mg) as a brown powder.

Melting point: >280° C.

$^1$H-NMR (d$^6$-DMSO) δ: 1.54(s,3H), 3.00–3.10(m,3H), 5.47(brs,2H), 6.12(brs,1H), 6.91(t,J=8 Hz,1H), 7.42(t,J=11 Hz,1H), 8.39(s,1H).

Example 99

Synthesis of 1-(5-Amino-2,4-difluorophenyl)-6-fluoro-7-methoxy-8-methyl-4-oxo-1,4-dihydroquinoline-3-carboxylic Acid Methanol (500 mg) and sodium methoxide (28% methanol solution; 200 mg) were added to 1-(5-amino-2,4-difluorophenyl)-6,7-difluoro-8-methyl-4-oxo-1,4-dihydroquinoline-3-carboxylic acid (350 mg), and the mixture was heated and stirred at 40° C. for 2 days. Acetic acid (2 drops) was added to the reaction mixture to collect solids by filtration. The solids were washed with ethanol and dried to obtain the title compound (290 mg) as a pale yellow powder.

Melting point: >280° C.

$^1$H-NMR (d$^6$-DMSO) δ: 1.83(d,J=3 Hz,3H), 3.92(s,3H), 5.51(brs,2H), 7.02(t,J=9 Hz,1H), 7.42(t,J=11 Hz,1H), 8.05 (d,J=11 Hz,1H), 8.51(s,1H).

Referential Example 54

Synthesis of Ethyl 1-(5-Tert-butoxycarbonylamino-2,4-difluorophenyl)-6,7-difluoro-8-(trimethylsilylethynyl)-4-oxo-1,4-dihydroquinoline-3-carboxylate Ethyl 1-(5-tert-butoxycarbonylamino-2,4-difluorophenyl)-8-bromo-6,7-difluoro-4-oxo-1,4-dihydroquinoline-3-carboxylate (6 g), tributylstannyltrimethylsilylacetylene (6 g) and tetrakis(triphenylphosphine) palladium (0.4 g) were added to dry toluene (30 ml). This suspension was heated under reflux overnight in a nitrogen atmosphere. After the temperature of the reaction mixture was given back to room temperature, the solvent was distilled off under reduced pressure. Ethyl acetate was added to the residue, and the mixture was washed with water. After an organic layer was collected and dried over anhydrous magnesium sulfate, the solvent was distilled off under reduced pressure. The resultant residue was subjected to column chromatography on silica gel (silica 240 cc/chloroform) to obtain the title compound (4.6 g) as a colorless powder.

Melting point: 198–199° C.

$^1$H-NMR (CDCl$_3$) δ: 0.09(s,9H), 0.92(t,J=7 Hz,3H), 1.51 (s,9H), 4.39(q,J=7 Hz,2H), 6.77(brs,1H), 7.01(t,J=9 Hz,1H), 8.32(s,1H), 8.29–8.36(m,2H).

Referential Example 55

Synthesis of 1-(5-Tert-butoxycarbonylamino-2,4-difluorophenyl)-6,7-difluoro-8-ethynyl-4-oxo-1,4-dihydroquinoline-3-carboxylic Acid Ethyl 1-(5-tert-butoxycarbonylamino-2,4-difluorophenyl)-6,7-difluoro-8-(trimethylsilylethynyl)-4-oxo-1,4-dihydroquinoline-3-carboxylate (750 mg) was dissolved in tetrahydrofuran (6 ml). 1N Sodium hydroxide (2 ml) was added to this solution, and the mixture was stirred overnight at room temperature. After the reaction mixture was acidified with citric acid and then extracted with chloroform. An organic layer was dried over anhydrous magnesium sulfate, and the solvent was then distilled off under reduced pressure to obtain the title compound (240 mg) as a colorless powder.

$^1$H-NMR (CDCl$_3$) δ: 1.51(s,9H), 3.44(s,1H), 6.83(brs, 1H), 7.06(t,J=9 Hz,1H), 8.40–8.43(m,2H), 8.65(s,1H).

Referential Example 56

Synthesis of 1-(5-Amino-2,4-difluorophenyl)-8-ethynyl-6,7-difluoro-1,4-dihydro-4-oxoquinoline-3-carboxylic Acid 1-(5-tert-Butoxycarbonylamino-2,4-difluorophenyl)-8-ethynyl-6,7-difluoro-4-oxo-1,4-dlhydroquinoline-3-carboxylic acid (240 mg) and anisole (10 mg) were dissolved in trifluoroacetic acid (4 ml), and the solution was stirred overnight at room temperature. After trifluoroacetic acid was distilled off under reduced pressure, ethyl acetate was added to the residue. The mixture was washed with an aqueous solution of sodium hydrogencarbonate and water in that order. After an organic layer was dried over anhydrous magnesium sulfate, the solvent was distilled off under reduced pressure. The resultant residue was subjected to column chromatography on silica gel (silica 240 cc/chloroform) to obtain the title compound (130 mg) as a brown powder.

Melting point: >223° C. (decomposed).

$^1$H-NMR (d$^6$-DMSO) δ: 4.92(s,1H), 5.47(brs,2H), 7.06 (t,J=8 Hz,1H), 7.34(t,J=11 Hz,1H), 8.41(t,J=10 Hz,1H), 8.71(s,1H).

Example 100

Synthesis of 1-(5-Amino-2,4-difluorophenyl)-8-ethynyl-6-fluoro-7-methylamino-4-oxo-1,4-dihydroquinoline-3-carboxylic Acid 1-(5-Amino-2,4-difluorophenyl)-8-ethynyl-6,7-difluoro-4-oxo-1,4-dihydroquinoline-3-carboxylic acid (40 mg) was dissolved in pyridine (0.3 ml), and a 40% methylamine solution (1 ml) was added to this solution, followed by stirring at room temperature for 5 hours. The solvent was distilled off under reduced pressure, and diethyl ether was added to the residue. Solids were collected by filtration to obtain the title compound (30 mg) as a brown powder.

Melting point: 208–209° C.

$^1$H-NMR (d$^6$-DMSO) δ: 3.15(t,J=6 Hz,3H), 4.70(s,1H), 5.38(brs,2H), 6.47(brs,1H), 6.97(t,J=8 Hz,1H), 7.29(t,J=11 Hz,1H), 7.94(d,J=14 Hz,1H), 8.44(s,1H).

Example 101

Synthesis of 7-Amino-1-(5-amino-2,4-difluorophenyl)-8-chloro-6-fluoro-4-oxo-1,4-dihydroquinoline-3-amidocarboxylic Acid Ethyl 1-(5-amino-2,4-difluorophenyl)-8-chloro-6,7-difluoro-4-oxo-1,4-dihydroquinoline-3-carboxylate (200 mg) was dissolved in N,N-dimethylformamide (4 ml). 28% Aqueous ammonia (1 ml) was added to this solution, and the mixture was stirred overnight at 50° C. in a closed state. Additional 28% aqueous ammonia (2 ml) was added, and the mixture was stirred overnight in the same manner as described above. After the temperature of the reaction mixture was given back to room temperature, it was concentrated to two-thirds under reduced pressure. Red solids deposited were collected by filtration, washed with water and then dried to obtain the title compound (90 mg) as a reddish brown powder.

Melting point: >261° C. (decomposed).

$^1$H-NMR (d$^6$-DMSO) δ: 5.47(brs,2H), 6.75(brs,2H), 7.00–7.03(m,1H), 7.43(t,J=10 Hz,1H), 7.72(s,1H), 7.96(d, J11 Hz,1H), 8.34(s,1H), 9.14(s,1H).

Example 102

Synthesis of 1-(5-Amino-2,4-difluorophenyl)-8-chloro-6-fluoro-7-methylamino-4-oxo-1,4-dihydroquinoline-3-methylamidocarboxylic Acid Ethyl 1-(5-amino-2,4-difluorophenyl)-8-chloro-6,7-difluoro-4-oxo-1,4-dihydroquinoline-3-carboxylate was dissolved in N,N-dimethylformamide (20 ml). A 40% methylamine solution was added to this solution, and the mixture was stirred overnight at 50° C. in a closed state. Additional 40% methylamine solution was added, and the mixture was stirred overnight at 50° C. in a closed state. Ethyl acetate was added to this solution, and solids deposited were removed by filtration. After the filtrate was washed with water and dried over anhydrous magnesium sulfate, the solvent was distilled off under reduced pressure. The residue was subjected to column chromatography on silica gel (silica 600 cc/chloroform) to obtain the title compound (42 mg) as a brown powder.

Melting point: 206–208° C.

$^1$H-NMR (CDCl$_3$) δ: 2.82–2.84(m,3H), 3.18(t,J=5 Hz,3H), 3.47(brs,2H), 4.36(brs,2H), 5.81–5.89(m,1H), 5.89 (brs,1H), 6.83(t,J=10 Hz,1H), 7.79(d,J=14 Hz,1H), 8.12(brs, 1H).

Example 103

Synthesis of 1-(5-Amino-2,4-difluorophenyl)-7-hydroxy-6-nitro-4-oxo-1,4-dihydroquinoline-3-carboxylic Acid 1-(5-Amino-2,4-difluorophenyl)-7-fluoro-6-nitro-4-oxo-1,4-dihydroquinoline-3-carboxylic acid (60 mg) was added to a 5% aqueous solution (3 ml) of sodium hydroxide, and the mixture was stirred at 40° C. for 2 hours. The reaction mixture was acidified with a 3% aqueous solution of citric acid, and solids formed were collected by filtration. The solids were subjected to azeotropic distillation with ethanol and toluene. Hexane was added to the residue to conduct filtration, thereby obtaining the title compound (49 mg) as a yellow powder.

Melting point: >246° C. (decomposed).

$^1$H-NMR (d$^6$-DMSO) δ: 5.58(brs,2H), 6.56(s,1H), 7.02 (dd,1H), 7.54(dd,1H), 8.74(brs,2H).

Example 104

Synthesis of 1-(5-Amino-2,4-difluorophenyl)-7-methoxy-6-nitro-4-oxo-1,4-dihydroquinoline-3-carboxylic Acid 1-(5-Amino-2,4-difluorophenyl)-7-fluoro-6-nitro-4-oxo-1,4-dihydroquinoline-3-carboxylic acid (60 mg) was added to a mixed liquid of a 28% sodium methoxide solution (135 mg) and pyridine (0.5 ml), and the mixture was stirred at 40° C. for 2 hours. The reaction mixture was acidified with a 3% aqueous solution of citric acid, and solids formed were collected by filtration. The solids were subjected to azeotropic distillation with ethanol and toluene. Hexane was added to the residue to conduct filtration, thereby obtaining the title compound (20 mg) as a yellow powder.

Melting point: >255° C. (decomposed).

$^1$H-NMR (d$^6$-DMSO) δ: 3.89(s,3H), 4.61(brs,2H), 6.59 (s,1H), 6.96(dd,1H), 7.13(dd,J=9 Hz,J=10 Hz,1H), 8.69(s, 1H), 8.94(s,1H).

Example 105

Synthesis of 1-(5-Amino-2,4-difluorophenyl)-8-chloro-6-fluoro-7-(oxetan-3-yl)amino-4-oxo-1,4-dihydroquinoline-3-carboxylic Acid 1-(5-Amino-2,4-difluorophenyl)-8-chloro-6,7-difluoro-4-oxo-1,4-dihydroquinoline-3-carboxylic acid (100 mg) was dissolved in a mixed liquid of pyridine (0.5 ml) and N-methylpyrrolidone (0.5 ml). A methanol solution (45%; 1.5 ml) of 3-aminooxetane was added to the resultant solution. The mixture was stirred at 70° C. for 18 hours. The reaction mixture was acidified with a 3% aqueous solution (20 ml) of citric acid, and solids formed were collected by filtration. The solids were subjected to azeotropic distillation with ethanol. Ether (5 ml) was added to the residue to conduct filtration, thereby obtaining the title compound (48 mg) as a pale yellow powder.

Melting point: 240–244° C.

$^1$H-NMR (d$^6$-DMSO) δ: 4.55–4.82(m,4H), 4.85–4.95(m, 1H), 5.45(brs,2H), 6.79(brs,1H), 6.98(dd,J=8 Hz,J=9 Hz,1H), 7.38(dd,J=10 Hz,J=11 Hz,1H), 7.98(d,J=13 Hz,1H), 8.50(s,1H).

Test Example (1) Antibacterial Action

The minimum inhibitory concentrations (MIC; μg/ml) of specimen compounds against standard strains [S. aureus 209P (S.a.), S. epidermidis IFO 12293 (S.e.) and P. aeruginosa IFO 3445 (P.a.)] were determined in accordance with the standard method (CHEMOTHERAPY, 29(1), 76, 1981) prescribed by The Japan Chemotherapeutic Association. The results are shown in Table 1.

TABLE 1

| Specimen compound | MIC (μg/ml) | | |
| --- | --- | --- | --- |
| | S.a. | S.e. | P.a. |
| Compound of Example 11 | 0.013 | 0.05 | 0.20 |
| Compound of Example 12 | 0.013 | 0.05 | 0.10 |
| Compound of Example 14 | 0.013 | 0.025 | 0.20 |
| Compound of Example 16 | 0.013 | 0.05 | 0.39 |
| Compound of Example 19 | 0.013 | 0.05 | 0.39 |
| Compound of Example 28 | 0.006 | 0.025 | 0.39 |
| Compound of Example 30 | 0.006 | 0.025 | 0.78 |
| Compound of Example 56 | 0.006 | 0.013 | 0.20 |
| Compound of Example 59 | 0.006 | 0.013 | 0.39 |

TABLE 1-continued

| Specimen compound | MIC (µg/ml) | | |
|---|---|---|---|
| | S.a. | S.e. | P.a. |
| Compound of Example 70 | 0.013 | 0.025 | 0.20 |
| Compound of Example 77 | 0.013 | 0.013 | 0.39 |
| Compound of Example 88 | 0.013 | 0.025 | 0.78 |
| Compound of Example 98 | 0.013 | 0.013 | 0.39 |
| Compound of Example 99 | 0.013 | 0.05 | 0.78 |
| Cyprofloxacin | 0.10 | 0.78 | 0.39 |
| Levofloxacin | 0.20 | 0.39 | 0.78 |
| Sparfloxacin | 0.05 | 0.20 | 0.78 |
| Tosufloxacin | 0.05 | 0.20 | 0.39 |

(2) Absorption Excretion

The recovery rates in both urine and bile of compounds according to the present invention upon oral administration to rats were determined to evaluate their absorbability and excretory behavior.

(a) Urinary Recovery Rate

Male SD rats aged 6 weeks fasted overnight were forced to orally administer a 0.5% methyl cellulose suspension (20 mg/10 ml/kg or 10 mg/10 ml/kg) of each of specimen compounds using a peroral sound. Urine was collected twice in the course of from 0 up to 6 hours and from 6 up to 24 hours after the administration. The concentration of the specimen compound in the urine was determined by a paper disk method using *Bacillus subtilis* ATCC 6633 as a tester strain to find its recovery rate in urine. The results are shown in Table 2.

(2) Biliary Recovery Rate

A polyethylene tube was inserted into the common bile ducts of male SD rats aged 6 weeks fasted overnight under etherization. After the anesthetic wore away, the rats were forced to orally administer each of the specimen compounds in the same manner as in the item (a) to collect bile till 24 hours after the administration. The concentration of the specimen compound in the bile was determined in the same manner as in the item (a) after hydrolysis with an alkali (0.1N, NaOH, 37° C., 1 hour) or without being subjected to any treatment, thereby finding its recovery rate in bile. The results are shown in Table 2.

TABLE 2

| | Recovery rate (%) | | | |
|---|---|---|---|---|
| | In urine | | In bile* | Total recovery rate |
| | 0–6 hours | 6–24 hours | 0–24 hours | 0–24 hours |
| Compound of Example 11 | 9.7 | 13.7 | 90.0 | 113.4 |
| Compound of Example 12 | 4.8 | 10.8 | 81.7 | 97.3 |
| Compound of Example 14 | 1.2 | 2.6 | 103.1 | 106.9 |
| Levofloxacin | 21.2 | 13.7 | 48.3 | 83.2 |
| Tosufloxacin | 19.0 | 12.3 | 9.2 | 40.5 |
| Referential** compound | 7.6 | 2.7 | 11.1 | 21.5 |

*Recovery rate in bile after hydrolysis with the alkali.
**7-(3-Aminoazetidin-1-yl)-1-(5-amino-2,4-difluoro-phenyl)-8-chloro-6-fluoro-4-oxo-1,4-dihydroquinoline-3-carboxylic acid.

INDUSTRIAL APPLICABILITY

The pyridonecarboxylic acid derivatives according to the present invention or the salts thereof exhibit excellent anti-bacterial activities and peroral absorbability, scarcely cause side effects, and are easy of synthesis. The medicines according to the present invention comprising such a compound as an active ingredient are useful as agents for preventing or treating infectious diseases of the human or animals, and besides as medicines for fish' diseases, agricultural chemicals and food preservatives.

What is claimed is:

1. A pyridonecarboxylic acid derivative or a salt thereof represented by the general formula (1):

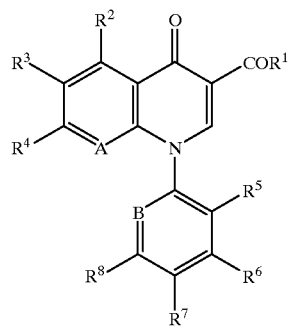

(1)

wherein $R^1$ is a group —$OR^9$ (wherein $R^9$ is a hydrogen atom or carboxy-protecting group), amino group or lower alkyl-amino group; $R^2$ is a hydrogen atom, nitro group, amino or hydroxyl group which may protected, lower alkyl group, or lower alkoxy group; $R^3$ is a halogen atom, hydrogen atom, nitro group, lower alkyl group, lower alkoxy group or amino group; $R^4$ is a nitro group, azido group, hydrazino group which may be substituted, group —$NR^{10}R^{11}$ (wherein $R^{10}$ and $R^{11}$ may be the same or different from each other and are independently a hydrogen atom, lower alkyl group which may be substituted, lower alkenyl group, lower cycloalkyl group, saturated heterocyclic group or amino-protecting group), lower alkoxyl group or hydroxyl group; $R^5$, $R^6$ and $R^7$ may be the same or different from one another and are independently a hydrogen atom, nitro group, halogen atom or lower alkyl group; $R^8$ is a nitro group, amino group which may be substituted, hydroxyl group or lower alkoxyl group; A is a nitrogen atom or a group C—$R^{12}$ (wherein $R^{12}$ is a hydrogen atom, halogen atom, lower alkyl group which may be substituted, lower alkenyl group, lower alkynyl group, lower alkoxy group, lower alkylthio group or nitro group); and B is a nitrogen atom or group C—$R^{13}$ (wherein $R^{13}$ is a hydrogen atom or halogen atom).

2. A medicinal composition comprising the pyridonecarboxylic acid derivative or the salt thereof according to claim 1 and a pharmaceutically acceptable carrier.

3. A method of treating an infectious disease, which comprises administering to a mammal or fish an effective amount therefor of the pyridonecarboxylic acid derivative or the salt thereof according to claim 1.

* * * * *